(12) United States Patent
Chen et al.

(10) Patent No.: US 10,047,137 B2
(45) Date of Patent: Aug. 14, 2018

(54) ANTIBODIES AGAINST NOVEL PD1 ISOFORMS AND USES THEREOF

(71) Applicant: VERSITECH LIMITED, Hong Kong (CN)

(72) Inventors: Zhiwei Chen, Hong Kong (CN); Lin Cheng, Hong Kong (CN); Allen Ka Loon Cheung, Hong Kong (CN); Jingying Zhou, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 10 days.

(21) Appl. No.: 14/246,811

(22) Filed: Apr. 7, 2014

(65) Prior Publication Data

US 2014/0302070 A1 Oct. 9, 2014

Related U.S. Application Data

(60) Provisional application No. 61/808,993, filed on Apr. 5, 2013.

(51) Int. Cl.
| | |
|---|---|
| *C07K 16/28* | (2006.01) |
| *C07K 14/705* | (2006.01) |
| *A61K 39/12* | (2006.01) |
| *A61K 39/00* | (2006.01) |

(52) U.S. Cl.
CPC ........ *C07K 14/70503* (2013.01); *A61K 39/12* (2013.01); *C07K 14/70521* (2013.01); *C07K 16/2818* (2013.01); *A61K 2039/53* (2013.01); *A61K 2039/55516* (2013.01); *C12N 2740/16234* (2013.01)

(58) Field of Classification Search
None
See application file for complete search history.

(56) References Cited

U.S. PATENT DOCUMENTS 5,811,248 A * 9/1998 Ditlow ............... G01N 33/92
9,029,315 B2 * 5/2015 Chen .................. A61K 39/21
514/1

OTHER PUBLICATIONS

R & D Systems 2005 Catalog,Minneapolis, R & D Systems, Inc., p. 465, 2005.*
Lazar-Molnár et al., Crystal structure of the complex between programmed death-1 (PD-1) and its ligand PD-L2, PNAS 105(30):10483-10488, Jul. 2008.*
Neilsen et al.. Alternative splice variants of the human PD-1 gene, Cellular Immunol. 235(2):109-116, Jun. 2005.*
Cheng et al., Monoclonal antibodies specific to human delta42PD1: A novel immunoregulator potentially involved in HIV-1 and tumor pathogenesis, mAbs, 7(3):620-629, May/Jun. 2015.*
PE anti-mouse CD279 (PD-1) antibody RMP1-30, BioLegend Inc., see URL<www.biolegend.com>, Version 1, Revision Date Nov. 30, 2012.*

(Continued)

*Primary Examiner* — Claire Kaufman
(74) *Attorney, Agent, or Firm* — Saliwanchik, Lloyd & Eisenschenk

(57) ABSTRACT

The present invention pertains to antibodies against a novel isoform of human PD1 protein (Δ42PD1) that contains a 42-nucleotide in-frame deletion in exon 2. The invention also pertains to methods of using the antibodies against Δ42PD1 for the treatment for autoimmune disorders. In certain embodiments, the antibodies against Δ42PD1 are monoclonal.

4 Claims, 29 Drawing Sheets
(9 of 29 Drawing Sheet(s) Filed in Color)

(56) References Cited

OTHER PUBLICATIONS

Induced expression of PD1, a novel member of the immunoglobulin gene superfamily, upon programmed cell death.
Engagement of the PD-1 immunoinhibitory receptor by a novel B7 family member leads to negative regulation of lymphocyte activation.
PD-L2 is a second ligand for PD1 and inhibits T cell activation.
The B7 family revisited.
The PD-1-PD-L pathway in immunological tolerance.
PD1 on dendritic cells impedes innate immunity against bacterial infection.
A regulatory polymorphism in PDCD1 is associated with susceptibility to systemic lupus erythematosus in humans.
Association of a programmed death 1 gene polymorphism with the development of rheumatoid arthritis, but not systemic lupus erythematosus.
Programmed death PD-1PD-ligand 1 PD-ligand 2 pathway inhibits T cell effector functions during human tuberculosis.
PD1 expression on HIV-specific T cells is associated with T-cell exhaustion and disease progression.
PD1 expression in acute hepatitis C virus (HCV) infection is associated with HCV-specific CD8 exhaustion.
Alternative splice variants of the human PD-1 gene.
Aberrant regulation of synovial T cell activation by soluble costimulatory molecules in rheumatoid arthritis.
Overexpression of the Ctla-4 isoform lacking exons 2 and 3 causes autoimmunity.
Identification of three alternatively spliced variants of human CD28 mRNA.
A novel costimulatory signaling in human T lymphocytes by a splice variant of CD28.
Understanding alternative splicing towards a cellular code.
Human GC-AG alternative intron isoforms with weak donor sites show enhanced consensus at acceptor exon positions.
Crystal structure of the complex between programmed death-1 (PD-1) and its ligand PD-L2.
Inflammatory signals in dendritic cell activation and the induction of adaptive immunity.
Gene transfer into muscle by electroporation in vivo.
Establishment of a murine model of malignant mesothelioma.
IFNbeta1a modulates the expression of CTLA-4 and CD28 splice variants in human mononuclear cells induction of soluble isoforms.
Detection of circulating soluble CD28 in patients with systemic lupus erythematosus, primary Sjogren's syndrome and systemic sclerosis.
Aberrant production of soluble costimulatory molecules CTLA-4, CD28, CD80 and CD86 in patients with systemic lupus erythematosus.
Plasma sCD28, sCTLA-4 levels in neuromyelitis optica and multiple sclerosis during relapse.
Vaccine design for CD8 T lymphocyte responses.
Design Construction and Characterization of a Multigenic Modified Vaccinia Ankara Candidate Vaccine Against Human Immunodeficiency Virus Type 1 Subtype C B.
Design, Construction, and Characterization of a Dual-Promoter Multigenic DNA Vaccine Directed Against an HIV-1 Subtype C B Recombinant.
Novel Vaccination Protocol with Two Live Mucosal Vectors Elicits Strong Cell-Mediated Immunity in the Vagina and Protects against Vaginal Virus Challenge.
HIV-1 Gag-specific immunity induced by a lentivector-based vaccine directed to dendritic cells.
Dendritic cell loss from nonlymphoid tissues after systemic administration of lipopolysaccharide, tumor necrosis factor, and interleukin 1.
TNF-alpha—dependent maturation of local dendritic cells is critical for activating the adaptive immune response to virus infection.
Microbial Compounds Selectively Induce Th1 Cell-Promoting or Th2 Cell-Promoting Dendritic Cells In Vitro with Diverse Th Cell-Polarizing Signals.
Impact of measles virus dendriticcell infection on Th-cell polarization in vitro.
Tumor necrosis factor-a and interleukin 6 synergistically induce T cell growth.
IL-6 Produced by Type I IFN DC Controls IFN-γ Production by Regulating the Suppressive Effect of CD4+ CD25+ Regulatory T Cells.
Development of a multicomponent candidate vaccine for HIV-1.
CD86 (B7-2) Can Function to Drive MHC-Restricted Antigen-Specific CTL Responses In Vivo.
DNA vaccination antigen presentation and the induction of immunity.
Combined effects of IL-12 and electroporation enhances the potency of DNA vaccination in macaques.
Type I interferon supports primary CD8+ T-cell responses to peptide-pulsed dendritic cells in the absence of CD4+ T-cell help.
IL-15 as a mediator of CD4+ help for CD8+ T cell longevity and avoidance of TRAIL-mediated apoptosis.
Inflammatory Cytokines Determine the Susceptibility of Human CD8 T Cells to Fas-mediated Activation-induced Cell Death through Modulation of FasL and c-FLIPS Expression.
Vaccine Immunity to Pathogenic Fungi Overcomes the Requirement for CD4 Help in Exogenous Antigen Presentation to CD8+ T Cells.
Soluble PD-1 rescues the proliferative response of simian immunodeficiency virus-specific CD4 and CD8 T cells during chronic infection.
Toll-like receptor signalling.
HMGB1 Is a Therapeutic Target for Sterile Inflammation and Infection.
Toll-like receptor 4-dependent contribution of the immune system to anticancer chemotherapy and radiotherapy.
Interleukin 12 induces tyrosine phosphorylation and activation of STAT4 in human lymphocytes.
Expansion of human γσ T cells in vitro is differentially regulated by the measles virus glycoproteins.
Professional Antigen-Presentation Function by Human γσ T Cells.
Cross-presenting human γσ T cells induce robust CD8+ αβ T cell responses.
The mucosal barrier and immune activation in HIV pathogenesis.
Increased Toll-Like Receptor 4 Expression on T Cells May Be a Mechanism for Enhanced T cell Response Late After Burn Injury.
Regulatory T Cells Selectively Express Toll-like Receptors and Are Activated by Lipopolysaccharide.
Viral gene expression during the establishment of human cytomegalovirus latent infection in myeloid progenitor cells.
Microbial isoprenoid biosynthesis and humanQNT cell activation.
In vitro stimulation with a non-peptidic alkylphosphate expands cells expressing Vγ2-Jγ1 .2 Vσ2 T-cell receptors.
Human T Cell Receptor γσ Cells Recognize Endogenous Mevalonate Metabolites in Tumor Cells.
Expression and function of Toll-like receptors in T lymphocytes.
CCR5 antagonist TD-0680 uses a novel mechanism for enhanced potency against HIV-1 entry, cell-mediated infection, and a resistant variant.
Dendritic-cell control of pathogen-driven T-cell polarization.
Differential roles of MDA5 and RIG-I helicases in the recognition of RNA viruses.
Signaling of High Mobility Group Box 1 (HMGB1) through Toll-like Receptor 4 in Macrophages Requires CD14.
Effect of IL-18 on Expansion of γσ T Cells Stimulated by Zoledronate and IL-2.
F18, a Novel Small-Molecule Nonnucleoside Reverse Transcriptase Inhibitor, Inhibits HIV-1 Replication Using Distinct Binding Motifs as Demonstrated by Resistance Selection and Docking Analysis.
Prolonged antigen survival and cytosolic export in cross-presenting human γσ T cells.

(56) References Cited

OTHER PUBLICATIONS

Molecular Pathways in Virus-Induced Cytokine Production.
Gammadelta T cells novel initiators of adaptive immunity.
Measurement of Proliferative Responses of cultured lymphocytes.
IL-15 is a novel growth factor for murine gamma delta T cells induced by *Salmonella* infection.
Activation of gd T Cells in Malaria Interaction of Cytokines and a Schizont Associated Plasmodium falciparum Antigen.
Human Immunodeficiency Virus Type 1 Induces Persistent Changes in Mucosal and Blood γσ T Cells despite Suppressive Therapy.
Rapid generation of combined CMV-specific CD4+ and CD8+ T-cell lines for adoptive transfer into recipients of allogeneic stem cell transplants.
Toll-like receptor 4 signaling in T cells promotes autoimmune inflammation.
LPS-Induced Cytokine Production in Human Monocytes and Macrophages.
NIH Image to ImageJ 25 years of image analysis.
Bridging innate and adaptive immunity through gammadelta T-dendritic cell crosstalk.
MD-2, a Molecule that Confers Lipopolysaccharide Responsiveness on Toll-like Receptor 4.
Activation of gamma delta T cells for production of IFN-gamma is mediated by bacteria via macrophage-derived cytokines IL-1 and IL-12.
Nonpeptide ligands for human gamma delta T cells.
Interleukin-12 activates human gamma delta T cells synergistic effect of tumor necrosis factor-alpha.
Distinct Cytokine-Driven Responses of Activated Blood γσ T Cells Insights into Unconventional T Cell Pleiotropy.
A critical cysteine is required for HMGB1 binding to Toll-like receptor 4 and activation of macrophage cytokine release.
Inhibition of STAT4 activation by lisofylline is associated with the protection of autoimmune diabetes.
Toll-like receptor-4 mediates obesity-induced non-alcoholic steatohepatitis through activation of X-box binding protein-1 in mice.
PD1-based DNA vaccine amplifies HIV-1 GAG-specific CD8+ T cells in mice.
Potentiating functional antigen-specific CD8+T cell immunity by a novel PD1 isoform-based fusion DNA vaccine.
Inhibitory B7-family molecules in the tumour microenvironment.
Ishida, Y. et al., Induced expression of PD-1, a novel member of the immunoglobulin gene superfamily, upon programmed cell death, The EMBO Journal, 1992, 11(11):3887-3895, Oxford University Press.
Freeman, G. J. et al., Engagement of the PD-1 Immunoinhibitory Receptor by a Novel B7 Family Member Leads to Negative Regulation of Lymphocyte Activation, J. Exp. Med., Oct. 2, 2000, 192(7):1027-1034, The Rockefeller University Press.
Latchman, Y. et al., PD-L2 is a second ligand for PD-1 and inhibits T cell activation, Nature Immunology, Mar. 2001, 2(3):261-268, 2001 Nature Publishing Group.
Greenwald, R. J. et al., The B7 Family Revisited, Annu. Rev. Immunol., Jan. 2005, 23:515- 548, 2005 Annual Reviews.
Okazaki, T. et al., The PD-1-PD-L pathway in immunological tolerance, TRENDS in Immunology, Apr. 2006, 27(4):195-202, 2006 Elsevier Ltd.
Yao, S. et al., PD-1 on dendritic cells impedes innate immunity against bacterial infection, Immunobiology, Jun. 4, 2009, 113(23):5811-5819, 2009 The American Society of Hematology.
Prokunina, L. et al., A regulatory polymorphism in PDCD1 is associated with susceptibility to systemic lupus erythematosus in humans, Nature Genetics, Dec. 2002, 32:666-669, 2002 Nature Publishing Group.
Lin, S.C. et al., Association of a Programmed Death 1 Gene Polymorphism With the Development of Rheumatoid Arthritis, but Not Systemic Lupus Erythematosus, Arthritis & Rheumatism, Mar. 2004, 50(3):770-775, 2004 American College of Rheumatology.

Jurado, J. O. et al., Programmed Death (PD) −1:PD-Ligand 1/PD-Ligand 2 Pathway Inhibits T Cell Effector Functions during Human Tuberculosis, The Journal of Immunology, 2008, 181:116-125, 2008 The American Association of Immunologists, Inc.
Day, C. L. et al., PD-1 expression on HIV-specific T cells is associated with T-cell exhaustion and disease progression, Nature, Sep. 21, 2006, 443:350-354, 2006 Nature Publishing Group.
Urbani, S. et al., PD-1 Expression in Acute Hepatitis C Virus (HCV) Infection Is Associated with HCV-Specific CD8 Exhaustion, Journal of Virology, Nov. 2006, 80(22):11398-11403, 2006 American Society for Microbiology.
Wan, B. et al., Aberrant Regulation of Synovial T Cell Activation by Soluble Costimulatory Molecules in Rheumatoid Arthritis, The Journal of Immunology, 2006, 177:8844-8850, 2006 The American Association of Immunologists, Inc.
Liu, S. M. et al, Overexpression of the CTLA-4 Isoform Lacking Exons 2 and 3 Causes Autoimmunity, The Journal of Immunology, 2012, 188:155-162, 2011 The American Association of Immunologists, Inc.
Magistrelli, G. et al., Identification of Three Alternatively Spliced Variants of Human CD28 mRNA, Biochemical and Biophysical Research Communications, Apr. 20, 1999, 259(1):34-37, 1999 Academic Press.
Hanawa, H. et al., A novel costimulatory signaling in human T lymphocytes by a splice variant of CD28, Immunobiology, Mar. 15, 2002, 99(6):2138-2146, 2002 The American Society of Hematology.
Matlin, A. J. et al., Understanding Alternative Splicing: Towards a Cellular Code, Nature Reviews Molecular Cell Biology, May 2005, 6:386-398.
Thanaraj, T. A. et al., Human GC-AG alternative intron isoforms with weak donor sites show enhanced consensus at acceptor exon positions, Nucleic Acids Research, May 1, 2001, 29(12):2581-2593, 2001 Oxford University Press.
Joffre, O. et al., Inflammatory signals in dendritic cell activation and the induction of adaptive immunity, Immunological Reviews, 2009, 227:234-247, 2009 The Authors Journal Compilation, 2009 Blackwell Munksgaard.
Aihara, H. et al., Gene transfer into muscle by electroporation in vivo, Nature Biotechnology, Sep. 1998, 16: 867-870, 1998 Nature Publishing Group.
Davis, M. R. et al., Establishment of a Murine Model of Malignant Mesothelioma, Int. J. Cancer, Jul. 27, 1992, 52:881-886, 1992 Wiley-Liss, Inc.
Giorelli, M. et al., IFN-βa Modulates the Expression of CTLA-4 and CD28 Splice Variants in Human Mononuclear Cells: Induction of Soluble Isoforms, Journal of Interferon and Cytokine Research, May 25, 2001, 21:809-812, Mary Ann Liebert, Inc.
Hebbar, M. et al., Detection of circulating soluble CD28 in patients with systemic lupus erythematosus, primary Sjögren's syndrome and systemic sclerosis, Clin Exp Immunol, Feb. 2, 2004, 136:388-392, 2004 Blackwell Publishing Ltd.
Wong, C. K. et al., Aberrant production of soluble costimulatory molecules CTLA-4, CD28, CD80 and CD86 in patients with systemic lupus erythematosus, Rheumatology, May 3, 2005, 44:989-994, Advance Access Publication, The Author 2005, Oxford University Press.
Wang, H. et al., Plasma sCD28, sCTLA-4 levels in neuromyelitis optica and multiple sclerosis during relapse, Journal of Neuroimmunology, 2012, 243:52-55, 2011 Elsevier B.V.
Koup, R. A. et al., Vaccine Design for CD8 T Lymphocyte Responses, Cold Spring Harbor Perspectives in Medicine, 2011, pp. 1-15, 2011 Cold Spring Harbor Laboratory Press.
Chen, Z. et al., Design, Construction, and Characterization of a Multigenic Modified Vaccinia Ankara Candidate Vaccine Against Human Immunodeficiency Virus Type 1 Subtype C/B', J Acquir Immune Defic Syndr, Apr. 1, 2008, 47(4):412-421, 2008 Lippincott Williams & Wilkins.
Huang, Y. et al., Design, Construction, and Characterization of a Dual-Promoter Multigenic DNA Vaccine Directed Against an HIV-1 Subtype C/B' Recombinant, J Acquir Immune Defic Syndr, Apr. 1, 2008, 47(4):403-411, 2008 Lippincott Williams & Wilkins.

(56) References Cited

OTHER PUBLICATIONS

Li, Z. et al., Novel Vaccination Protocol with Two Live Mucosal Vectors Elicits Strong Cell-Mediated Immunity in the Vagina and Protects against Vaginal Virus Challenge, The Journal of Immunology, 2008, 180:2504-2513, 2008 The American Association of Immunologists, Inc.

Dai, B. et al., HIV-1 Gag-specific immunity induced by a lentivector-based vaccine directed to dendritic cells, PNAS, Dec. 1, 2009, 106(48):20382-20387.

Roake, J. A. et al., Dendritic Cell Loss from Nonlymphoid Tissues after Systemic Administration of Lipopolysaccharide, Tumor Necrosis Factor, and Interleukin 1, J. Exp. Med., Jun. 1995, 181:2237-2247, The Rockefeller University Press.

Trevejo, J. M. et al., TNF-α-dependent maturation of local dendritic cells is critical for activating the adaptive immune response to virus infection, PNAS, Oct. 9, 2001, 98(21):12162-12167.

De Jong, E. C. et al., Microbial Compounds Selectively Induce Th1 Cell-Promoting or Th2 Cell-Promoting Dendritic Cells in Vitro with Diverse Th Cell-Polarizing Signals, The Journal of Immunology, 2002, 168:1704-1709, 2002 The American Association of Immunologists, Inc.

Klagge, I. M. et al., Impact of measles virus dendritic-cell infection on Th-cell polarization in vitro, Journal of General Virology, Jul. 21, 2004, 85:3239-3247, 2004 SGM.

Kuhweide, R. et al., Tumor necrosis factor-α and interleukin 6 synergistically induce T cell growth, Cytokines and T Cell Activation, Eur. J. Immunol., 1990, 20:1019-1025, VCH Verlagsgesellschaft mbH, D-6940 Weinheim, 1990.

Detournay, O. et al., IL-6 Produced by Type I IFN DC Controls IFN-γ Production by Regulating the Suppressive Effect of CD4+ CD25+ Regulatory T Cells, Human Immunology, Jan. 7, 2005, 66:460-468, American Society for Histocompatibility and Immunogenetics, 2005, Elsevier Inc.

Kim, J. J. et al., Development of a multicomponent candidate vaccine for HIV-1, Vaccine, 1997, 15(8):879-883, 1997 Elsevier Science Ltd.

Agadjanyan, M. G. et al., CD86 (B7-2) Can Function to Drive Mhc-Restricted Antigen-Specific CTL Responses in Vivo, The Journal of Immunology, 1999, 162:3417-3427, 1999 The American Association of Immunologists, Inc.

Shedlock, D. J. et al., DNA vaccination: antigen presentation and the induction of immunity, Journal of Leukocyte Biology, Dec. 2000, 68(6):793-806, 2000 Society for Leukocyte Biology.

Hirao, L. A. et al., Combined effects of IL-12 and electroporation enhances the potency of DNA vaccination in macaques, Vaccine, Jun. 13, 2008, 26(25):3112-3120, 2008 Elsevier Ltd.

Ontiveros, F. et al., Type I interferon supports primary CD8+ T-cell responses to peptide-pulsed dendritic cells in the absence of CD4+ T-cell help, Immunology, Nov. 30, 2010, 132:549-558, 2011 The Authors. Immunology, 2011 Blackwell Publishing Ltd.

Oh, S. et al., IL-15 as a mediator of CD4+ help for CD8+ T cell longevity and avoidance of TRAIL-mediated apoptosis, PNAS, Apr. 1, 2008, 105(13):5201-5206, 2008 The National Academy of Sciences of the USA.

Rossum, A. V. et al., Inflammatory Cytokines Determine the Susceptibility of Human CD8 T Cells to Fas-mediated Activation-induced Cell Death through Modulation of FasL and c-FLIP$_s$ Expression, The Journal of Biological Chemistry, Jun. 17, 2011, 286(24):21137-21144, 2011 The American Society for Biochemistry and Molecular Biology, Inc.

Wüthrich, M. et al., Vaccine Immunity to Pathogenic Fungi Overcomes the Requirement for CD4 Help in Exogenous Antigen Presentation to CD8+ T Cells: Implications for Vaccine Development in Immune-deficient Hosts, The Journal of Experimental Medicine, Jun. 2, 2003, 197(11):1405-1416, The Rockefeller University Press.

Onlamoon, N. et al., Soluble PD-1 rescues the proliferative response of simian immunodeficiency virus-specific CD4 and CD8 T cells during chronic infection, Immunology, Oct. 25, 2007, 124:277-293, 2008 The Authors Journal compilation, 2008 Blackwell Publishing Ltd.

Akira, S. et al., Toll-Like Receptor Signalling, Nature Reviews Immunology, Jul. 2004, 4:499-511.

Andersson, U. et al., HMGB1 Is a Therapeutic Target for Sterile Inflammation and Infection, Annu Rev Immunol., 2011, vol. 29, pp. 1-34.

Apetoh, L. et al., Toll-like receptor 4-dependent contribution of the immune system to anticancer chemotherapy and radiotherapy, Nature Medicine, Sep. 2007, 13(9):1050-1059, 2007 Nature Publishing Group.

Bacon, C. M. et al., Interleukin 12 induces tyrosine phosphorylation and activation of STAT4 in human lymphocytes, Proc. Natl. Acad. Sci. USA., Aug. 1995, 92:7307-7311.

Bieback, K. et al., Expansion of human γ/δ T cells in vitro is differentially regulated by the measles virus glycoproteins, Journal of General Virology, Jan. 22, 2003, 84:1179-1188, 2003 SGM.

Brandes, M. et al., Professional Antigen-Presentation Function by Human γδ T Cells, Science, Jul. 8, 2005, 309(5732):264-268, The American Association for the Advancement of Science, The Authors.

Brandes, M. et al., Cross-presenting human γδ T cells induce robust CD8+ αβ T cell responses, PNAS, Feb. 17, 2009, 106(7):2307-2312, 2009 The National Academy of Sciences of the USA.

Brenchley, J. M. et al., The mucosal barrier and immune activation in HIV pathogenesis, Curr Opin HIV AIDS, May 2008, vol. 3, No. 3, pp. 1-10, 2008 Wolters Kluwer Health, Lippincott Williams & Wilkins.

Cairns, B. et al., Increased Toll-Like Receptor 4 Expression on T Cells May Be a Mechanism for Enhanced T cell Response Late After Burn Injury, The Journal of TRAUMA® Injury, Infection, and Critical Care, Apr. 25, 2006, 61(2):293-299, 2006 Lippincott Williams & Wilkins, Inc.

Caramalho, I. et al., Regulatory T Cells Selectively Express Toll-like Receptors and Are Activated by Lipopolysaccharide, The Journal of Experimental Medicine, Feb. 17, 2003, 197(4):403-411, The Rockefeller University Press.

Cheung, A. K. L. et al., Viral gene expression during the establishment of human cytomegalovirus latent infection in myeloid progenitor cells, Hematopoiesis, Dec. 1, 2006, 108(12):3691-3699, 2006 The American Society of Hematology.

Eberl, M. et al., Microbial isoprenoid biosynthesis and human γδ T cell activation, FEBS Letters, Apr. 17, 2003, 544:4-10, 2003 Elsevier Science B.V.

Evans, P. S. et al., In vitro stimulation with a non-peptidic alkylphosphate expands cells expressing Vγ2-Jγ1.2/Vδ2 T-cell receptors, Immunology, May 17, 2001, 104:19-27, 2001 Blackwell Science Ltd.

Gober, H.J. et al., Human T Cell Receptor γδ Cells Recognize Endogenous Mevalonate Metabolites in Tumor Cells, The Journal of Experimental Medicine, Jan. 20, 2003, 197(2):163168, The Rockefeller University Press.

Kabelitz, D., Expression and function of Toll-like receptors in T lymphocytes, Current Opinion in Immunology, 2007, 19:39-45, 2006 Elsevier Ltd.

Kang, Y. et al., CCR5 Antagonist TD-0680 Uses a Novel Mechanism for Enhanced Potency against HIV-1 Entry, Cell-mediated Infection, and a Resistant Variant, J. Biol. Chem., 2012, pp. 1-24, 2012 The American Society for Biochemistry and Molecular Biology, Inc.

Kapsenberg, M. L., Dendritic-Cell Control of Pathogen-Driven T-Cell Polarization, Nature Reviews Immunology, Dec. 2003, 3:984-993.

Kato, H. et al., Differential roles of Mdas and RIG-I helicases in the recognition of RNA viruses, Letters, Nature, May 4, 2006, 441:101-105, 2006 Nature Publishing Group.

Kim, S. et al., Signaling of High Mobility Group Box 1 (HMGB1) through Toll-like Receptor 4 in Macrophages Requires CD14, Molecular Medicine, Mar. 11, 2013, 19:88-98.

Li, W. et al., Effect of IL-18 on Expansion of γδ T Cells Stimulated by Zoledronate and IL-2, Journal of Immunotherapy, Apr. 2010, 33(3):287-296, 2010 Lippincott Williams & Wilkins.

(56) References Cited

OTHER PUBLICATIONS

Lu, X. et al., F18, a Novel Small-Molecule Nonnucleoside Reverse Transcriptase Inhibitor, Inhibits HIV-1 Replication Using Distinct Binding Motifs as Demonstrated by Resistance Selection and Docking Analysis, Antimicrobial Agents and Chemotherapy, Oct. 18, 2011, pp. 341-351, 2012 American Society for Microbiology.

Meuter, S. et al., Prolonged antigen survival and cytosolic export in cross-presenting human γσ T cells, PNAS, May 11, 2010, 107(19):8730-8735.

Mogensen, T. H. et al., Molecular Pathways in Virus-Induced Cytokine Production, Microbiology and Molecular Biology Reviews, Mar. 2001, 65(1):131-150, 2001 American Society for Microbiology.

Moser, B. et al., γσ T cells: novel initiators of adaptive immunity, Immunological Reviews, 2007, 215:89-102, 2007 The Authors Journal Compilation, 2007 Blackwell Munksaard.

Muul, L. M. et al., Measurement of Proliferative Responses of Cultured Lymphocytes, Current Protocols in Immunology, Aug. 2008, 82:7.10.1-7.10.24, 2008 John Wiley & Sons, Inc.

Nishimura, H. et al., IL-15 is a novel growth factor for murine gamma delta T cells induced by *Salmonella* infection, The Journal of Immunology, 1996, 156:663-669, 1996 The American Association of Immunologists, Inc.

Pichyangkul, S. et al., Activation of γσ T Cells in Malaria: Interaction of Cytokines and a Schizont-Associated *Plasmodium falciparum* Antigen, The Journal of Infectious Diseases, Jul. 1997, 176:233-241.

Poles, M. A. et al., Human Immunodeficiency Virus Type 1 Induces Persistent Changes in Mucosal and Blood γσ T Cells despite Suppressive Therapy, Journal of Virology, Oct. 2003, 77(19):10456-10467, 2003 American Society for Microbiology.

Rauser, G. et al., Rapid generation of combined CMV-specific $CD4^+$ and $CD8^+$ T-cell lines for adoptive transfer into recipients of allogeneic stem cell transplants, Transplantation, May 1, 2004, 103(9):3565-3572, 2004 The American Society of Hematology.

Reynolds, J. M. et al., Toll-like receptor 4 signaling in T cells promotes autoimmune inflammation, PNAS, Aug. 7, 2012, 109(32):13064-13069.

Rossol, M. et al., LPS-Induced Cytokine Production in Human Monocytes and Macrophages, *Critical Reviews™ in Immunology*, 2011, 31(5):379-446, 2011 Begell House, Inc.

Schneider, C. A. et al., NIH Image to ImageJ: 25 years of image analysis, Nature Methods, Jul. 2012, 9(7):671-675, 2012 Nature America, Inc.

Scotet, E. et al., Bridging innate and adaptive immunity through γσ T-dendritic cell crosstalk, Frontiers in Bioscience, May 1, 2008, 13:6872-6885.

Shimazu, R. et al., MD-2, a Molecule that Confers Lipopolysaccharide Responsiveness on Toll-like Receptor 4, Journal of Experimental Medicine, Jun. 7, 1999, 189(11):1777-1782, The Rockefeller University Press.

Skeen, M. J. et al., Activation of gamma delta T cells for production of IFN-gamma is mediated by bacteria via macrophage-derived cytokines IL-1 and IL-12, The Journal of Immunology, 1995, 154:5832-5841, 1995 The American Association of Immunologists, Inc.

Tanaka, Y. et al., Nonpeptide ligands for human γσ T cells, Proc. Natl. Acad. Sci. USA., Aug. 1994, 91:8175-8179.

Ueta, C. et al., Interleukin-12 activates human γσ T cells: synergistic effect of tumor necrosis factor-α, Eur. J. Immunol., Sep. 20, 1996, 26:3066-3073, VCH Verlagsgesellschaft mbH, D-69451, Weinheim, 1996.

Vermijlen, D. et al., Distinct Cytokine-Driven Responses of Activated Blood γσ T Cells: Insights into Unconventional T Cell Pleiotropy1, J. Immunol., Apr. 1, 2007, 178(7):1-21, 2007 The American Association of Immunologists.

Yang, H. et al., A critical cysteine is required for HMGB1 binding to Toll-like receptor 4 and activation of macrophage cytokine release, PNAS, Jun. 29, 2010, 107(26):11942-11947.

Yang, Z. et al., Inhibition of STAT4 Activation by Lisofylline Is Associated with the Protection of Autoimmune Diabetes, Ann. N.Y. Acad. Sci., 2003, 1005:409-411, 2003 New York Academy of Sciences.

Ye, D. et al., Toll-like receptor-4 mediates obesity-induced non-alcoholic steatohepatitis through activation of X-box binding protein-1 in mice, Hepatology, Dec. 13, 2011, 61:1058-1067, *Gut* 2012.

Zhou, J. et al., PD1-based DNA vaccine amplifies HIV-1 GAG-specific $CD8^+$ T cells in mice, The Jounral of Clinical Investigation, Jun. 2013, 123(6):2629-2642.

Zhou, J. et al., Potentiating Functional Antigen-specific $CD8^+$ T Cell Immunity by a Novel PD1 Isoform-based Fusion DNA Vaccine, Molecular Therapy, Jul. 2013, 21(7):1445-1455, The American Society of Gene & Cell Therapy.

Zou, W. et al., Inhibitory B7-family molecules in the tumour microenvironment, Nature Reviews, Immunology, Jun. 2008, 8:467-477, 2008 Nature Publishing Group.

\* cited by examiner

Nucleotides sequences

Soluble PD1: (SEQ ID NO: 19)

```
ATGCAGATCCCACAGGCGCCCTGGCCAGTCGTCTGGGCGGTGCTACAACTGGGCTGGCGGCCAGGATGGT
TCTTAGACTCCCCAGACAGGCCCTGGAACCCCCCACCTTCTCCCCAGCCCTGCTCGTGGTGACCGAAGG
GGACAACGCCACCTTCACCTGCAGCTTCTCCAACACATCGGAGAGCTTCGTGCTAAACTGGTACCGCATG
AGCCCCAGCAACCAGACGGACAAGCTGGCCGCCTTCCCCGAGGACCGCAGCCAGCCCGGCCAGGACTGCC
GCTTCCGTGTCACACAACTGCCCAACGGGCGTGACTTCCACATGAGCGTGGTCAGGGCCCGGCGCAATGA
CAGCGGCACCTACCTCTGTGGGGCCATCTCCCTGGCCCCCAAGACGCAGATCAAAGAGAGCCTGCGGGCA
GAGCTCAGGGTGACAGAGAGAAGGGCAGAAGTGCCCACAGCCCACCCCAGCCCCTCACCCAGGCCAGCCG
                                GCCAG
```

Soluble Δ42PD1: (SEQ ID NO:20)

```
ATGCAGATCCCACAGGCGCCCTGGCCAGTCGTCTGGGCGGTGCTACAACTGGGCTGGCGGCCAGGATGGT
TCTTAGCCCTGCTCGTGGTGACCGAAGGGGACAACGCCACCTTCACCTGCAGCTTCTCCAACACATCGGA
GAGCTTCGTGCTAAACTGGTACCGCATGAGCCCCAGCAACCAGACGGACAAGCTGGCCGCCTTCCCCGAG
GACCGCAGCCAGCCCGGCCAGGACTGCCGCTTCCGTGTCACACAACTGCCCAACGGGCGTGACTTCCACA
TGAGCGTGGTCAGGGCCCGGCGCAATGACAGCGGCACCTACCTCTGTGGGGCCATCTCCCTGGCCCCCAA
GACGCAGATCAAAGAGAGCCTGCGGGCAGAGCTCAGGGTGACAGAGAGAAGGGCAGAAGTGCCCACAGCC
                     CACCCCAGCCCCTCACCCAGGCCAGCCGGCCAG
```

Amino acid sequences:

Soluble PD1: (SEQ ID NO:21)

MQIPQAPWPVVWAVLQLGWRPGWFLDSPDRPWNPPTFFPALLVVTEGDNATFTCSFSNTSESFVLNWYRM
SPSNQTDKLAAFPEDRSQPGQDCRFRVTQLPNGRDFHMSVVRARRNDSGTYLCGAISLAPKTQIKESLRA
                       ELRVTERRAEVPTAHPSPSRPAGQ

Soluble Δ42PD1: (SEQ ID NO: 22)

MQIPQAPWPVVWAVLQLGWRPGWFLALLVVTEGDNATFTCSFSNTSESFVLNWYRMSPSNQTDKLAAFPE
DRSQPGQDCRFRVTQLPNGRDFHMSVVRARRNDSGTYLCGAISLAPKTQIKESLRAELRVTERRAEVPTA
                              HPSPSRPAGQ

FIG. 18

SEQUENCE LISTING

```
<160> NUMBER OF SEQ ID NOS: 78

<210> SEQ ID NO 1
<211> LENGTH: 274
<212> TYPE: PRT
<213> ORGANISM: Homo sapiens

<400> SEQUENCE: 1
```

Met Gln Ile Pro Gln Ala Pro Trp Pro Val Val Trp Ala Val Leu Gln
1               5                   10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Phe Gln Thr Leu Val Val Gly Val Val
145                 150                 155                 160

Gly Gly Leu Leu Gly Ser Leu Val Leu Leu Val Trp Val Leu Ala Val
                165                 170                 175

Ile Cys Ser Arg Ala Ala Arg Gly Thr Ile Gly Ala Arg Arg Thr Gly
            180                 185                 190

Gln Pro Leu Lys Glu Asp Pro Ser Ala Val Pro Val Phe Ser Val Asp
        195                 200                 205

```
Tyr Gly Glu Leu Asp Phe Gln Trp Arg Glu Lys Thr Pro Glu Pro
    210                 215                 220
Val Pro Cys Val Pro Glu Gln Thr Glu Tyr Ala Thr Ile Val Phe Pro
225             230                 235                 240
Ser Gly Met Gly Thr Ser Ser Pro Ala Arg Arg Gly Ser Ala Asp Gly
                245                 250                 255
Pro Arg Ser Ala Gln Pro Leu Arg Pro Glu Asp Gly His Cys Ser Trp
            260                 265                 270
Pro Leu
```

<210> SEQ ID NO 2
<211> LENGTH: 288
<212> TYPE: PRT
<213> ORGANISM: Homo sapiens

<400> SEQUENCE: 2

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
                20                  25                  30
Asn Pro Pro Thr Phe Ser Pro Ala Leu Leu Val Val Thr Glu Gly Asp
                35                  40                  45
Asn Ala Thr Phe Thr Cys Ser Phe Ser Asn Thr Ser Glu Ser Phe Val
50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
                100                 105                 110
Ala Arg Arg Asn Asp Ser Gly Thr Tyr Leu Cys Gly Ala Ile Ser Leu
            115                 120                 125
Ala Pro Lys Ala Gln Ile Lys Glu Ser Leu Arg Ala Glu Leu Arg Val
130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285
```

<210> SEQ ID NO 3

```
<211> LENGTH: 14
<212> TYPE: PRT
<213> ORGANISM: Homo sapiens

<400> SEQUENCE: 3

Asp Ser Pro Asp Arg Pro Trp Asn Pro Pro Thr Phe Ser Pro
1               5                   10

<210> SEQ ID NO 4
<211> LENGTH: 9
<212> TYPE: PRT
<213> ORGANISM: Homo sapiens

<400> SEQUENCE: 4

Gly Gly Gly Gly Ser Gly Gly Gly Gly
1               5

<210> SEQ ID NO 5
<211> LENGTH: 21
<212> TYPE: PRT
<213> ORGANISM: Homo sapiens

<400> SEQUENCE: 5

Gly Gly Thr Gly Gly Thr Gly Gly Thr Thr Cys Ala Gly Gly Ala Gly
1               5                   10                  15

Gly Ala Gly Gly Ala
            20

<210> SEQ ID NO 6
<211> LENGTH: 9
<212> TYPE: PRT
<213> ORGANISM: Homo sapiens

<400> SEQUENCE: 6

Ala Met Gln Met Leu Lys Asp Thr Ile
1               5

<210> SEQ ID NO 7
<211> LENGTH: 20
<212> TYPE: PRT
<213> ORGANISM: Homo sapiens

<400> SEQUENCE: 7

Thr Ser Asn Pro Pro Ile Pro Val Gly Asp Ile Tyr Lys Arg Trp Ile
1               5                   10                  15

Ile Leu Gly Leu
            20

<210> SEQ ID NO 8
<211> LENGTH: 9
<212> TYPE: PRT
<213> ORGANISM: Homo sapiens

<400> SEQUENCE: 8

Gly Gly Gly Gly Gly Gly Gly Gly Gly
1               5

<210> SEQ ID NO 9
<211> LENGTH: 9
<212> TYPE: PRT
<213> ORGANISM: Homo sapiens

<400> SEQUENCE: 9

Glu Glu Glu Glu Glu Glu Glu Glu Glu
```

```
1               5

<210> SEQ ID NO 10
<211> LENGTH: 9
<212> TYPE: PRT
<213> ORGANISM: Homo sapiens

<400> SEQUENCE: 10

Ser Ser Ser Ser Ser Ser Ser Ser Ser
1               5

<210> SEQ ID NO 11
<211> LENGTH: 9
<212> TYPE: PRT
<213> ORGANISM: Homo sapiens

<400> SEQUENCE: 11

Gly Gly Gly Gly Gly Cys Pro Pro Cys
1               5

<210> SEQ ID NO 12
<211> LENGTH: 7
<212> TYPE: PRT
<213> ORGANISM: Homo sapiens

<400> SEQUENCE: 12

Gly Gly Gly Gly Ser Ser Ser
1               5

<210> SEQ ID NO 13
<211> LENGTH: 13
<212> TYPE: PRT
<213> ORGANISM: Homo sapiens

<400> SEQUENCE: 13

Ser Cys Val Pro Leu Met Arg Cys Gly Gly Cys Cys Asn
1               5                   10

<210> SEQ ID NO 14
<211> LENGTH: 14
<212> TYPE: PRT
<213> ORGANISM: Homo sapiens

<400> SEQUENCE: 14

Pro Ser Cys Val Pro Leu Met Arg Cys Gly Gly Cys Cys Asn
1               5                   10

<210> SEQ ID NO 15
<211> LENGTH: 9
<212> TYPE: PRT
<213> ORGANISM: Homo sapiens

<400> SEQUENCE: 15

Gly Asp Leu Ile Tyr Arg Asn Gln Leu
1               5

<210> SEQ ID NO 16
<211> LENGTH: 23
<212> TYPE: PRT
<213> ORGANISM: Homo sapiens

<400> SEQUENCE: 16

Gly Gly Gly Gly Gly Gly Gly Gly Gly Pro Ser Cys Val Pro Leu Met
1               5                   10                  15
```

Arg Cys Gly Gly Cys Cys Asn
            20

<210> SEQ ID NO 17
<211> LENGTH: 6
<212> TYPE: PRT
<213> ORGANISM: Homo sapiens

<400> SEQUENCE: 17

Ala Gly Phe Cys Cys Cys
1               5

<210> SEQ ID NO 18
<211> LENGTH: 42
<212> TYPE: PRT
<213> ORGANISM: Homo sapiens

<400> SEQUENCE: 18

Ala Cys Thr Cys Cys Cys Cys Ala Gly Ala Cys Ala Gly Gly Cys Cys
1               5                   10                  15

Cys Thr Gly Gly Ala Ala Cys Cys Cys Cys Cys Cys Ala Cys Cys
            20                  25                  30

Thr Thr Cys Thr Thr Cys Cys Cys Ala Gly
        35                  40

<210> SEQ ID NO 19
<211> LENGTH: 495
<212> TYPE: DNA
<213> ORGANISM: Homo sapiens

<400> SEQUENCE: 19
atgcagatcc cacaggcgcc ctggccagtc gtctgggcgg tgctacaact gggctggcgg      60
ccaggatggt tcttagactc cccagacagg ccctggaacc ccccacctt ctccccagcc     120 ctgctcgtgg tgaccgaagg ggacaacgcc accttcacct gcagcttctc caacacatcg    180
gagagcttcg tgctaaactg gtaccgcatg agccccagca ccagacggaa caagctggcc    240
gccttccccg aggaccgcag ccagcccggc caggactgcc gcttccgtgt cacacaactg    300
cccaacgggc gtgacttcca catgagcgtg gtcagggccg gcgcaatga cagcggcacc    360 tacctctgtg gggccatctc cctggccccc aaggcgcaga tcaaagagag cctgcgggca    420
gagctcaggg tgacagagag aagggcagaa gtgcccacag cccaccccag cccctcaccc    480
aggccagccg gccag                                                      495

<210> SEQ ID NO 20
<211> LENGTH: 453
<212> TYPE: DNA
<213> ORGANISM: Homo sapiens

<400> SEQUENCE: 20
atgcagatcc cacaggcgcc ctggccagtc gtctgggcgg tgctacaact gggctggcgg      60
ccaggatggt tcttagccct gctcgtggtg accgaagggg acaacgccac cttcacctgc    120
agcttctcca acacatcgga gagcttcgtg ctaaactggt accgcatgag ccccagcaac    180
cagacggaca agctggccgc cttccccgag gaccgcagcc agcccggcca ggactgccgc    240
ttccgtgtca cacaactgcc caacgggcgt gacttccaca tgagcgtggt cagggcccgg    300
cgcaatgaca gcggcaccta cctctgtggg gccatctccc tggcccccaa ggcgcagatc    360
aaagagagcc tgcgggcaga gctcagggtg acagagagaa gggcagaagt gcccacagcc    420 cacccagcc cctcacccag gccagccggc cag 453

<210> SEQ ID NO 21
<211> LENGTH: 165
<212> TYPE: PRT
<213> ORGANISM: Homo sapiens

<400> SEQUENCE: 21

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Thr Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln
                165

<210> SEQ ID NO 22
<211> LENGTH: 151
<212> TYPE: PRT
<213> ORGANISM: Homo sapiens

<400> SEQUENCE: 22

Met Gln Ile Pro Gln Ala Pro Trp Pro Val Val Trp Ala Val Leu Gln
1               5                   10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Thr Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln

<210> SEQ ID NO 23
<211> LENGTH: 825
<212> TYPE: DNA
<213> ORGANISM: Homo sapiens

<400> SEQUENCE: 23

```
atgcagatcc cacaggcgcc ctggccagtc gtctgggcgg tgctacaact gggctggcgg      60
ccaggatggt tcttagccct gctcgtggtg accgaagggg acaacgccac cttcacctgc     120
agcttctcca cacatcgga gagcttcgtg ctaaactggt accgcatgag ccccagcaac     180
cagacggaca agctggccgc cttccccgag gaccgcagcc agcccggcca ggactgccgc     240
ttccgtgtca cacaactgcc caacgggcgt gacttccaca tgagcgtggt cagggcccgg     300
cgcaatgaca gcggcaccta cctctgtggg gccatctccc tggcccccaa ggcgcagatc     360
aaagagagcc tgcgggcaga gctcagggtg acagagagaa gggcagaagt gcccacagcc     420
cacccccagcc cctcacccag gccagccggc cagttccaaa ccctggtggt tggtgtcgtg     480
ggcggcctgc tgggcagcct ggtgctgcta gtctgggtcc tggccgtcat ctgctcccgg     540
gccgcacgag gacaataggg agccaggcgc accggccagc cctgaaggga ggaccccctca    600
gccgtgcctg tgttctctgt ggactatggg gagctggatt ccagtggcg agagaagacc      660
ccggagcccc ccgtgccctg tgtccctgag cagacggagt atgccaccat tgtctttcct     720
agcggaatgg gcacctcatc ccccgcccgc aggggctcag ctgacggccc tcggagtgcc     780
cagccactga ggcctgagga tggacactgc tcttggcccc tctga                      825
```

<210> SEQ ID NO 24
<211> LENGTH: 867
<212> TYPE: DNA
<213> ORGANISM: Homo sapiens

<400> SEQUENCE: 24

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccacccag ccctcacccc      480
aggccagccg ccagttcca aaccctggtg gttggtgtcg tgggcggcct gctgggcagc     540
ctggtgctgc tagtctgggt cctggccgtc atctgctccc gggccgcacg aggacaata     600
ggagccaggc gcaccggcca gccctgaag gaggaccccct cagccgtgcc tgtgttctct    660
gtggactatg gggagctgga tttccagtgg cgagagaaga ccccggagcc cccgtgccc     720
tgtgtccctg agcagacgga gtatgccacc attgtctttc tagcggaatg ggcacctca     780
tccccgcccc gcagggctc agctgacggc cctcggagtg cccagccact gaggcctgag     840
gatggacact gctcttggcc cctctga                                          867
```

<210> SEQ ID NO 25
<211> LENGTH: 453

<212> TYPE: DNA
<213> ORGANISM: Homo sapiens

<400> SEQUENCE: 25

```
atgcagatcc cacaggcgcc ctggccagtc gtctgggcgg tgctacaact gggctggcgg      60
ccaggatggt tcttagccct gctcgtggtg accgaagggg acaacgccac cttcacctgc     120
agcttctcca acacatcgga gagcttcgtg ctaaactggt accgcatgag ccccagcaac     180
cagacggaca agctggccgc cttccccgag accgcagcc agcccggcca ggactgccgc      240
ttccgtgtca cacaactgcc caacgggcgt gacttccaca tgagcgtggt cagggcccgg     300
cgcaatgaca gcggcaccta cctctgtggg gccatctccc tggcccccaa ggcgcagatc     360
aaagagagcc tgcgggcaga gctcagggtg acagagagaa gggcagaagt gcccacagcc     420
cacccccagcc cctcacccag gccagccggc cag                                  453
```

<210> SEQ ID NO 26
<211> LENGTH: 156
<212> TYPE: PRT
<213> ORGANISM: Homo sapiens

<400> SEQUENCE: 26

```
Met Gln Ile Pro Gln Ala Pro Trp Pro Val Val Trp Ala Val Leu Gln
  1               5                  10                  15
Leu Gly Trp Arg Pro Gly Trp Phe Leu Ala Leu Leu Val Val Thr Glu
             20                  25                  30
Gly Asp Asn Ala Thr Phe Thr Cys Ser Phe Ser Asn Thr Ser Glu Ser
         35                  40                  45
Phe Val Leu Asn Trp Tyr Arg Met Ser Pro Ser Asn Gln Thr Asp Lys
     50                  55                  60
Leu Ala Ala Phe Pro Glu Asp Arg Ser Gln Pro Gly Gln Asp Cys Arg
 65                  70                  75                  80
Phe Arg Val Thr Gln Leu Pro Asn Gly Arg Asp Phe His Met Ser Val
                 85                  90                  95
Val Arg Ala Arg Arg Asn Asp Ser Gly Thr Tyr Leu Cys Gly Ala Ile
            100                 105                 110
Ser Leu Ala Pro Lys Ala Gln Ile Lys Glu Ser Leu Arg Ala Glu Leu
        115                 120                 125
Arg Val Thr Glu Arg Arg Ala Glu Val Pro Thr Ala His Pro Ser Pro
    130                 135                 140
Ser Pro Arg Pro Ala Gly Gln Phe Gln Thr Leu Val
145                 150                 155
```

<210> SEQ ID NO 27
<211> LENGTH: 1176
<212> TYPE: DNA
<213> ORGANISM: Homo sapiens

<400> SEQUENCE: 27

```
atgcagatcc cacaggcgcc ctggccagtc gtctgggcgg tgctacaact gggctggcgg      60
ccaggatggt tcttagccct gctcgtggtg accgaagggg acaacgccac cttcacctgc     120
agcttctcca acacatcgga gagcttcgtg ctaaactggt accgcatgag ccccagcaac     180
cagacggaca agctggccgc cttccccgag accgcagcc agcccggcca ggactgccgc      240
ttccgtgtca cacaactgcc caacgggcgt gacttccaca tgagcgtggt cagggcccgg     300
cgcaatgaca gcggcaccta cctctgtggg gccatctccc tggcccccaa ggcgcagatc     360
```

| | | |
|---|---|---|
| aaagagagcc tgcgggcaga gctcaggggtg acagagagaa gggcagaagt gcccacagcc | 420 | |
| caccccagcc cctcacccag gccagccggc cagctcgagg ccaccaacac caaagtggac | 480 | |
| aagaccgttg cgccctcgac atgcagcaag cccatgtgcc caccccctga actcctgggg | 540 | |
| ggaccgtctg tcttcatctt cccccaaaa cccaaggaca ccctcatgat ctcacgcacc | 600 | |
| cccgaggtca catgcgtggt ggtggacgtg agccaggatg accccgaggt gcagttcaca | 660 | |
| tggtacataa caacgagca ggtgcgcacc gccggccgc cgctacggga gcagcagttc | 720 | |
| aacagcacga tccgcgtggt cagcaccctc cccatcgcgc accaggactg gctgaggggc | 780 | |
| aaggagttca gtgcaaagt ccacaacaag gcactcccgg cccccatcga aaaaccatc | 840 | |
| tccaaagcca gagggcagcc cctggagccg aaggtctaca ccatgggccc tccccgggag | 900 | |
| gagctgagca gcaggtcggt cagcctgacc tgcatgatca cggcttcta cccttccgac | 960 | |
| atctcggtgg agtgggagaa gaacgggaag gcagaggaca actacaagac cacgccgacc | 1020 | |
| gtgctggaca gcgacggctc ctacttcctc tacagcaagc tctcagtgcc cacgagtgag | 1080 | |
| tggcagcggg gcgacgtctt cacctgctcc gtgatgcacg aggccttgca caaccactac | 1140 | |
| acgcagaagt ccatctccca ctctcctggt aaataa | 1176 | |

<210> SEQ ID NO 28
<211> LENGTH: 391
<212> TYPE: PRT
<213> ORGANISM: Homo sapiens

<400> SEQUENCE: 28

```
Met Gln Ile Pro Gln Ala Pro Trp Pro Val Val Trp Ala Val Leu Gln
1               5                   10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Leu Glu Ala Thr Asn Thr Lys Val Asp
145                 150                 155                 160

Lys Thr Val Ala Pro Ser Thr Cys Ser Lys Pro Met Cys Pro Pro Pro
                165                 170                 175

Glu Leu Leu Gly Gly Pro Ser Val Phe Ile Phe Pro Pro Lys Pro Lys
            180                 185                 190

Asp Thr Leu Met Ile Ser Arg Thr Pro Glu Val Thr Cys Val Val Val
        195                 200                 205

Asp Val Ser Gln Asp Asp Pro Glu Val Gln Phe Thr Trp Tyr Ile Asn
    210                 215                 220

Asn Glu Gln Val Arg Thr Ala Arg Pro Pro Leu Arg Glu Gln Gln Phe
```

```
                225                 230                 235                 240
Asn Ser Thr Ile Arg Val Val Ser Thr Leu Pro Ile Ala His Gln Asp
                    245                 250                 255

Trp Leu Arg Gly Lys Glu Phe Lys Cys Lys Val His Asn Lys Ala Leu
                260                 265                 270

Pro Ala Pro Ile Glu Lys Thr Ile Ser Lys Ala Arg Gly Gln Pro Leu
            275                 280                 285

Glu Pro Lys Val Tyr Thr Met Gly Pro Pro Arg Glu Glu Leu Ser Ser
        290                 295                 300

Arg Ser Val Ser Leu Thr Cys Met Ile Asn Gly Phe Tyr Pro Ser Asp
305                 310                 315                 320

Ile Ser Val Glu Trp Glu Lys Asn Gly Lys Ala Glu Asp Asn Tyr Lys
                325                 330                 335

Thr Thr Pro Thr Val Leu Asp Ser Asp Gly Ser Tyr Phe Leu Tyr Ser
            340                 345                 350

Lys Leu Ser Val Pro Thr Ser Glu Trp Gln Arg Gly Asp Val Phe Thr
        355                 360                 365

Cys Ser Val Met His Glu Ala Leu His Asn His Tyr Thr Gln Lys Ser
370                 375                 380

Ile Ser His Ser Pro Gly Lys
385                 390

<210> SEQ ID NO 29
<211> LENGTH: 157
<212> TYPE: PRT
<213> ORGANISM: Homo sapiens

<400> SEQUENCE: 29

Met Gln Ile Pro Gln Ala Pro Trp Pro Val Val Trp Ala Val Leu Gln
1               5                   10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln His His His His His
145                 150                 155

<210> SEQ ID NO 30
<211> LENGTH: 30
<212> TYPE: PRT
<213> ORGANISM: Homo sapiens

<400> SEQUENCE: 30

Leu Leu Val Val Thr Glu Gly Asp Asn Ala Thr Phe Thr Cys Ser Phe
```

```
                1               5              10              15
Ser Asn Thr Ser Glu Ser Phe Val Leu Asn Trp Tyr Arg Met
            20              25              30
```

<210> SEQ ID NO 31
<211> LENGTH: 30
<212> TYPE: PRT
<213> ORGANISM: Homo sapiens

<400> SEQUENCE: 31

```
Glu Ser Phe Val Leu Asn Trp Tyr Arg Met Ser Pro Ser Asn Gln Thr
1               5                  10                  15
Asp Lys Leu Ala Ala Phe Pro Glu Asp Arg Ser Gln Pro Gly
            20                  25                  30
```

<210> SEQ ID NO 32
<211> LENGTH: 30
<212> TYPE: PRT
<213> ORGANISM: Homo sapiens

<400> SEQUENCE: 32

```
Ala Phe Pro Glu Asp Arg Ser Gln Pro Gly Gln Asp Cys Arg Phe Arg
1               5                  10                  15
Val Thr Gln Leu Pro Asn Gly Arg Asp Phe His Met Ser Val
            20                  25                  30
```

<210> SEQ ID NO 33
<211> LENGTH: 30
<212> TYPE: PRT
<213> ORGANISM: Homo sapiens

<400> SEQUENCE: 33

```
Pro Asn Gly Arg Asp Phe His Met Ser Val Val Arg Ala Arg Arg Asn
1               5                  10                  15
Asp Ser Gly Thr Tyr Leu Cys Gly Ala Ile Ser Leu Ala Pro
            20                  25                  30
```

<210> SEQ ID NO 34
<211> LENGTH: 30
<212> TYPE: PRT
<213> ORGANISM: Homo sapiens

<400> SEQUENCE: 34

```
Tyr Leu Cys Gly Ala Ile Ser Leu Ala Pro Lys Ala Gln Ile Lys Glu
1               5                  10                  15
Ser Leu Arg Ala Glu Leu Arg Val Thr Glu Arg Arg Ala Glu
            20                  25                  30
```

<210> SEQ ID NO 35
<211> LENGTH: 30
<212> TYPE: PRT
<213> ORGANISM: Homo sapiens

<400> SEQUENCE: 35

```
Glu Leu Arg Val Thr Glu Arg Arg Ala Glu Val Pro Thr Ala His Pro
1               5                  10                  15
Ser Pro Ser Pro Arg Pro Ala Gly Gln Phe Gln Thr Leu Val
            20                  25                  30
```

<210> SEQ ID NO 36
<211> LENGTH: 22
<212> TYPE: DNA

```
<213> ORGANISM: Homo sapiens

<400> SEQUENCE: 36
gcagtggaga aggcggcact ct                                              22

<210> SEQ ID NO 37
<211> LENGTH: 25
<212> TYPE: DNA
<213> ORGANISM: Homo sapiens

<400> SEQUENCE: 37
cttctcctga ggaaatgcgc tgacc                                           25

<210> SEQ ID NO 38
<211> LENGTH: 25
<212> TYPE: DNA
<213> ORGANISM: Homo sapiens

<400> SEQUENCE: 38
agggcattcc agaaagatga ggata                                           25

<210> SEQ ID NO 39
<211> LENGTH: 22
<212> TYPE: DNA
<213> ORGANISM: Homo sapiens

<400> SEQUENCE: 39
cccgatgaac ccctaaacca ca                                              22

<210> SEQ ID NO 40
<211> LENGTH: 25
<212> TYPE: DNA
<213> ORGANISM: Homo sapiens

<400> SEQUENCE: 40
gagctgtggc aagtcctcat atcaa                                           25

<210> SEQ ID NO 41
<211> LENGTH: 22
<212> TYPE: DNA
<213> ORGANISM: Homo sapiens

<400> SEQUENCE: 41
gcagtggaga aggcggcact ct                                              22

<210> SEQ ID NO 42
<211> LENGTH: 35
<212> TYPE: DNA
<213> ORGANISM: Homo sapiens

<400> SEQUENCE: 42
gcagaggccc cagcagagac ttctcaatga cattc                                35

<210> SEQ ID NO 43
<211> LENGTH: 35
<212> TYPE: DNA
<213> ORGANISM: Homo sapiens

<400> SEQUENCE: 43
tgcttccaga gctagaggac agagatgccg gtcac                                35

<210> SEQ ID NO 44
<211> LENGTH: 25
```

```
<212> TYPE: DNA
<213> ORGANISM: Homo sapiens

<400> SEQUENCE: 44
agtcgtctgg gcggtgctac aactg                                    25

<210> SEQ ID NO 45
<211> LENGTH: 25
<212> TYPE: DNA
<213> ORGANISM: Homo sapiens

<400> SEQUENCE: 45
gctggggtgg gctgtgggca cttct                                    25

<210> SEQ ID NO 46
<211> LENGTH: 22
<212> TYPE: DNA
<213> ORGANISM: Homo sapiens

<400> SEQUENCE: 46
cggccaggat ggttcttagc cc                                       22

<210> SEQ ID NO 47
<211> LENGTH: 18
<212> TYPE: DNA
<213> ORGANISM: Homo sapiens

<400> SEQUENCE: 47
cagacaggcc ctggaacc                                            18

<210> SEQ ID NO 48
<211> LENGTH: 20
<212> TYPE: DNA
<213> ORGANISM: Homo sapiens

<400> SEQUENCE: 48
agcttgtccg tctggttgct                                          20

<210> SEQ ID NO 49
<211> LENGTH: 60
<212> TYPE: DNA
<213> ORGANISM: Homo sapiens

<400> SEQUENCE: 49
cggccgcggc ggcggcggcg gccgccgcgg cggcggcggc cgccctgctg ctggtgaccg    60

<210> SEQ ID NO 50
<211> LENGTH: 60
<212> TYPE: DNA
<213> ORGANISM: Homo sapiens

<400> SEQUENCE: 50
cggccgccgc cgccgcggcg gccgccgccg ccgccgcggc cgctaagaac catcctggcc    60

<210> SEQ ID NO 51
<211> LENGTH: 25
<212> TYPE: DNA
<213> ORGANISM: Homo sapiens

<400> SEQUENCE: 51
agggcattcc agaaagatga ggata                                    25

<210> SEQ ID NO 52
```

```
<211> LENGTH: 20
<212> TYPE: DNA
<213> ORGANISM: Homo sapiens

<400> SEQUENCE: 52
ccaagttgga tgggtcctgg                                               20

<210> SEQ ID NO 53
<211> LENGTH: 25
<212> TYPE: DNA
<213> ORGANISM: Homo sapiens

<400> SEQUENCE: 53
gagctgtggc aagtcctcat atcaa                                         25

<210> SEQ ID NO 54
<211> LENGTH: 20
<212> TYPE: DNA
<213> ORGANISM: Homo sapiens

<400> SEQUENCE: 54
ccaagttgga tgggtcctgg                                               20

<210> SEQ ID NO 55
<211> LENGTH: 22
<212> TYPE: DNA
<213> ORGANISM: Homo sapiens

<400> SEQUENCE: 55
gcagtggaga aggcggcact ct                                            22

<210> SEQ ID NO 56
<211> LENGTH: 20
<212> TYPE: DNA
<213> ORGANISM: Homo sapiens

<400> SEQUENCE: 56
ctggccggct ggcctgggtg                                               20

<210> SEQ ID NO 57
<211> LENGTH: 21
<212> TYPE: DNA
<213> ORGANISM: Homo sapiens

<400> SEQUENCE: 57
ccgaggcagt cagatcatct t                                             21

<210> SEQ ID NO 58
<211> LENGTH: 18
<212> TYPE: DNA
<213> ORGANISM: Homo sapiens

<400> SEQUENCE: 58
agctgcccct cagcttga                                                 18

<210> SEQ ID NO 59
<211> LENGTH: 21
<212> TYPE: DNA
<213> ORGANISM: Homo sapiens

<400> SEQUENCE: 59
ggtacatcct cgacggcatc t                                             21
```

<210> SEQ ID NO 60
<211> LENGTH: 21
<212> TYPE: DNA
<213> ORGANISM: Homo sapiens

<400> SEQUENCE: 60
gtgcctcttt gctgctttca c                                             21

<210> SEQ ID NO 61
<211> LENGTH: 20
<212> TYPE: DNA
<213> ORGANISM: Homo sapiens

<400> SEQUENCE: 61
aagctgatgg ccctaaacag                                               20

<210> SEQ ID NO 62
<211> LENGTH: 20
<212> TYPE: DNA
<213> ORGANISM: Homo sapiens

<400> SEQUENCE: 62
aggtgcatcg tgcacataag                                               20

<210> SEQ ID NO 63
<211> LENGTH: 20
<212> TYPE: DNA
<213> ORGANISM: Homo sapiens

<400> SEQUENCE: 63
agctgaagca gttccagaag                                               20

<210> SEQ ID NO 64
<211> LENGTH: 20
<212> TYPE: DNA
<213> ORGANISM: Homo sapiens

<400> SEQUENCE: 64
agtctcattc cagccagtgc                                               20

<210> SEQ ID NO 65
<211> LENGTH: 20
<212> TYPE: DNA
<213> ORGANISM: Homo sapiens

<400> SEQUENCE: 65
ggacatcatc aaacctgacc                                               20

<210> SEQ ID NO 66
<211> LENGTH: 20
<212> TYPE: DNA
<213> ORGANISM: Homo sapiens

<400> SEQUENCE: 66
agggagaagt aggaatgtgg                                               20

<210> SEQ ID NO 67
<211> LENGTH: 20
<212> TYPE: DNA
<213> ORGANISM: Homo sapiens

<400> SEQUENCE: 67
gcagggcttc ctaaaacaga                                               20

```
<210> SEQ ID NO 68
<211> LENGTH: 21
<212> TYPE: DNA
<213> ORGANISM: Homo sapiens

<400> SEQUENCE: 68
gttgtttgct aggatgatca g                                              21

<210> SEQ ID NO 69
<211> LENGTH: 21
<212> TYPE: DNA
<213> ORGANISM: Homo sapiens

<400> SEQUENCE: 69
acagtccatg ccatcactgc c                                              21

<210> SEQ ID NO 70
<211> LENGTH: 21
<212> TYPE: DNA
<213> ORGANISM: Homo sapiens

<400> SEQUENCE: 70
gcctgcttca ccaccttctt g                                              21

<210> SEQ ID NO 71
<211> LENGTH: 25
<212> TYPE: DNA
<213> ORGANISM: Mus musculus

<400> SEQUENCE: 71
catcttctca aaattcgagt gacaa                                          25

<210> SEQ ID NO 72
<211> LENGTH: 23
<212> TYPE: DNA
<213> ORGANISM: Mus musculus

<400> SEQUENCE: 72
tgggagtaga caaggtacaa ccc                                            23

<210> SEQ ID NO 73
<211> LENGTH: 22
<212> TYPE: DNA
<213> ORGANISM: Mus musculus

<400> SEQUENCE: 73
gtagctatgg tactccagag ac                                             22

<210> SEQ ID NO 74
<211> LENGTH: 20
<212> TYPE: DNA
<213> ORGANISM: Mus musculus

<400> SEQUENCE: 74
acgatgatgc acttgcagaa                                                20

<210> SEQ ID NO 75
<211> LENGTH: 20
<212> TYPE: DNA
<213> ORGANISM: Mus musculus

<400> SEQUENCE: 75
ttccaggatg aggacatgag                                                20
```

```
<210> SEQ ID NO 76
<211> LENGTH: 20
<212> TYPE: DNA
<213> ORGANISM: Mus musculus

<400> SEQUENCE: 76
ttgttgttca tctcggagcc                                              20

<210> SEQ ID NO 77
<211> LENGTH: 20
<212> TYPE: DNA
<213> ORGANISM: Mus musculus

<400> SEQUENCE: 77
gtgggccgct ctaggcacca                                              20

<210> SEQ ID NO 78
<211> LENGTH: 25
<212> TYPE: DNA
<213> ORGANISM: Mus musculus

<400> SEQUENCE: 78
cggttggcct tagggttcag ggggg                                        25
```

ANTIBODIES AGAINST NOVEL PD1 ISOFORMS AND USES THEREOF

CROSS-REFERENCE TO RELATED APPLICATION

This application claims the benefit of U.S. provisional application Ser. No. 61/808,993, filed Apr. 5, 2013, which is herein incorporated by reference in its entirety.

BACKGROUND

Programmed death-1 (PD1, CD279) is a member of the CD28 superfamily that negatively regulates the function of T cells through interaction with its two native ligands PD-L1 (CD274) and PD-L2 (CD273). PD1 is a type I transmembrane receptor protein composed of a single immunoglobulin (Ig) variable-like domain, a cytoplasmic domain, and two tyrosine-based signaling motifs. The ligands for PD1 are PD-L1 (CD274 or B7-H1) and PD-L2 (CD273 or B7-DC), which are members of the B7 family.

PD-L1 is found expressed on both hematopoietic and non-hematopoietic cells found in immunoprivileged sites including the eye and placenta, and is highly elevated in inflammatory environments. Following activation of an immune response, antigen presenting cells (APCs) and T cells further augment the expression of PD-L1, while PD-L2 expression is only found on activated macrophages and DCs. PD1 is constitutively expressed at low levels on resting T cells and is up-regulated on T cells, natural killer T (NKT) cells, B cells and macrophages upon activation.

The absence of PD1 in mice provides significant resistance against bacterial infection through innate immunity, demonstrating the importance of the regulatory role of PD1 against pathogenic infections. In addition, PD1 plays significant roles in a number of autoimmune diseases, including systemic lupus erythematosus (SLE) and rheumatoid arthritis.

Recent studies have characterized the inhibitory function of the interaction between PD1 and PD-L1/2. With PD1 deficient transgenic mice, CD8$^+$ T cells were found to recognize H-2Ld and proliferate more actively than wildtype cells in response to allogeneic (H-2d) APCs. In addition, PD1 deficient mice develop spontaneous lupus-like disease and cardiomyopathy, indicating that PD1 has the role to control over-activated T cells. This is more evident from a study that found up-regulated PD1 expression on LCMV-specific CD8$^+$ T cells, which directly contributes to the dysfunction of these T cells and correlated with the failure to control viral replication in mice during chronic infection. It has been known that HIV-1-specific T cells in patients are usually poorly functional due to the loss of CD28 co-stimulatory molecule, perforin, and down-regulation of CCR7 and IL-7Rα, which are important molecules for maintenance of memory T cells. One of the reasons for the exhausted T cell function during HIV-1 infection is attained by recent studies showing that PD1 is persistently up-regulated on HIV-1 specific CD4$^+$ and CD8$^+$ T cells that have reduced proliferation, cytokine production, and cytotoxicity.

The role of the PD1/PD-L pathway in chronic infections (*Mycobacterium tuberculosis*, LCMV, HIV-1, HBV and HCV) has been characterized extensively. The high expression of PD1 on pathogen-specific CD8$^+$ T cells results in these cells being functionally "exhausted," leading to the failure of clearing persistent infections. In addition, the blockade of the PD1/PD-L1 pathway in vitro and in vivo with antibody or the soluble form (i.e., only containing extracellular domain) of PD1 is able to rescue the function of these exhausted HIV-1 and HCV specific CD8$^+$ and CD4$^+$ T cells by restoring cytokine production, cell proliferation, and cytolysis.

Progression towards AIDS is markedly correlated with the level of PD1 expression on HIV-1-specific CD8$^+$ T cells and the percentage of cells expressing PD1 with viral load and declining CD4$^+$ counts. In contrast, long-term non-progressors (LTNPs) have significantly lower level of PD1 expression found on HIV-specific memory CD8$^+$ T cells compared to progressors.

Experiments also demonstrated that blockade of the PD1/PD-L1 interaction can reverse the function of these exhausted viral-specific CD8$^+$ T cells, which was further shown in vivo in LCMV chronically infected mice treated with antibodies against PD1/PD-L resulted in LCMV-specific CD8$^+$ T cells with restored proliferation and TNF-α and IFN-γ production that led to reduced viral load. Other studies also found that highly active antiretroviral therapy (HAART) recovered reduced PD1-expressed HIV-1-specific CD8$^+$ T cells, and that blocking of the PD1/PD-L pathway could rescue the function of HIV-1-specific T cells. These findings show the importance of the PD1/PD-L pathway that results in the exhausted state of T cells during HIV-1 chronic infection, and may act as one of the key host factors in modulating immune response to target HIV-1 infected cells.

To date, four PD1 isoforms have been reported from alternatively spliced PD1 mRNA. Apart from one of these variants encoding a soluble form of PD1, the other three spliced variants have no function attributed to them. Nevertheless, their highly induced expression following stimulation of human peripheral blood mononuclear cells (PBMCs) likely suggests an immunoregulatory function, which has been shown for variants of the other CD28 family molecules, such as CTLA-4 and CD28. One isoform of CTLA-4 (1/4CTLA-4) could exacerbate experimental autoimmune encephalomyelitis (EAE) diseases in mice, with significantly increased level of CD4$^+$ T cell proliferation and cytokine production compared to wildtype CTLA-4. Interestingly, over-expression of this variant resulted in the down-regulation of wildtype CTLA-4 on CD4$^+$ T cells. For CD28, four spliced variants were identified from human T cells with differential expression. The CD28i isoform was found expressed on the cell surface where it could associate with CD28 to enhance the co-stimulation capacity via CD28, further illustrating that apart from the conventional identified forms, spliced variants of the CD28 receptor family members could have immunoregulatory functions.

SUMMARY OF THE INVENTION

The present inventors identified and characterized from human healthy PBMC donors a new isoform of PD1 (referred to herein as "Δ42PD1") that lacks a fragment encoded by 42-nucleotides. In one embodiment, Δ42PD1 comprises the nucleotide sequence of SEQ ID NO:23. In one embodiment, Δ42PD1 comprises the amino acid sequence of SEQ ID NO:1. This isoform is distinct from the wildtype PD1 as it does not bind to PD-L1 or PD-L2, and is not recognized by PD1-specific monoclonal antibodies. Like PD1, Δ42PD1 mRNA was found expressed in various immune-related cells.

In one embodiment, the present invention provides PD1 protein isoforms. In one embodiment, the PD1 protein isoform is Δ42PD1, which has an amino acid sequence comprising SEQ ID NO: 1. In one embodiment, the PD1 protein isoforms do not bind to PDL1 or PDL2.

In one embodiment, the PD1 protein isoform has a deletion of 14 amino acids at positions corresponding to amino acids 26-39 of the wild-type PD1 protein having an amino acid sequence of SEQ ID NO:2 and a nucleotide sequence of SEQ ID NO:24. In one embodiment, the 14 amino acid deletion has a sequence that is DSPDRPWN-PPTFSP (SEQ ID NO:3).

In another embodiment, the PD1 protein isoform has non-conservative substitutions at one or more amino acids at positions corresponding to amino acids 26-39 of the wild-type PD1 protein having an amino acid sequence of SEQ ID NO:2. In certain embodiments, the PD1 protein isoform has non-conservative substitutions of 1 to 14 amino acids at positions corresponding to amino acids 26-39 of the wild-type PD1 protein having an amino acid sequence of SEQ ID NO:2. In one embodiment, amino acids 26-39 of the wild-type PD1 protein are DSPDRPWNPPTFPP (SEQ ID NO:3).

Another aspect of the subject invention provides nucleic acid molecules that encode the PD1 proteins of the subject invention. The nucleic acid molecules encompass DNA molecules (e.g. genomic DNA and cDNA) and RNA molecules. In addition, the subject nucleic acid molecules may be single-stranded or double-stranded.

Another aspect of the invention provides PD1 fusion proteins and fusion nucleic acid molecules. In one embodiment, the fusion protein comprises a PD1 protein isoform with an amino acid sequence comprising SEQ ID NO: 1 or a biologically active fragment thereof, and an antigen or peptide. In one embodiment, the fusion nucleic acid molecule comprises a nucleic acid molecule encoding a PD1 protein isoform with an amino acid sequence comprising SEQ ID NO: 1 or a biologically active fragment thereof, and a nucleic acid molecule encoding an antigen or peptide.

In one embodiment, the PD1 nucleic acid molecules of the present invention are formulated into a DNA vaccine formulation.

In one aspect, the soluble form of Δ42PD1 (sΔ42PD1) (having a nucleic acid sequence of SEQ ID NO: 25, and an amino acid sequence of SEQ ID NO: 26) is fused with the rabbit IgG Fc domain, comprising a nucleic acid sequence of SEQ ID NO: 27, and an amino acid sequence of SEQ ID NO: 28, to induce production of cytokines. In another embodiment, sΔ42PD1 is fused with 6×His tag, comprising an amino acid sequence of SEQ ID NO: 29 to induce production of cytokines. In still another embodiment, membrane-bound Δ42PD1 is used to induce production of cytokines Another aspect of the invention provides uses of Δ42PD1 proteins and nucleic acids as immunogens to prepare polyclonal and monoclonal antibodies against human Δ42PD1. In one embodiment, sΔ42PD1 is fused with the rabbit IgG Fc domain (sΔ42PD1Fc), comprising an amino acid sequence of SEQ ID NO: 28 and a nucleotide sequence of SEQ ID NO: 27, and used as an immunogen to inoculate BALB/c mouse for antibody preparation.

In another embodiment, the present invention provides antibodies that bind specifically to Δ42PD1. In some embodiments, the antibody is a monoclonal antibody. In one embodiment, the antibody is CH34. In another embodiment, the antibody is CH101.

In one embodiment, the monoclonal antibody blocks the binding of Δ42PD1 to its unknown receptor. In another embodiment, the monoclonal antibody binds a fragment of Δ42PD1, comprising an amino acid sequence of SEQ ID NO: 31.

Another aspect of the present invention provides the uses of the PD1 protein isoforms (e.g., Δ42PD1), nucleic acid molecules, including cDNA molecules, encoding the PD1 protein isoforms, fusion proteins comprising the PD1 protein isoforms, and/or fusion nucleic acid molecules comprising nucleic acid sequences encoding the PD1 protein isoforms, for induction of the production of cytokines (such as, TNF-α, IL-1, and IL-6) in immune cells.

Another aspect of the present invention provides methods for the prevention, treatment, or amelioration of pathogenic infection and/or cancer. The method comprises administering to a subject in need of such prevention and treatment an effective amount of a PD1 protein isoform of the present invention (such as Δ42PD1 protein), a nucleic acid molecule encoding a PD1 protein isoform (e.g., cDNA) of the present invention (such as Δ42PD1 protein), and/or a fusion protein and/or a fusion nucleic acid molecule of the present invention.

Another aspect of the present invention provides methods for diagnosis of virus infection diseases and autoimmune disorders.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Amino acid sequence alignment of Δ42PD1 (SEQ ID NO:1) and PD1 (GenBank accession number: NM_005018) (SEQ ID NO:2) identified from a representative healthy human PBMC donor. Dashed line represents the 14-amino acid deletion found in Δ42PD1. Signal sequence and the transmembrane region are indicated. IgV domain including the front A'GFCC'C" (SEQ ID NO: 17) β-sheet and the back ABED sheet are highlighted by the arrows. Asterisks show the putative amino acids for ligand interaction. (FIG. 1B) Schematic genomic structure of PD1 with the highlighted location of the exact 42-nucleotide deletion in exon 2. (FIG. 1C) Δ42PD1 and PD1 PCR products were amplified from cDNA clones (upper gel) or PD1 alone from the genomic DNA (lower gel) generated from healthy human PBMCs. Lanes 1-7 in both gels represent PCR results from seven human donors. Lanes 8 and 9 are Δ42PD1 and PD1 positive controls, respectively. Lane M represents DNA molecular weight marker. (FIG. 1D) Relative mRNA expression of Δ42PD1 from subpopulations of PBMCs sorted from five independent healthy blood donors, normalized to housekeeping gene GAPDH and total PBMC samples.

(FIG. 2A) 293T cells transiently transfected to express human PD-L1 or (FIG. 2B) PD-L2, and treated with purified recombinant proteins at series of concentrations –0.5, 2, 5 and 20 μg/ml to investigate binding affinity. The results were analyzed by flow cytometry using a detection antibody against rabbit Fc (shaded) or isotype control (solid line). (FIG. 2C) Plasmids encoding PD1 or Δ42PD1 were stably transfected or untransfected 293A cells, and the detection was determined by flow cytometry with a polyclonal anti-PD1 antibody or three monoclonal anti-PD1 antibodies with clone names indicated on the x-axes. Percentage of cells with positive staining (shaded) is shown with corresponding antibodies and isotype control (solid line). Data are representative of three independent experiments.

(FIG. 3A) Cytokine release profile of human PBMCs culture supernatants treated with purified proteins of rabbit Fc, sPD1$_{fc}$ or sΔ42PD1$_{fc}$ for 24 h. qRT-PCR analysis of human PBMCs after protein treatment for 6 h, 12 h, and 24 h, for (FIG. 3B) TNFα, (FIG. 3C) IL6, and (FIG. 3D) IL1b mRNA expression normalized to GAPDH. LPS served as positive control. Data represents mean±SEM office independent experiments. *P<0.05.

(FIG. 4A) purified CD11c$^+$ BM-DCs from Balb/c mice were treated by purified protein msΔ42PD1-p24$_{fc}$, p24$_{fc}$ or positive control LPS for 24 h. Supernatants were collected to analyze cytokine releasing of TNF-α, IL-6 and IL-1α. Data represent mean±SEM of six independent experiments. *P<0.05. Then Balb/c mice were vaccinated using fusion DNA plasmids (20 μg or 100 μg dose), and p24-specific immune responses generated were measured by (FIG. 4B) ELISA for antibody responses, (FIG. 4C) ELISPOT assay for CD4 specific epitope gag26 and (FIG. 4D) CD8 specific epitope gagAI IFN-γ$^+$ responses, and H-2K$^d$ p24 tetramer staining for specific CD8$^+$ T cell response from splenocytes displayed as scatter plot (n=5) (FIG. 4E). (FIG. 4F) ELISPOT assay was performed on splenocytes using three non-overlapping p24 peptide pools. Data represent means±SEM of at least two independent experiments of three mice per group. *P<0.05, **P<0.01.

FIGS. 5A through 5D show long-term memory responses induced by msΔ42PD1-p24$_{fc}$ vaccination. 30 weeks after immunization, mice were sacrificed to assess long-lived memory response for anti-p24 antibody (FIG. 5A) and CD4 and CD8 IFN-γ$^γ$ Elispots (FIG. 5B). CFSE proliferation assay was performed on CD4$^+$ T (FIG. 5C) and CD8$^+$ T (FIG. 5D) cells from splenocytes from 30 weeks post-vaccinated mice for five days of stimulation with BM-DCs (ratio 1 DC:10 T) and p24 peptide pool plus anti-CD28. Anti-CD3/anti-CD28 stimulation served as positive control. Data represent means±SEM of two independent experiments of three mice per group. *P<0.05.

(FIG. 6A) Effector splenocytes (two weeks post-vaccination) were used for cytotoxicity assay against p24-expressing target AB1-HIV-1-Gag cells at various ratios. Percentage of dead cells was calculated and the dot line showed the background signal of target cells alone. (FIG. 6B) Immunized mice were challenged s.c. by 5×10$^5$ AB1-HIV-1-Gag cells three weeks post-vaccination, tumor images were taken twice a week to detect luciferase intensity and representative images at day 17 post-challenge is shown (FIG. 6C). (FIG. 6D) Protection of immunized mice against intranasal virus challenge three weeks after the final immunization with VTTgagpol and (FIG. 6E) virulent WRgagpol. Virus titer was measured from lung homogenates from mice sacrificed 8 days post-challenge on Vero cell plaque formation. (FIG. 6F) Body weight was measured daily overtime and calculated as percentages compared to day 0 of WRgagpol challenge. Functional assay results show the representative data from two independent experiments. Protection studies were performed from at least five mice in each group and data represent the means±SEM. *P<0.05, P<0.01, *P<0.001.

(FIG. 12A) Schematic representation of fusion DNA plasmid constructs of HIV-1 Gag p24 antigen tagged to rabbit Fc with or without human sΔ42PD1, lead by a tPA signal sequence, under the CMV promoter. (FIG. 12B) Immunization schedule of Balb/c mice receiving three shots of DNA three weeks apart, and immune response generated were assessed two weeks after the final immunization. (FIG. 12C) Western blot analysis of fusion protein expressed from transiently transfected 293T cells. Numbers represent marker band size (kDa). (FIG. 12D) ELISA measuring anti-p24 antibody response for IgG1 and IgG2a from mice sera, and (FIG. 12E) p24-specific CD4$^+$ and CD8$^+$ T cell response by IFN-γ ELISPOT. Data represents the means±SEM of two independent experiments. *P<0.05, ***P<0.001. (FIG. 12F) Western blot analysis of detection of Δ42PD1-GST protein using a polyclonal anti-PD1 antibody, or serum from mouse immunized with sΔ42PD1-p24$_{fc}$.

for 6 h, 12 h and 24 h. Data was generated from the means of splenocytes from five individual Balb/c mice of the same age, and normalized to beta-actin and untreated control (Neg). *P<0.05.

Figure 15:
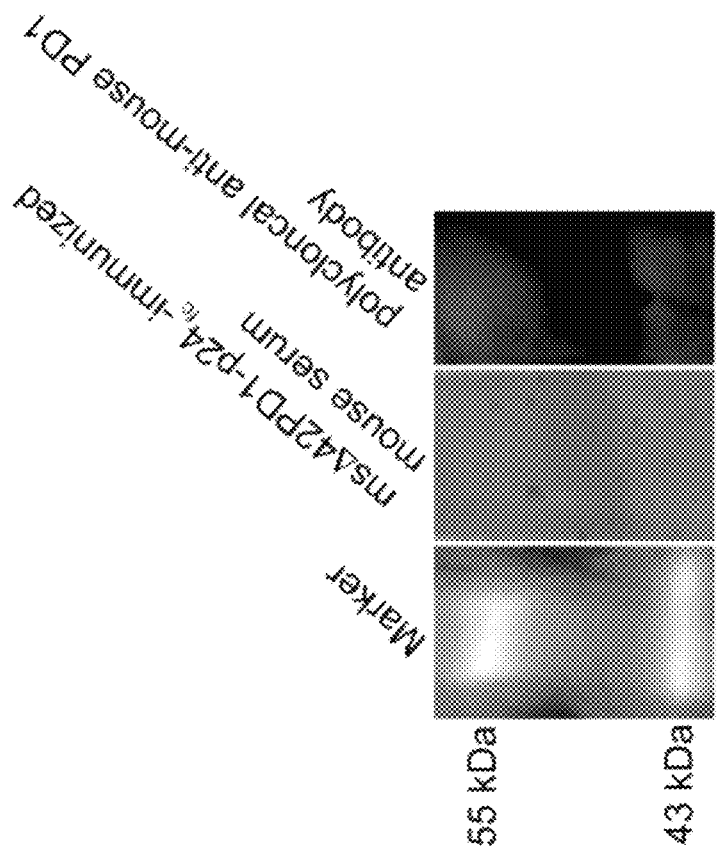

FIG. 15 shows that antibody response against msΔ42PD1 was not found in mice immunized with msΔ42PD1-p24$_{fc}$. Immunized mouse serum was used to detect full-length murine Δ42PD1-GST protein by Western blotting to assess if immune response was raised against msΔ42PD1 in msΔ42PD1-p24$_{fc}$ vaccinated mice. A polyclonal anti-murine PD1 antibody was used as a positive control. Marker band sizes in kDa are shown.

Figure 16:
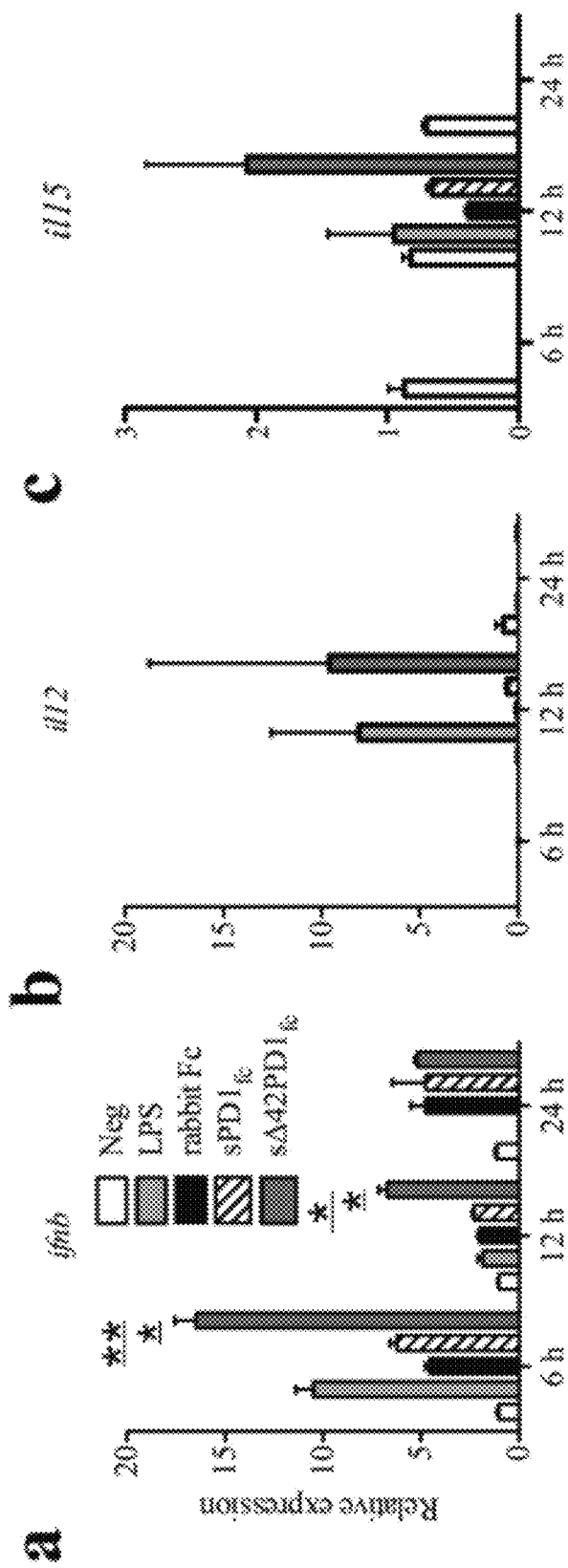

FIGS. 16A through 16C show that induction of T cell-activating cytokines by sΔ42PD1$_{fc}$ in PBMCs. Freshly isolated healthy human PBMCs were treated with sΔ42PD1$_{fc}$, sPD1$_{fc}$, rabbit Fc recombinant proteins, LPS or left untreated. qRT-PCR was performed on total RNA extracted at 6 h, 12 h and 24 h post-treatment to analyze the expression of (FIG. 16A) IFNb, (FIG. 16B) IL12 and (FIG. 16C) IL15 normalized to GAPDH. Induction was seen with sΔ42PD1$_{fc}$ for IL12 and IL15 at 12 h post-treatment but did not reach statistical significance compared to rabbit Fc or sPD1$_{fc}$. However, sΔ42PD1$_{fc}$ induced the expression of IFNb significantly at 6 h and 12 h post-treatment with statistical difference. *P<0.05, **P<0.01.

Figure 17:
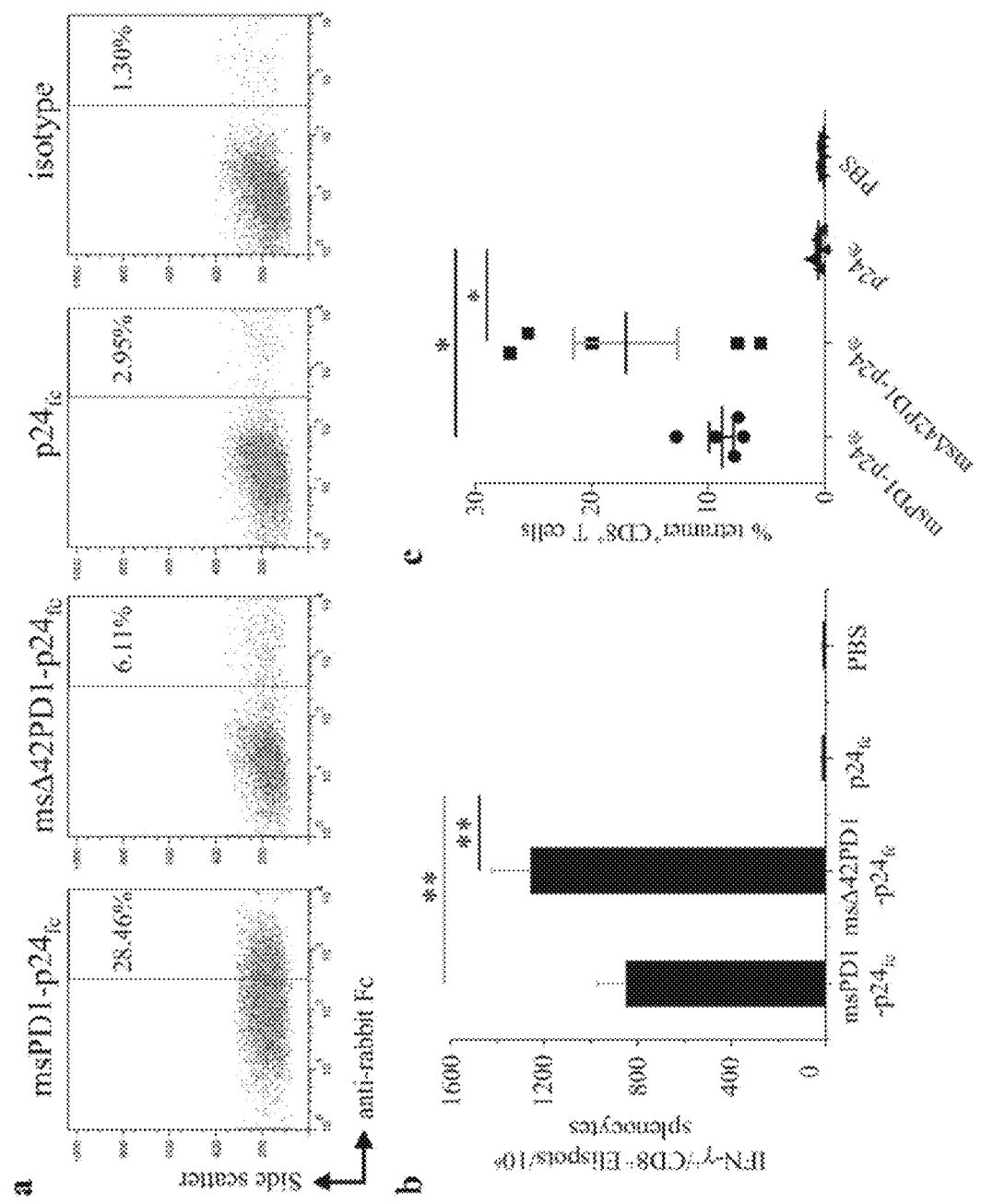

FIGS. 17A through 17C show comparison of wildtype murine sPD1 and sΔ42PD1-based fusion vaccine in mice. (FIG. 17A) To examine binding, recombinant proteins were applied to BM-DCs for 30 min at 4° C. and stained with anti-rabbit Fc or isotype control. Balb/c mice were immunized with 20 μg of msPD1-p24$_{fc}$ or msΔ42PD1-p24$_{fc}$ DNA vaccines, and the CD8$^+$ T cell responses measured by Elispot (FIG. 17B) or tetramer staining (FIG. 17C) are shown. Data represented at least two independent experiments with groups of three mice. *P<0.05, **P<0.0

FIG. 18 shows the nucleic acid sequences and the amino acid sequences of soluble PD1 and soluble Δ42PD1.

FIGS. 19A through 19E show experimental results for the generation of anti-human Δ42PD1 monoclonal antibodies. (FIG. 19A) Timeline and parameters of the electroporation sΔ42PD1fc plasmid DNA prime and sΔ42PD1Fc protein boost regimen in mice was shown with inoculations and bleed to isolate sera for analysis as indicated. (FIG. 19B) Sera of five immunized mice (M1-M5) were analyzed for anti-sΔ42PD1His antibody ELISA titer. Serum of normal mouse (NMS) was used as negative control. (FIGS. 19C and 19D) Sera of immunized mice were analyzed (FIG. 19C) with ELISA for binding potency to sΔ42PD1His and sPD1His proteins, and (FIG. 19D) with FACS for recognizing 293T, 293T-Δ42PD1 and 293T-42PD1 cells. Each symbol represents an individual mouse. Data were presented as mean±standard deviation (S.D.). (FIG. 19E) Supernatants of two monoclonal anti-Δ42PD1 antibodies (clone CH34 and clone CH101) were tested for recognition of Δ42PD1His by ELISA. Plate coated with PBS used as negative control, serum (1:1000) of immunized mouse served as positive control. (FIGS. 19C and 19E) Data were presented as mean±S.D. from three independent experiments.

Figure 20:
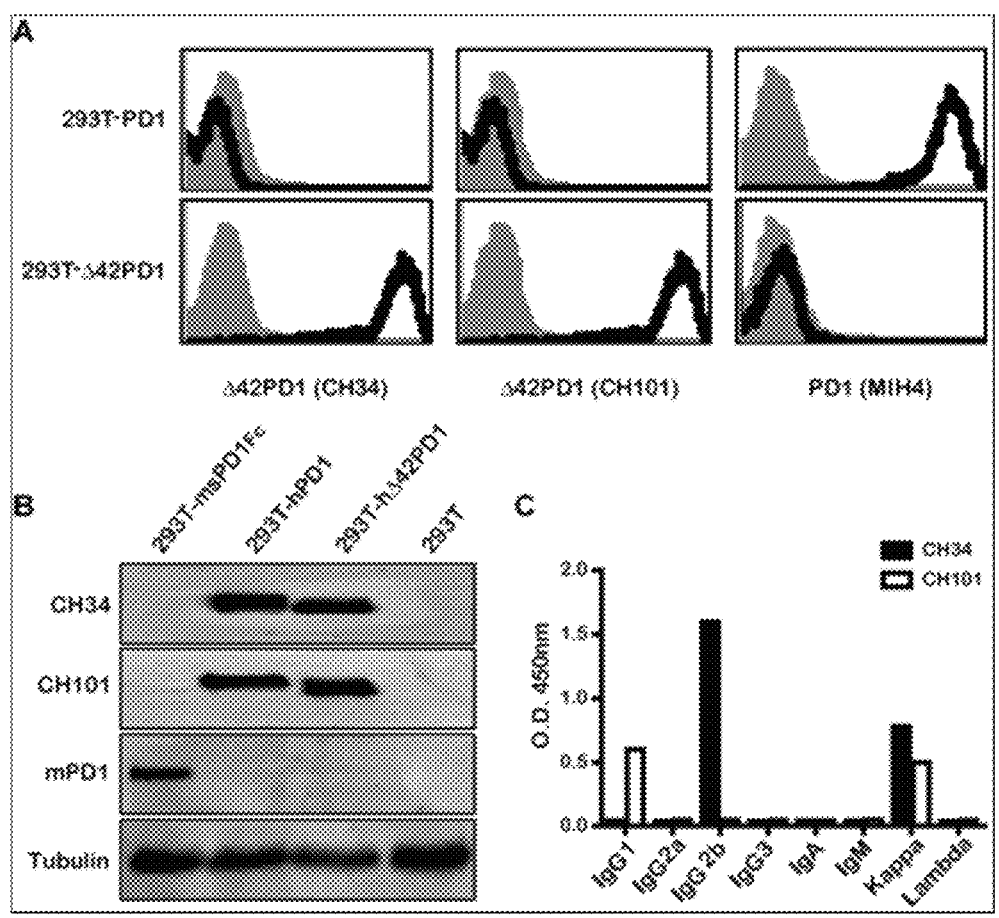

FIGS. 20A through 20C shows the characterization of mouse anti-Human Δ42PD1 monoclonal antibodies. (FIG. 20A) 293T-PD1 cells and 293T-Δ42PD1 cells were stained with anti-human Δ42PD1 mAbs (clone CH34 and CH101) or anti-PD1 mAb (clone MIH4) and analyzed by flow cytometry. 293T cells served as negative control. The plots are representative of at least three independent experiments. (FIG. 20B) Western blot analysis of cell lysates of 293T and indicated 293T transient transfectants using anti-human Δ42PD1 mAbs (clone CH34 and CH101) or anti-mouse PD1 pAb as primarily antibody respectively. Tubulin is shown as loading control. (FIG. 20C) Supernatants of hybridoma clone CH34 and CH101 were analyzed with mouse mAb rapid ELISA isotyping kit.

Figure 21:
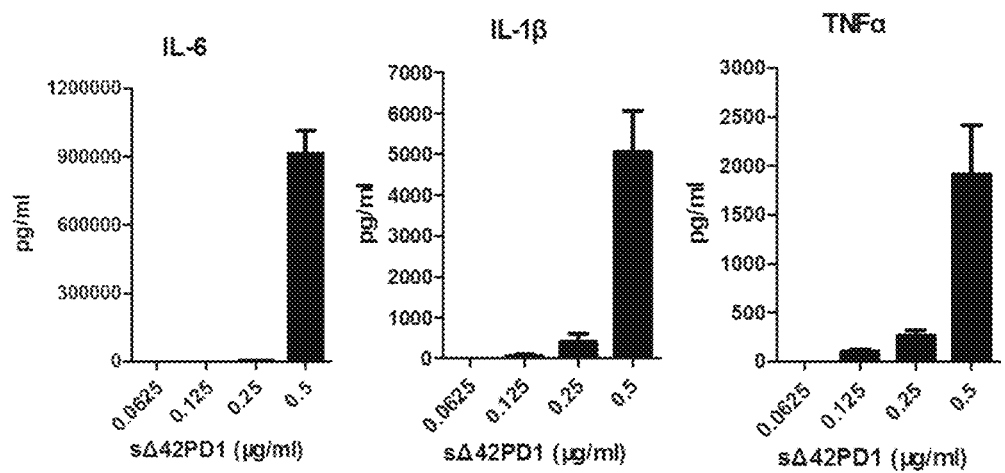

FIG. 21 shows TNFα, IL6, and IL-1 production from human PBMCs induced by recombinant sΔ42PD1 His.

Figure 22:
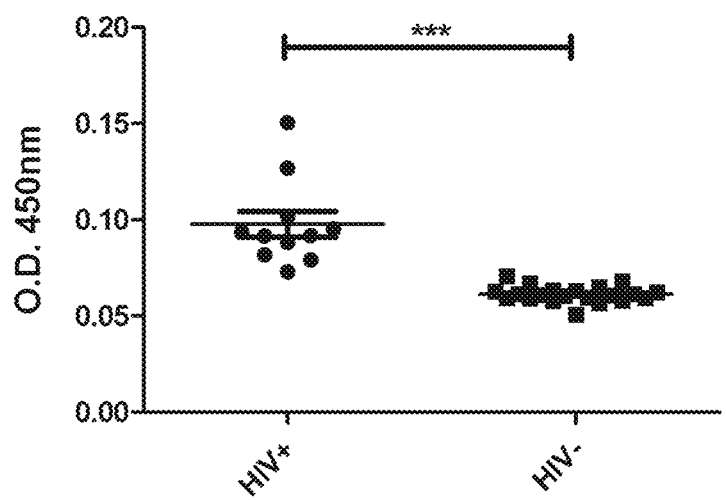

FIG. 22 shows raised sΔ42PD1 level in HIV+ plasma.

Figure 23:
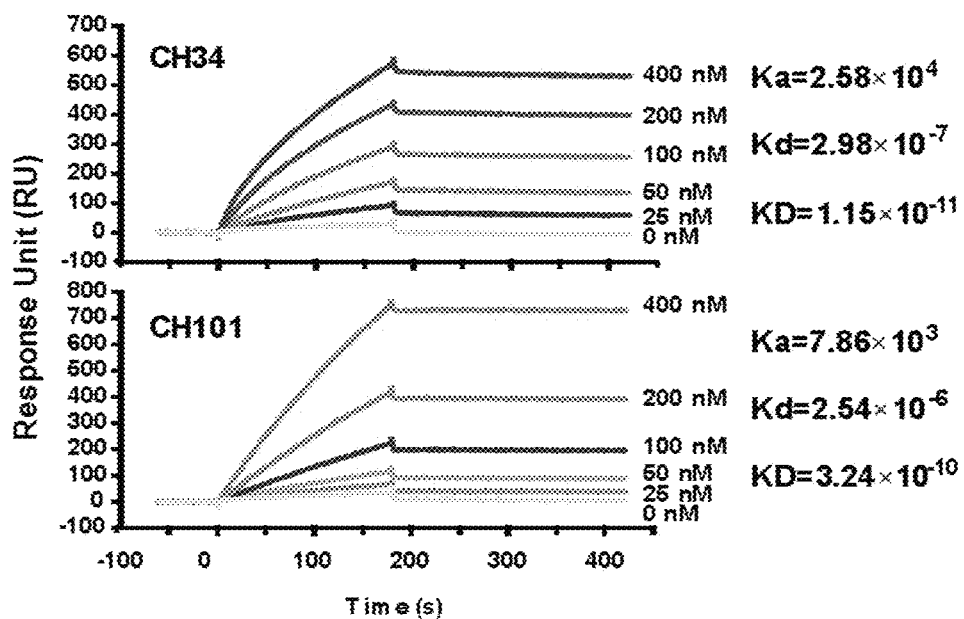

FIG. 23 shows the characterization of anti-Human Δ42PD1 monoclonal antibodies. Both CH34 and CH101 are high affinity antibodies by surface plasmon resonance.

Figure 24:
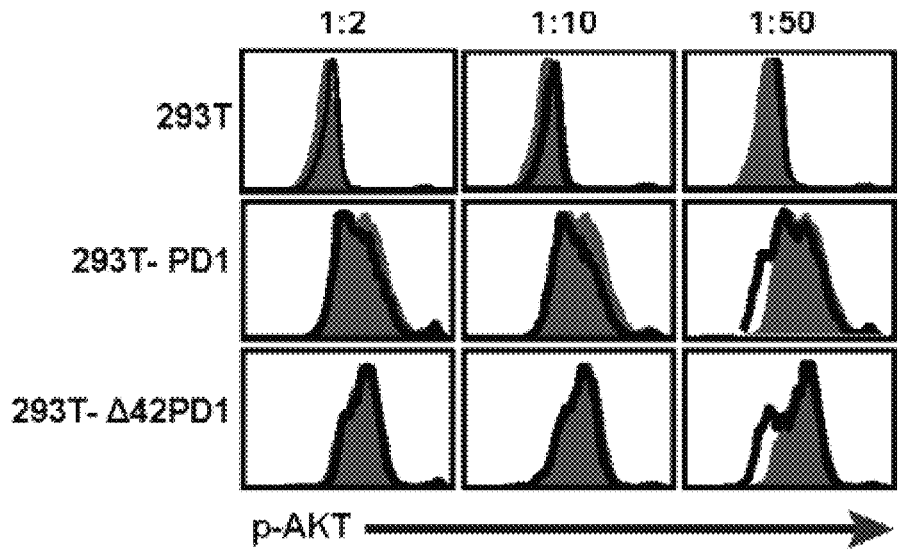

FIG. 24 shows the similar signaling of membrane-bound Δ42PD1 and PD1 to inhibit the Akt signal pathway in Δ42PD1- and PD1-expressing 293T cell lines.

Figure 25:
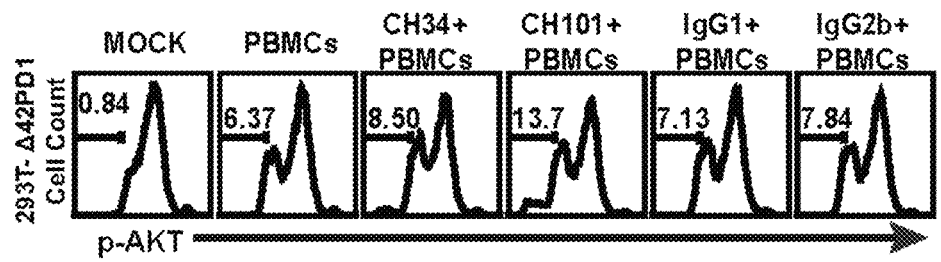

FIG. 25 shows CH101 enhanced Δ42PD1 signaling triggered by Δ42PD1 receptor on PBMCs.

Figure 26:
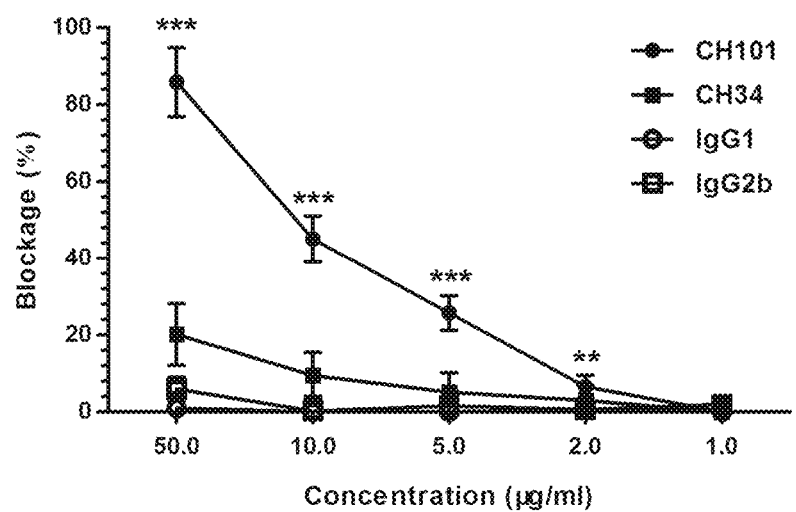

FIG. 26 shows monoclonal antibodies block the binding of recombinant sΔ42PD1$_{Fc}$ protein with the unknown Δ42PD1 receptor on THP-1 cells.

Figure 27:
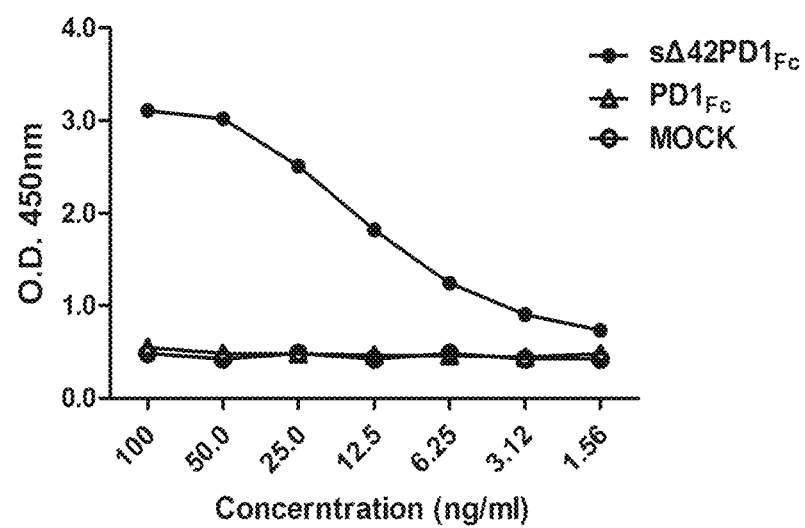

FIG. 27 shows development of a double-antibody sandwich-ELISA for specific detection of sΔ42PD1 in human body fluid.

Figure 28:
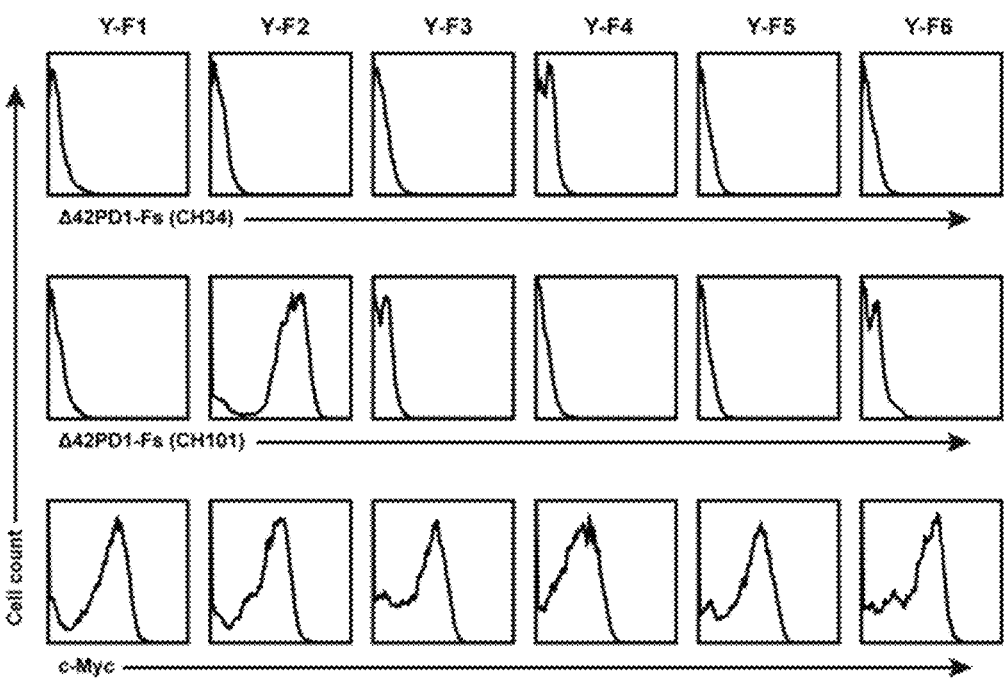

FIGS. 28A and 28B show the binding of mAbs to fragments of sΔ42PD1 displayed on the surface of yeast cells.

BRIEF DESCRIPTION OF THE SEQUENCES

SEQ ID NO:1 is the amino acid sequence of a PD1 protein isoform (Δ42PD1) of the present invention.

SEQ ID NO:2 is the amino acid sequence of a wildtype PD1 protein.

SEQ ID NO:3 is the amino acid sequence of the 14 amino acids deleted from the wildtype PD1 protein of SEQ ID NO:2.

SEQ ID NO:4 is the amino acid sequence of a linker sequence.

SEQ ID NO:5 is the amino acid sequence of a linker sequence.

SEQ ID NO:6 is the amino acid sequence of gagA1.

SEQ ID NO:7 is the amino acid sequence of peptide gag26.

SEQ ID NO:8 is the amino acid sequence of a linker sequence.

SEQ ID NO:9 is the amino acid sequence of a linker sequence.

SEQ ID NO:10 is the amino acid sequence of a linker sequence.

SEQ ID NO:11 is the amino acid sequence of a linker sequence.

SEQ ID NO:12 is the amino acid sequence of a linker sequence.

SEQ ID NO:13 is the amino acid sequence of a linker sequence.

SEQ ID NO:14 is the amino acid sequence of a linker sequence.

SEQ ID NO:15 is the amino acid sequence of a linker sequence.

SEQ ID NO:16 is the amino acid sequence of a linker sequence.

SEQ ID NO:17 is the amino acid sequence of an IgV domain of the PD1 protein.

SEQ ID NO:18 is the nucleic acid sequence encoding the 14 amino acids deleted from the wildtype PD1 protein of SEQ ID NO:2.

SEQ ID NO:19 is a nucleic acid sequence encoding a soluble PD1.

SEQ ID NO:20 is a nucleic acid sequence encoding a soluble ΔPD1.

SEQ ID NO:21 is an amino acid sequence of a soluble PD1.

SEQ ID NO:22 is an amino acid sequence of a soluble ΔPD1.

SEQ ID NO:23 is a nucleic acid sequence of human Δ42PD1.

SEQ ID NO:24 is a nucleic acid sequence of human PD1.

SEQ ID NO:25 is a nucleic acid sequence of human sΔ42PD1.

SEQ ID NO:26 is an amino acid sequence of human sΔ42PD1.

SEQ ID NO:27 is a nucleic acid sequence of sΔ42PD1$_{FC}$.

SEQ ID NO:28 is an amino acid sequence of sΔ42PD1$_{FC}$.

SEQ ID NO:29 is an amino acid sequence of sΔ42PD1$_{His}$.

SEQ ID NO:30 is an amino acid sequence of sΔ42PD1 fragment-1.

SEQ ID NO:31 is an amino acid sequence of sΔ42PD1 fragment-2.

SEQ ID NO:32 is an amino acid sequence of sΔ42PD1 fragment-3.

SEQ ID NO:33 is an amino acid sequence of sΔ42PD1 fragment-4.

SEQ ID NO:34 is an amino acid sequence of sΔ42PD1 fragment-5.

SEQ ID NO:35 is an amino acid sequence of sΔ42PD1 fragment-6.

SEQ ID NO:36 is a nucleic acid sequence of primer PD1 forward.

SEQ ID NO:37 is a nucleic acid sequence of primer PD1 reverse.

SEQ ID NO:38 is a nucleic acid sequence of primer PD-L1 forward.

SEQ ID NO:39 is a nucleic acid sequence of primer PD-L1 reverse.

SEQ ID NO:40 is a nucleic acid sequence of primer PD-L2 forward.

SEQ ID NO:41 is a nucleic acid sequence of primer PD-L2 reverse.

SEQ ID NO:42 is a nucleic acid sequence of primer PD-1D forward.

SEQ ID NO:43 is a nucleic acid sequence of primer PD-1D reverse.

SEQ ID NO:44 is a nucleic acid sequence of primer nPD-1 forward.

SEQ ID NO:45 is a nucleic acid sequence of primer nPD-1 reverse.

SEQ ID NO:46 is a nucleic acid sequence of primer 42PD-1 forward.

SEQ ID NO:47 is a nucleic acid sequence of primer PD-1 forward.

SEQ ID NO:48 is a nucleic acid sequence of primer PD-1 reverse.

SEQ ID NO:49 is a nucleic acid sequence of primer 14aPD-1 forward.

SEQ ID NO:50 is a nucleic acid sequence of primer 14aPD-1 reverse.

SEQ ID NO:51 is a nucleic acid sequence of primer EL1 forward.

SEQ ID NO:52 is a nucleic acid sequence of primer EL1 reverse.

SEQ ID NO:53 is a nucleic acid sequence of primer EL2 forward.

SEQ ID NO:54 is a nucleic acid sequence of primer EL2 reverse.

SEQ ID NO:55 is a nucleic acid sequence of primer ED1 forward.

SEQ ID NO:56 is a nucleic acid sequence of primer ED1 reverse.

SEQ ID NO:57 is a nucleic acid sequence of primer hTNFa-f.

SEQ ID NO:58 is a nucleic acid sequence of primer hTNFa-r.

SEQ ID NO:59 is a nucleic acid sequence of primer hIL6-f.

SEQ ID NO:60 is a nucleic acid sequence of primer hIL6-r.

SEQ ID NO:61 is a nucleic acid sequence of primer hIL1b-f.

SEQ ID NO:62 is a nucleic acid sequence of primer hIL1b-r.

SEQ ID NO:63 is a nucleic acid sequence of primer hu-IFN-b-f.

SEQ ID NO:64 is a nucleic acid sequence of primer hu-IFN-b-r.

SEQ ID NO:65 is a nucleic acid sequence of primer hu-IL-12-f.

SEQ ID NO:66 is a nucleic acid sequence of primer hu-IL-12-r.

SEQ ID NO:67 is a nucleic acid sequence of primer hIL-15F2.

SEQ ID NO:68 is a nucleic acid sequence of primer hIL-15R2.

SEQ ID NO:69 is a nucleic acid sequence of primer hGAPDH f.

SEQ ID NO:70 is a nucleic acid sequence of primer hGAPDH r.

SEQ ID NO:71 is a nucleic acid sequence of primer TNF-a-FW.

SEQ ID NO:72 is a nucleic acid sequence of primer TNF-a-RV.

SEQ ID NO:73 is a nucleic acid sequence of primer mIL6-f.

SEQ ID NO:74 is a nucleic acid sequence of primer mIL6-r.

SEQ ID NO:75 is a nucleic acid sequence of primer mIL1a-f.

SEQ ID NO:76 is a nucleic acid sequence of primer mIL1a-r.

SEQ ID NO:77 is a nucleic acid sequence of primer b-actin-f.

SEQ ID NO:78 is a nucleic acid sequence of primer b-actin-r.

DETAILED DESCRIPTION

The present invention provides fusion proteins comprising peptides derived from the extracellular domain of alternatively spliced isoforms of human PD1 (herein referred to as "Δ42PD1") (FIGS. 1A through 1D) to regulate innate immunity, as well as uses of Δ42PD1 for potentiating antigen-specific antibody and particularly CD8$^+$ T-cell immune responses.

In one embodiment, novel PD1 isoform (Δ42PD1) can be used as a potential intramolecular adjuvant for vaccine development to induce high level of functional and long-lived antigen-specific CD8$^+$ T immunity against cancers and infections by pathogens including HIV-1 and *Mycobacterium tuberculosis*.

As the Δ42 deletion results in the loss of the beta-strand A of human PD1 (FIG. 7), the Δ42PD1 isoform is unable to bind PD-L1/L2 or specific PD1 blocking monoclonal antibodies (FIGS. 2A through 2C). Δ42PD1-mediated enhancement of antigen-specific immunity is unlikely through PD-L1/L2 interaction with dendritic cells but rather through a distinct mechanism.

The stimulation of pro-inflammatory cytokines by Δ42PD1 contributes to the overall T cell immunity; therefore, Δ42PD1-based fusion DNA vaccine can enhance T cell immunity. In particular, since the enhanced antigen-specific CD8+ T cell immunity confers functional and long-lasting effects in vivo, Δ42PD1-based fusion DNA vaccine offers new opportunities to improve vaccine and immunotherapy efficacy against pathogens and cancers.

Figure 1:
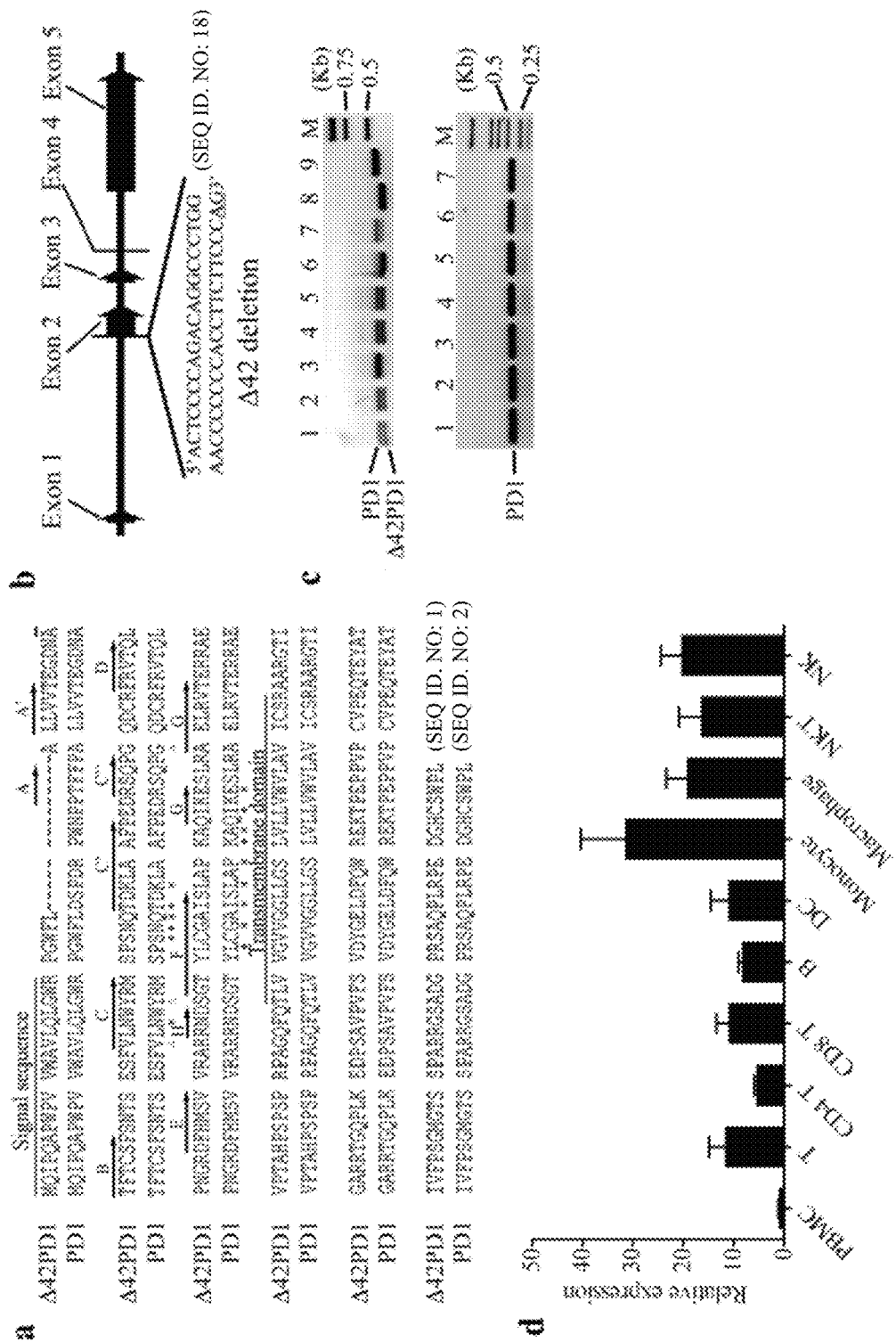
FIGS. 1A through 1D show the identification of a novel PD1 isoform.

Δ42PD1 is a newly discovered PD1 isoform that could induce pro-inflammatory cytokines for function. This isoform was found among healthy Chinese blood donors whose PBMCs express a PD1 transcript with an identical 42-nucleotide deletion at the beginning of exon 2 (FIGS. 1A through 1D), and differs from other alternatively spliced PD1 variants as reported previously. Δ42PD1 mRNA is preferentially expressed in monocytes, macrophages, NKT and NK cells as compared to DCs, B cells and T cells (FIG. 1D). This phenomenon has not been reported for PD1 or spliced variants of other CD28 family members such as CTLA-4 and CD28.

Soluble forms of PD1, CD28, CD80, CD86 and CTLA-4 can be found in sera of patients suffering from autoimmune diseases such as Sjogren's syndrome, systemic lupus erythematosus, multiple sclerosis, neuromyelitis optica, and rheumatoid arthritis, and antibodies detecting naturally occurring sΔ42PD1 can be used in diagnosis (including diagnostic reagents) and/or treatment of auto immune diseases and infections.

Figure 4A:
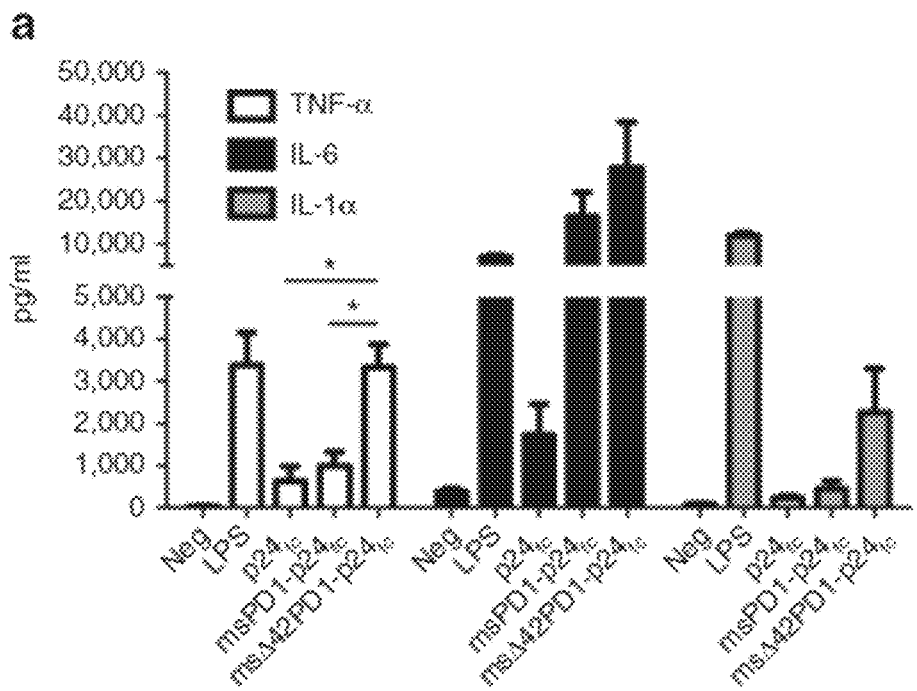
FIGS. 4A through 4F show enhanced antigen-specific immunogenicity of msΔ42PD1-p24$_{fc}$ DNA/EP in mice.
Figure 4B:
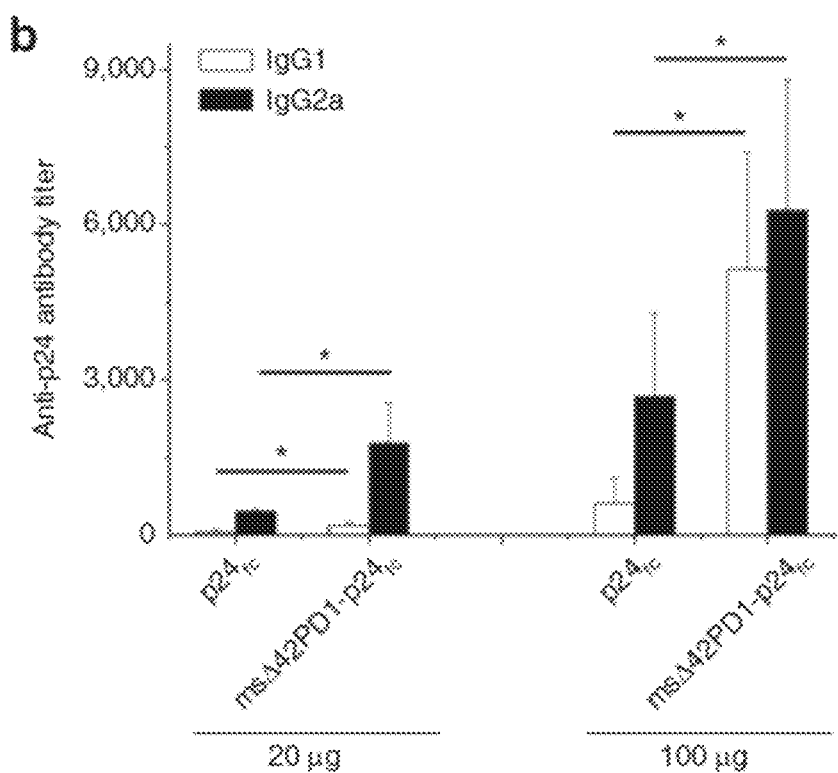

Δ42PD1, a PD1 spliced variant resulted from a partial exon deletion, is distinct from PD1: firstly, it does not bind to PD-L1/L2, and secondly, recombinant soluble or membrane-bound Δ42PD1 (but not PD1) can induce the expression of TNF-α, IL-6 and IL-1β. It is postulated that the Δ42PD1 has distinct immunoregulatory functions that could influence the stimulation of an immune response. Eliciting high levels of functional CD8+ T cell immunity is one of the important determinants of an effective vaccine against intracellular pathogens and cancer. Thus, nucleic acid molecules encoding Δ42PD1 can be used as an intramolecular adjuvant in a fusion DNA vaccine strategy, and can be used to elicit remarkably enhanced functional CD8+ T cell immunity against HIV-1 Gag p24 in vivo (FIGS. 4D and 4E). At a dose of 20 μg of DNA in Balb/c mice, msΔ42PD1-p24$_{fc}$/EP vaccination could achieve robust induction of p24-specific CD8+ (~1000 Elispots/10 splenocytes; ~20-fold greater than p24$_{fc}$), which are markedly different from those using either three doses of 1 mg of gene-optimized ADVAX DNA vaccine or two doses of $10^6$ TCID$_{50}$ vaccinia-vectored ADMVA vaccine that only induced 200-250 spot forming units (SFUs)/$10^6$ splenocytes against the identical GagAI epitope. Meantime, ~17% of tetramer+ CD8+ T cells from DNA vaccination was similar to those elicited by rAd5-Gag vaccination with three dosages of $10^{10}$ virus particles, or by a DC-SIGN-targeted lentivirus-Gag with two doses of $5\times10^6$ TU (transduction units). The immunogenicity of the fusion DNA/EP vaccine strategy, therefore, is potent for eliciting anti-HIV CD8+ T cell immunity.

Figure 5A:
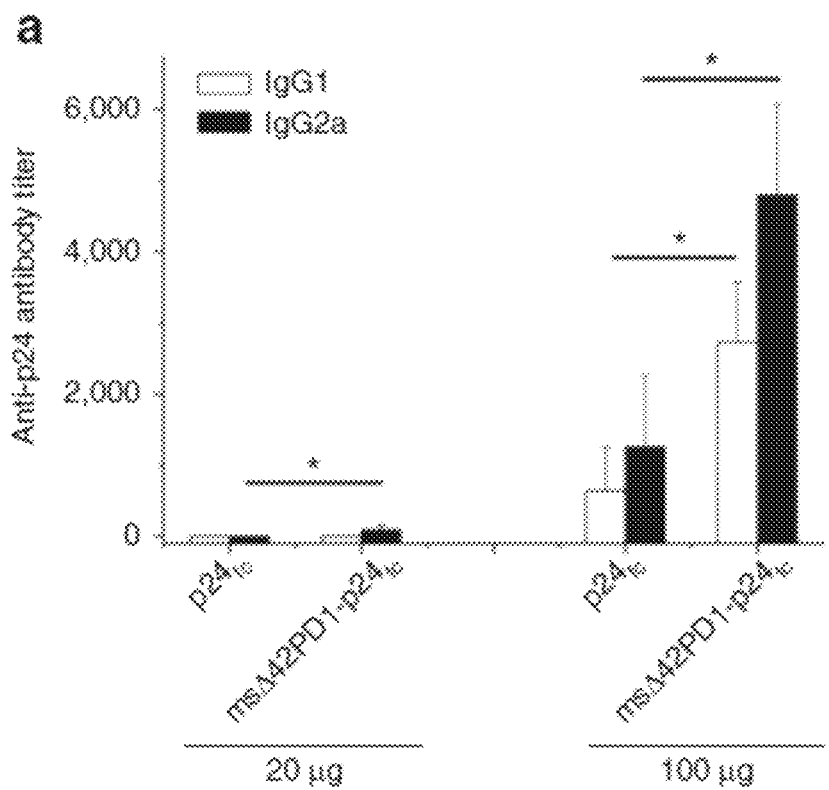
Figure 5B:
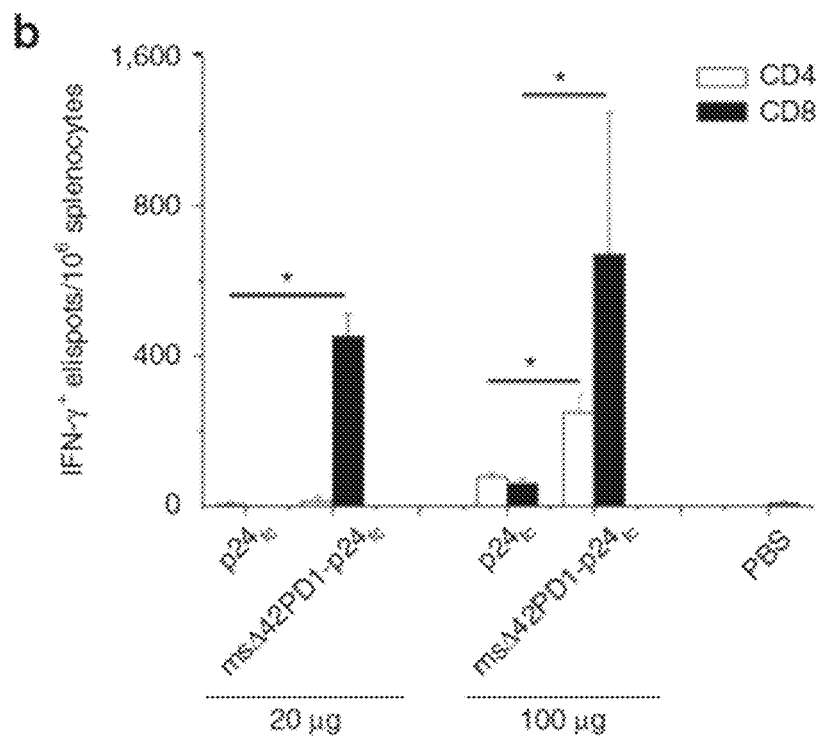
Figure 6:
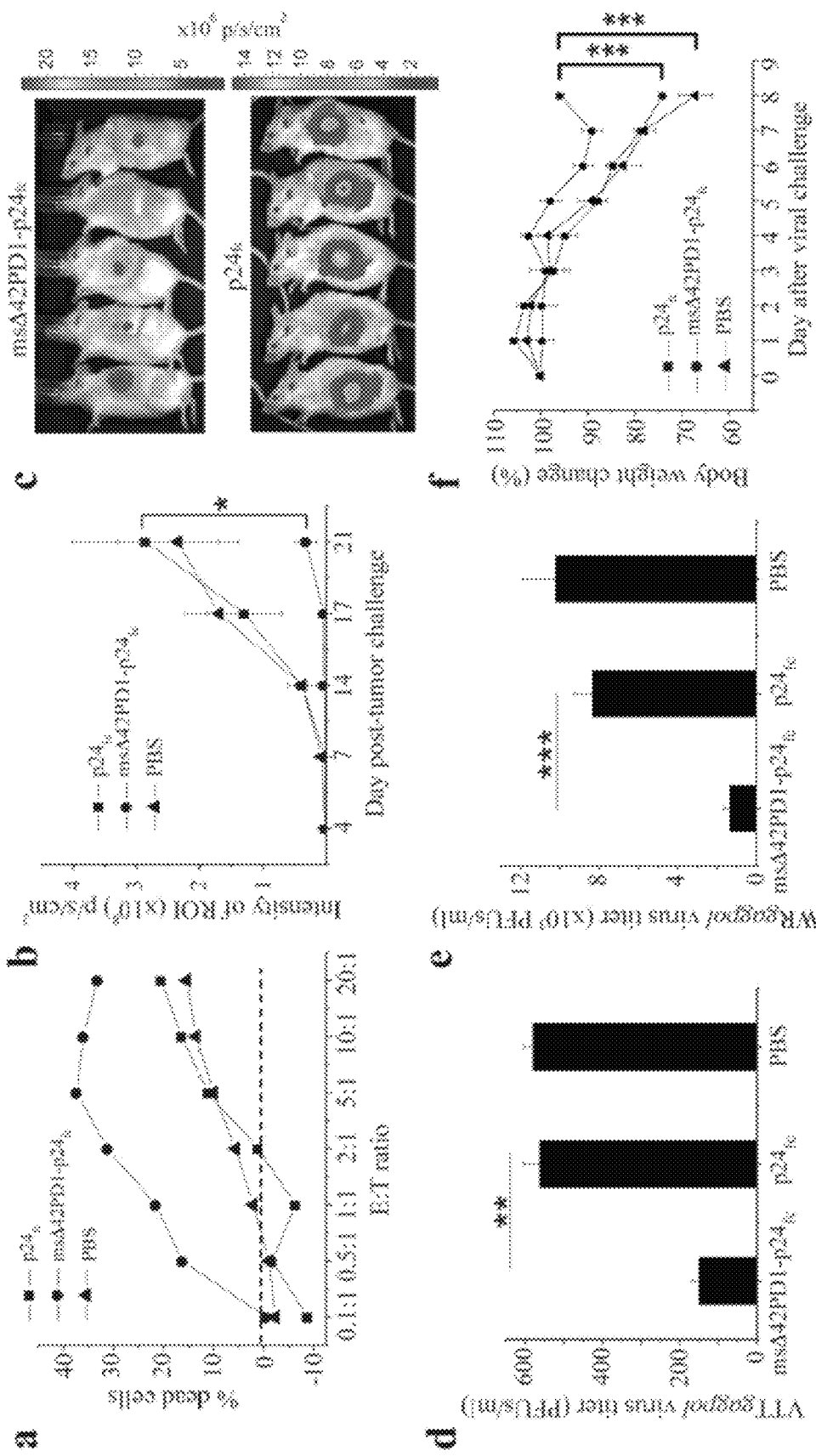
FIGS. 6A through 6F show the efficacy of msΔ42PD1-p24$_{fc}$ vaccination in mice.

Furthermore, as long-lasting CD8+ T cell-mediated immunity to a particular intracellular pathogen requires the establishment of a memory cell pool that proliferates rapidly in response to antigen re-encounter, Δ42PD1 fusion DNA induced higher frequencies of not only IFN-γ producing but proliferating p24-specific CD8+ T cells 7.5 months after immunization (FIGS. 5B and 5D). Most importantly, msΔ42PD1-p24$_{fc}$ vaccination significantly inhibited tumor growth in vivo (FIGS. 6B and 6C) in line with more effective cytotoxic T cells capable of eliminating AB1-HIV-1-Gag tumor cells in vitro (FIGS. 6A). In addition, mice vaccinated with msΔ42PD1-p24$_{fc}$ were protected against both attenuated (VTTgagpol) and virulent (WRgagpol) vaccinia viruses from mucosal challenges (FIGS. 6D and 6E) with minimal body weight loss (FIG. 6F). Here, since neither neutralizing antibodies nor T cell immunity against the backbone vaccinia viruses were generated, the observed protection was also primarily due to the significantly enhanced T cell immunity directed at HIV-1 Gag p24.

The mechanism of the success of msΔ42PD1 fusion DNA vaccine in mice can be contributed by the ability of msΔ42PD1 to induce the expression of TNF-α, IL-6 and IL-1α/β. These cytokines may play active roles in the generation of antigen-specific adaptive immunity by acting on APCs, such as DCs. TNF-α can induce the maturation of professional antigen presenting DCs and increase the expression of MHC and co-stimulatory molecules, and migration to draining lymph nodes to prime naïve T cells. With the addition of IL-1α/β, these matured DCs become more potent at promoting the differentiation of IFN-γ-producing T cells in a Th1 manner. While synergistically, TNF-α and IL-6 can provide co-stimulatory cytokine signals to induce the proliferation of T cells. IL-6 has also been found to inhibit the activity of regulatory T cells to ensure the production of IFN-γ by CD4+ T cells.

As elevated levels of cytokines were not detected systemically in mice sera (Table S3), it is postulated that the high level of functional B and T cell immunity elicited by the sΔ42PD1-based DNA fusion vaccine can be contributed by the induction of TNF-α, IL-6 and IL-1α/β at the site of vaccination. Other DNA vaccine studies have also shown that T cell responses were elicited by co-administering plasmids encoding HIV-1 Env and CD86 adjuvant to enable non-bone marrow-derived cells to prime CD8+ T cells at the site of injection assisted by a pro-inflammatory environment that can enhance antigen presentation. As for the weak CD4+ but strong CD8+ T cell responses observed, other cytokine signals such as IL-12 or type I IFN may play a role in favoring naïve CD8+ T cell activation. It has also been reported that IL-15 alone can substitute for CD4+ T helper cell in stimulating CD8+ T cell activation and expansion.

The present invention also shows that TNFb, IL12 and IL15 transcripts were increased in PBMCs treated with sΔ42PD1$_{fc}$ after 12 h (FIGS. 16A through 16C). Additionally, the induction of IL-1α/β and IL-6 by sΔ42PD1$_{fc}$ may also contribute to CD8+ T cell response by inhibiting activation-induced cell death.

Protein Isoforms, Nucleic Acid Molecules, and Fusion Proteins and Fusion Nucleic Acid Constructs A first aspect of the subject invention provides PD1 protein isoforms. In one embodiment, the PD1 protein isoform is Δ42PD1, which has an amino acid sequence comprising SEQ ID NO: 1. In one embodiment, the PD1 protein isoforms do not bind to PDL1 or PDL2.

In one embodiment, the PD1 protein isoform has a deletion of 14 amino acids at positions corresponding to amino acids 26-39 of the wild-type PD1 protein having an amino acid sequence of SEQ ID NO:2. In one embodiment, the 14 amino acid deletion has a sequence that is DSPDRPWNPPTFFP (SEQ ID NO:3).

In another embodiment, the PD1 protein isoform has non-conservative substitutions at one or more amino acids at positions corresponding to amino acids 26-39 of the wildtype PD1 protein having an amino acid sequence of SEQ ID NO:2. In certain embodiments, the PD1 protein isoform has non-conservative substitutions of 1 to 14 amino acids at positions corresponding to amino acids 26-39 of the wild-type PD1 protein having an amino acid sequence of SEQ ID NO:2. In one embodiment, amino acids 26-39 of the wild-type PD1 protein are DSPDRPWNPPTFFP (SEQ ID NO:3).

The wild-type PD1 protein is preferably of mammalian origin (such as a wild-type mouse, rabbit, non-human primates, or pig PD1 protein), more preferably, of human origin.

In certain embodiments, the present invention provides PD1 protein isoforms that are homologous to Δ42PD1 (SEQ ID NO: 1). In an embodiment, the PD1 protein isoform comprises an amino acid sequence that is at least about 80%, 85%, 90%, 93%, 95%, 96%, 97%, 98%, 99%, or 99.5% identical to SEQ ID NO: 1.

In an embodiment, the present invention provides PD1 protein isoforms that are homologous to Δ42PD1, wherein the PD1 protein isoform has non-conservative substitutions of 1 to 14 amino acids at positions corresponding to amino acids 26-39 of the wild-type PD1 protein having an amino acid sequence of SEQ ID NO:2, and the PD1 protein isoform comprises an amino acid sequence that is at least about 80%, 85%, 90%, 93%, 95%, 96%, 97%, 98%, 99%, or 99.5% identical to amino acids 11-276 of SEQ ID NO: 1.

In an embodiment, the present invention provides PD1 protein isoforms that are homologous to Δ42PD1, wherein the PD1 protein isoform has a deletion of 14 amino acids at positions corresponding to amino acids 26-39 of the wild-type PD1 protein having an amino acid sequence of SEQ ID NO:2, and the PD1 isoform comprises an amino acid sequence that is at least about 80%, 85%, 90%, 93%, 95%, 96%, 97%, 98%, 99%, or 99.5% identical to amino acids 11-276 of SEQ ID NO: 1.

In certain embodiments, the present invention provides fragments of the PD1 protein isoforms. In certain embodiments, the fragments of the PD1 protein isoforms of the present invention have at least 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, 200, 205, 210, 220, 215, 220, 225, 230, 235, 240, 245, 250, 255, 260, 265, 270, 275, or 280 amino acids.

In a preferred embodiment, the present invention provides soluble fragments of the PD1 protein isoforms of the present invention.

Another aspect of the subject invention provides nucleic acid molecules that encode the PD1 proteins of the subject invention. The nucleic acid molecules encompass DNA molecules (e.g. genomic DNA and cDNA) and RNA molecules. In addition, the subject nucleic acid molecules may be single-stranded or double-stranded. In one embodiment, the PD1 nucleic acid molecules of the present invention are formulated into a DNA vaccine formulation.

In one embodiment, the nucleic acid molecule encodes a PD1 protein isoform having a deletion of 14 amino acids at positions corresponding to amino acids 26 to 39 of the wild-type PD1 protein having an amino acid sequence of SEQ ID NO:2. In one embodiment, the nucleic acid molecule encodes a PD1 protein isoform having non-conservative substitutions at one or more amino acids at positions corresponding to amino acids 26-39 of the wild-type PD1 protein having an amino acid sequence of SEQ ID NO:2. In certain embodiments, the nucleic acid encodes a PD1 protein isoform having non-conservative substitutions at 1 to 14 amino acids at positions corresponding to amino acids 26 to 39 of the wild-type PD1 protein having an amino acid sequence of SEQ ID NO:2. In one embodiment, amino acids 26-39 of the wild-type PD1 protein are DSPDRPWNPPTFFP (SEQ ID NO:3).

Another aspect of the invention provides PD1 fusion proteins and fusion nucleic acid molecules. In a preferred embodiment, the PD1 fusion nucleic acid molecules of the present invention are formulated into a DNA vaccine formulation. In additional preferred embodiments, the PD1 fusion nucleic acid molecules of the present invention are formulated into immunogens for antibody preparation.

In one embodiment, the PD1 fusion protein comprises a Fc domain. In one embodiment, the Fc domain is rabbit IgG1 Fc. In one embodiment, the soluble PD1 protein is linked to the antigen via a linker sequence. In an alternative embodiment, the PD1 fusion protein comprises a PD1 protein fused with a Fc domain, optionally via a linker sequence.

In one embodiment, the PD1 fusion protein comprises a PD1 protein of the present invention fused with an antigenic protein fragment.

In one embodiment, the antigenic protein fragment is a HIV gag p24 antigen fragment.

The antigenic protein fragment can be derived from an immunogenic fragment of viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza, bovine leukemia virus (BLV), Epstein-Barr virus, pertussis, polio, measles, mumps, rubella, smallpox, zoster, anthrax, tetanus, rotavirus, rabies, chickenpox, meningococcus, diphtheria, anpapillomavirus, anthrax, plague, encephalitis, pneumococcus, pneumonia, typhus, typhoid fever, streptococcus, staphylococcus, neisseria, lyme disease, cholera, *E. coli*, shigella, leishmania, leprosy, cytomegalovirus (CMV), respiratory syncytial virus, parainfluenza, adenovirus, varicella, flavivirus, dengue toxoplasmosis, coccidiomycosis, schistosomiasis, *Mycobacteria tuberculosis*, and malaria.

In certain specific embodiments, the antigenic protein fragment are derived from microbial pathogens including HIV, hepatitis viruses including hepatitis A virus, hepatitis B virus, hepatitis C virus, hepatitis D virus, hepatitis E virus, hepatitis F virus, and hepatitis G virus, oncoviruses, and *Mycobacteria tuberculosis*.

The antigenic protein fragment can also be derived from tumor or cancer cells. In one embodiment, the PD1 protein isoforms, and fusion proteins thereof serve as molecular or protein adjuvants to enhance immune response. Additionally, nucleic acid molecules encoding the PD1 protein isoforms, and fusion proteins thereof can also be administered to a subject to enhance immune response.

In an embodiment, the antigenic protein fragment is derived from an immunogenic fragment of an HIV protein domain including, but not limited to, p24, gag, pol, nef, tat, rev, gp120, and gp41. In a further embodiment, the PD1 fusion protein further comprises a Fc domain. In an embodiment, the PD1 fusion protein comprises a rabbit Fc domain for protein purification purpose.

The term "Fc domain" encompasses the full length and fragments of native human and animal Fc and Fc variant molecules and sequences, including for example, IgG, IgM, IgD, IgE, IgA and subtypes such as for example IgG1, IgG2, IgG3, IgG4, IgA1, and IgA2. As with Fc variants and native Fc's, the term "Fc domain" includes molecules in monomeric or multimeric form, whether digested from whole antibody or produced by other means.

The term "Fc variant" refers to a molecule or sequence that is modified from a native Fc but still comprises a binding site for the salvage receptor. Fc domains include molecules having two or more polypeptide chains associated covalently, noncovalently, or by both covalent and noncovalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The Fc domain within the scope of the invention can be of antibodies of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes. In a specific embodiment, the Fc domain is IgG1.

In a further embodiment, the PD1 fusion protein of the subject invention comprises a linker sequence that links the soluble PD1 domain to the antigen. In addition, the Fc domain can also be linked to the fusion protein via a linker sequence. Linker sequence is typically a peptide chain. The length of the peptide may be, for example, 6, 7, 8, 9, 10, 11, 12, 13, 14, 15, 16, 17, 18, 19, 20, 21, 22, 23, 24, 25, 30, 40, 50 or more amino acid residues, but typically is between 5 and 25 residues. Depending upon the length and side chain composition, a linker may have, but need not have, greater than average flexibility. Flexibility can be calculated using algorithms known in the art. Examples of useful linkers include, but are not limited to, GGGGSGGGG (SEQ ID NO:4), GGTGGTGGTTCAGGAGGAGGA) (SEQ ID NO:5), 9Gly (SEQ ID NO: 8), 9Glu (SEQ ID NO: 9), 9Ser (SEQ ID NO: 10), 5GlyCys2ProCys (SEQ ID NO: 11), 4Gly3Ser (SEQ ID NO: 12), Ser Cys Val Pro Leu Met Arg Cys Gly Gly Cys Cys Asn (SEQ ID NO: 13), Pro Ser Cys Val Pro Leu Met Arg Cys Gly Gly Cys Cys Asn (SEQ ID NO: 14), Gly Asp Leu Ile Tyr Arg Asn Gln Lys (SEQ ID NO: 15), and 9GlyProSerCysValProLeuMetArgCysGlyGlyCysCysAsn (SEQ ID NO: 16).

In addition, the subject invention provides PD1 fusion nucleic acid constructs, comprising a nucleic acid molecule encoding the subject PD1 fusion protein. In one embodiment, the PD1 fusion construct comprises a nucleic acid molecule encoding a PD1 protein fused with a nucleic acid encoding a protein antigen. In a further embodiment, the PD1 fusion construct comprises a Fc DNA. In one embodiment, the soluble PD1 DNA is linked to the antigen DNA via a linker sequence. Optionally, the Fc DNA is linked to the PD1-antigen DNA via a linker DNA sequence.

The antigenic nucleic acid molecule of the subject invention encodes immunogenic fragments of viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza, bovine leukemia virus (BLV), Epstein-Barr virus, pertussis, polio, measles, mumps, rubella, smallpox, zoster, anthrax, tetanus, rotavirus, rabies, chickenpox, meningococcus, diphtheria, anpapillomavirus, anthrax, plague, encephalitis, pneumococcus, pneumonia, typhus, typhoid fever, streptococcus, staphylococcus, neisseria, lyme disease, cholera, *E. coli, shigella, leishmania*, leprosy, cytomegalovirus (CMV), respiratory syncytial virus, parainfluenza, adenovirus, varicella, flavivirus, dengue toxoplasmosis, coccidiomycosis, schistosomiasis, *Mycobacteria tuberculosis*, and malaria.

In one embodiment, the present invention provides isolated PD1 isoform and nucleic acid molecules encoding the PD1 isoforms, such as PD1 isoform Δ42PD1. In certain embodiments, the PD1 protein or nucleic acid of the subject invention is typically substantially free of other components, such as other biological molecules, proteins or peptides, nucleic acids, lipids and carbohydrates. The term "substantially free of," as used herein, encompasses preparations of the subject invention having less than about 20%, 10% and preferably less than 5% (by dry weight) contaminating factors (such as biological molecules, proteins or peptides, nucleic acids, lipids and carbohydrates and other cellular components).

If desired, the subject proteins and nucleic acid molecules can be modified by any suitable process. Strategies for protein optimization are sometimes carried out using random mutagenesis. In these cases positions are chosen randomly, or amino acid changes are made using simplistic rules. For example all residues may be mutated to alanine, referred to as alanine scanning. In addition, substitution of amino acids other than those specifically exemplified or naturally present in a fusion protein of the invention are also within the scope of the subject invention. For example, non-natural amino acids can be substituted for the amino acids of the fusion protein, so long as the fusion protein having the substituted amino acids retains substantially the same functional activity as the fusion protein in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, T-butylglycine, T-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The subject invention also concerns variants of nucleic acid molecules that encode functional fusion proteins of the invention. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those nucleic acid molecules having sequences which are sufficiently homologous with the nucleic acid sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

Tm=81.5 C+16.6 Log [Na+]+0.41(% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

Further, the subject invention provides expression constructs comprising PD1 nucleic acid molecules or fusion constructs thereof. Expression constructs of the invention generally include regulatory elements that are functional in the intended host cell in which the expression construct is to be expressed. Regulatory elements include promoters, transcription termination sequences, translation termination sequences, enhancers, and polyadenylation elements.

An expression construct of the invention can comprise a promoter sequence operably linked to a nucleic acid sequence encoding a peptide of the invention. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. For mammalian cells, suitable promoters include such as, for example, Pcmv, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, and TRP-1 promoter.

Induction of Cytokines

Another aspect of the present invention provides uses of the PD1 protein isoforms, e.g., Δ42PD1, nucleic acid molecules encoding the PD1 protein isoforms, fusion proteins comprising the PD1 protein isoforms, and/or fusion nucleic acid molecules comprising nucleic acid sequences encoding the PD1 protein isoforms for induction of production of cytokines (such as, TNF-α, IL-1, and IL-6) in immune cells.

In one embodiment, the present invention provides a method of inducing the production of TNF-α, IL-1, and/or IL-6, wherein the method comprises administering, to an immune cell (preferably, an immune cell in a subject), a PD1 protein isoform, a nucleic acid molecules encoding the PD1 protein isoform, a fusion protein comprising the PD1 protein isoform, and/or a fusion nucleic acid molecule comprising nucleic acid sequences encoding a PD1 protein isoform of the present invention.

Prevention and/or Treatment of Pathogenic Infection

Another aspect of the present invention provides methods for the prevention, diagnosis, treatment, or amelioration of pathogenic infection. Advantageously, the methods of the subject invention enhance T cell immunity. The method comprises administering to a subject in need of such prevention and treatment an effective amount of a PD1 protein isoform of the present invention (such as Δ42PD1 protein), nucleic acid molecule encoding a PD1 protein isoform of the present invention (such as Δ42PD1 protein), and/or fusion protein and/or fusion nucleic acid molecule of the present invention.

In addition, the methods can be used in the prevention or treatment of diseases where enhanced T cell immunity is beneficial. In a specific embodiment, the subject invention can be used in the prevention, diagnosis, and/or treatment of tumor or cancer.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof.

The term "effective amount," as used herein, refers to an amount that is capable of treating or ameliorating a disease or condition or otherwise capable of producing an intended therapeutic effect.

The term "subject," as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

In one embodiment, the subject invention can be used in the prevention, treatment or amelioration of infection by viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza, bovine leukemia virus (BLV), Epstein-Barr virus, pertussis, polio, measles, mumps, rubella, smallpox, zoster, anthrax, tetanus, rotavirus, rabies, chickenpox, meningococcus, diphtheria, anpapillomavirus, anthrax, plague, encephalitis, pneumococcus, pneumonia, typhus, typhoid fever, streptococcus, staphylococcus, neisseria, lyme disease, cholera, *E. coli, shigella, leishmania*, leprosy, cytomegalovirus (CMV), respiratory syncytial virus, parainfluenza, adenovirus, varicella, flavivirus, dengue toxoplasmosis, coccidiomycosis, schistosomiasis, *Mycobacteria tuberculosis*, and malaria.

In one embodiment, the PD1 protein useful for the treatment or amelioration of tumor comprises an antigenic fragment derived from cancer or tumor cells.

Antibodies

Another aspect of the invention provides antibodies that bind specifically to the PD1 protein isoforms (such as Δ42PD1 protein) of the present invention. In one specific embodiment, the present invention provides CH34—an antibody that binds specifically to the Δ42PD1 protein. Such antibodies are also useful in diagnostic applications, such as but not limited to, tests that utilize FACS, WB, IF, IHC, EILSA, Elispot, and other tests. In another specific embodiment, the present invention provides CH101—an antibody that can both bind specifically to the Δ42PD1 protein and block the binding between the Δ42PD1 and its unknown receptor. Such antibodies, on one hand, are useful in diagnostic applications, such as but not limited to, tests that utilize FACS, WB, IF, IHC, EILSA, Elispot, and other tests. On the other hand, such blocking antibodies are likely to be useful in interfering with Δ42PD1 signaling, as components of therapeutic agents, such as but not limited to therapeutic antibodies, for treating Δ42PD1 related disease conditions.

The term "binding specificity," "specificity," "specifically reacts," or "specifically interacts," as used herein, refers to the ability of an antibody or other agent to detectably bind an epitope presented on an antigen, such as an epitope of HIV-1 gp120, while having relatively little detectable reactivity with other proteins or structures. Specificity can be relatively determined by binding or competitive assays, using e.g., Biacore instruments. Specificity can be exhibited by, e.g., an about 10:1, about 20:1, about 50:1, about 100:1, about 10,000:1 or greater ratio of affinity/avidity in binding to the specific antigen versus nonspecific binding to other irrelevant molecules.

Antibodies of the present invention can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment (e.g., a fusion protein containing a fragment of CD4, e.g., sCD4 (Salzwedel et al. J. Virol. 74:326 333, 2000); and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments called Fab fragments, each with a single antigen binding site, and a residual "Fc" fragment, so-called for its ability to crystallize readily. Pepsin treatment of an antibody yields an F(ab')$_2$ fragment that has two antigen binding portions which are capable of cross-linking antigen, and a residual other fragment (which is termed pFc'). Additional fragments can include diabodies, linear antibodies, single-chain antibody molecules, and multispecific antibodies formed from antibody fragments.

The subject invention also comprises fusion constructs wherein the antibody, or fragment thereof, may be fused to one or more additional entities. The additional entity(ies) may be for example linkers, toxins, carriers, solid supports, and/or detectable molecules. In this context the binding portion may consist of or consist essentially of the antibody.

Antibodies of the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

Monoclonal antibodies of the invention can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the monoclonal antibodies of the invention can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 (Burton et al.) and U.S. Pat. No. 6,096,441 (Barbas et al.). Recombinant antibodies, antibody fragments, and fusions and polymers thereof can be expressed in vitro or in prokaryotic cells (e.g., bacteria) or eukaryotic cells (e.g., yeast, insect, or mammalian cells) and further purified, as necessary, using well known methods (see, e.g., Sambrook et al. Molecular Cloning: a Laboratory Manual, Cold Spring Harbor Laboratory Press (1989); and Ausubel et al., Current Protocols in Molecular Biology, John Wiley & Sons, New York, N.Y., 2001, which is updated quarterly).

Antibodies of the present invention include human and humanized antibodies. The human antibodies of the invention can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1): δ 95, 1991). Human antibodies of the invention (and fragments thereof) can also be produced using phage display libraries (Hoogenboom et al., J. Mol. Biol., 227:381, 1991; Marks et al., J. Mol. Biol., 222:581, 1991; and C. F. Barbas, D. R. Burton, J. K. Scott, G. J. Silverman, Phage Display: A Laboratory Manual, Cold Spring Harbor Laboratory Press, Cold Spring Harbor, N.Y., 2001).

The humanized antibodies of the present invention may be derived from animal subjects such as mouse, rabbit, and etc. Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

Methods for humanizing non-human antibodies are well known in the art. For example, humanized antibodies can be generated according to the methods of Winter and coworkers (Jones et al., Nature, 321:522 525 (1986), Riechmann et al., Nature, 332:323 327 (1988), Verhoeyen et al., Science, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

If desired, the antibodies of the present invention can be modified in any suitable process. For example, the binding affinity of the antibodies can be increased via various methods known in the art. For example, binding characteristics can be improved by direct mutation, methods of affinity maturation, phage display, or chain shuffling within the nucleic acids encoding the antibody molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol. Bio.* 254, 392-403; Hawkins et al. (1992) *J. Mol. Bio.* 226, 889-896; or Low et al. (1996) *J. Mol. Bio.* 250, 359-368 (each of which is hereby incorporated by reference in its entirety, particularly with respect to methods of increasing the binding affinity of antibodies)). Methods known in the art include for example, Marks et al. *BioTechnology,* 10:779-783 (1992) describes affinity maturation by VH and VL domain shuffling; random mutagenesis of CDR and/or framework residues is described by Barbas et al. *Proc. Natl. Acad. Sci., USA* 91:3809-3813 (1994); Schier et al. *Gene,* 169:147-155 (1995); Yelton et al. *J. Immunol.,* 155:1994-2004 (1995); Jackson et al., *J. Immunol.,* 154(7):3310-3319 (1995); and Hawkins et al, *J. Mol. Biol.,* 226:889-896 (1992).

Strategies for antibody optimization are sometimes carried out using random mutagenesis. In these cases positions are chosen randomly, or amino acid changes are made using simplistic rules. For example all residues may be mutated to alanine, referred to as alanine scanning WO 9523813 (which is hereby incorporated by reference in its entirety) teaches in vitro methods of increasing antibody affinities utilizing alanine scanning mutagenesis. Alanine scanning mutagenesis can also be used, for example, to map the antigen binding residues of an antibody (Kelley et al., 1993, *Biochemistry* 32:6828-6835; Vajdos et al., 2002, *J. Mol. Biol.* 320:415-428). Sequence-based methods of affinity maturation (see, U.S. Pat. Application No. 2003/022240 A1 and U.S. Pat. No. 2002/177170 A1, both hereby incorporated by reference in their entireties) may also be used to increase the binding affinities of antibodies.

Therapeutic Compositions and Routes of Administration

The subject invention further provides for therapeutic or pharmaceutical compositions. In one embodiment, the therapeutic composition is formulated as a vaccine composition.

In an embodiment, the composition comprises a therapeutically effective amount of a protein and/or nucleic acid molecule of the subject invention and, optionally, a pharmaceutically acceptable carrier.

A vaccine composition is an antigenic preparation that comprises one or more immunogenic antigens used to produce active immunity to a disease. Such compositions may contain suitable pharmaceutically acceptable carriers, such as excipients, adjuvants and/or auxiliaries, and other therapeutically inactive ingredients.

In one embodiment, the proteins and/or nucleic acid molecules are formulated into a vaccine composition for administration to subjects having certain risks of pathogenic infection. A vaccine composition is an antigenic preparation that comprises one or more immunogenic antigens used to produce active immunity to a disease. In addition, the compositions of the subject invention can be administered to a subject with existing infection, and provides for customized vaccine schedules and compositions to prevent or minimize worsening of the diseases.

The subject invention contemplates therapeutic compositions useful for practicing the therapeutic methods described herein. The therapeutic composition can be any form of pharmaceutical format, including injectable formulations such as liquid and lyophilized injections.

In a specific embodiment, a therapeutically effective amount of a protein and/or nucleic acid molecule of the subject invention is typically an amount such that when administered in a physiologically tolerable composition is sufficient to achieve a plasma concentration of from about 0.01 microgram (ug) per milliliter (mL) to about 200 ug/mL.

Suitable non-toxic pharmaceutically acceptable carriers for use with the agent will be apparent to those skilled in the art of pharmaceutical formulation. See, for example, *Remington's Pharmaceutical Sciences,* seventeenth edition, ed. Alfonso R. Gennaro, Mack Publishing Company, Easton, Pa. (1985). Suitable carriers include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic composition, if desired, can also contain minor amounts of wetting or emulsifying agents, or pH buffering agents. In addition, if desired, the composition can contain minor amounts of auxiliary substances such as wetting or emulsifying agents, pH buffering agents and the like which enhance the effectiveness of the active ingredient.

The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80%, or about 30% to about 70%, active ingredient (w/w).

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The therapeutic composition of the subject invention can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The invention also provides a pharmaceutical pack or kit comprising one or more containers filled with one or more of the ingredients, e.g., compound, carrier suitable for administration.

The compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In a preferred embodiment, the microparticles of the subject invention can be formulated for parenteral administration. The preparation of an aqueous composition that contains one or more agents, such as a protein or nucleic acid molecule of the subject invention, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active ingredients in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

In addition, the nucleic acid molecules and compositions of the subject invention can be delivered in vivo into a host cell by methods known in the art. In one embodiment, the nucleic acid molecules and compositions of the subject invention can be introduced in vivo via a viral vector such as adeno-associated virus (AAV), herpes simplex virus (HSV), retrovirus, papillomavirus, adenovirus, and Epstein-Barr virus (EBV). In addition, the nucleic acid molecules and compositions of the subject invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate the nucleic acid molecules of the invention. The nucleic acid molecules of the subject invention can also be introduced in vivo as naked DNA using methods known in the art, such as transfection, microinjection, electroporation, calcium phosphate precipitation, and by biolistic methods.

Materials and Methods

Primers and Antibodies.

All primer sequences and antibodies used are listed in Table S1 and S2, respectively.

TABLE S1

Primer sequences used.

| Primer name | Sequences |
| --- | --- |
| PD1 forward | 5'-GCAGT GGAGA AGGCG GCACT CT-3' |
| PD1 reverse | 5'-CTTCT CCTGAG GAAATG CGCTG ACC-3' |
| PD-L1 forward | 5'-AGGGC ATTCC AGAAA GATGA GGATA-3' |
| PD-L1 reverse | 5'-CCCGA TGAAC CCCTA AACCA CA-3' |
| PD-L2 forward | 5'-GAGCT GTGGC AAGTC CTCAT ATCAA-3' |
| PD-L2 reverse | 5'-GCAGT GGAGA AGGCG GCACT CT-3' |
| PD-1D forward | 5'-GCAGA GGCCC CAGCA GAGAC TTCTC AATGA CATTC-3' |
| PD-1D reverse | 5'-TGCTT CCAGA GCTAG AGGAC AGAGA TGCCG GTCAC-3' |
| nPD-1 forward | 5'-AGTCG TCTGG GCGGT GCTAC AACTG-3 |
| nPD-1 reverse | 5'-GCTGG GGTGG GCTGT GGGCA CTTCT-3' |
| 42PD-1 forward | 5'-CGGCC AGGAT GGTTC TTAGC CC-3' |
| PD-1 forward | 5'-CAGAC AGGCC CTGGA ACC-3' |
| PD-1 reverse | 5'-AGCTT GTCCG TCTGG TTGCT-3' |
| 14aPD-1 forward | 5'-CGGCC GCGGC GGCGG CGGCG GCCGC CGCGG CGGCG GCGGC CGCCC TGCTG CTGGT GACCG-3' |

TABLE S1-continued

Primer sequences used.

| Primer name | Sequences |
|---|---|
| 14aPD-1 reverse | 5'-CGGCC GCCGC CGCCG CGGCG GCCGC CGCCG CCGCC GCGGC CGCTA AGAAC CATCC TGGCC-3' |
| EL1 forward | 5'-AGGGC ATTCC AGAAA GATGA GGATA-3' |
| EL1 reverse | 5'-CCAAG TTGGA TGGGT CCTGG-3' |
| EL2 forward | 5'-GAGCT GTGGC AAGTC CTCAT ATCAA-3' |
| EL2 reverse | 5'-CCAAG TTGGA TGGGT CCTGG-3' |
| ED1 forward | 5'-GCA GTG GAG AAG GCG GCA CTC T-3' |
| ED1 reverse | 5'-CT GGC CGG CTG GCC TGG GTG-3' |

Real-time PCR for cytokine expression

Human

| hTNFa-f | 5'-CCG AGG CAG TCA GAT CAT CTT-3' |
|---|---|
| hTNFa-r | 5'-AGC TGC CCC TCA GCT TGA-3' |
| hiL6-f | 5'-GGT ACA TCC TCG ACG GCA TCT-3' |
| hiL6-r | 5'-GTG CCT CTT TGC TGC TTT CAC-3' |
| hiL1b-f | 5'-AAG CTG ATG GCC CTA AAC AG-3' |
| hiL1b-r | 5'-AGG TGC ATC GTG CAC ATA AG-3' |
| hu-IFN-b-f | 5'-AGC TGA AGC AGT TCC AGA AG-3' |
| hu-IFN-b-r | 5'-AGT CTC ATT CCA GCC AGT GC-3' |
| hu-IL-12-f | 5'-GGA CAT CAT CAA ACC TGA CC-3' |
| hu-IL-12-r | 5'-AGG GAG AAG TAG GAA TGT GG-3' |
| hIL-15F2 | 5'-GCA GGG CTT CCT AAA ACA GA-3' |
| hIL-15R2 | 5'-GTT GTT TGC TAG GAT GAT CAG-3' |
| hGAPDH f | 5'-ACA GTC CAT GCC ATC ACT GCC-3' |
| hGAPDH r | 5'-GCC TGC TTC ACC ACC TTC TTG-3' |

Murine

| TNF-a-FW | 5'-CAT CTT CTC AAA ATT CGA GTG ACA A-3' |
|---|---|
| TNF-a-RV | 5'-TGG GAG TAG ACA AGG TAC AAC CC-3' |
| mIL6-f | 5'-GTA GCT ATG GTA CTC CAG AGA C-3' |
| mIL6-r | 5'-ACG ATG ATG CA CTT GCA GAA-3' |
| mIL1a-f | 5'-TTC CAG GAT GAG GAC ATG AG-3' |
| mIL1a-r | 5'-TTG TTG TTC ATC TCG GAG CC-3' |
| b-actin-f | 5'-GTG GGC CGC TCT AGG CAC CA-3' |

TABLE S1-continued

Primer sequences used.

| Primer name | Sequences |
|---|---|
| b-actin-r | 5'-CGG TTG GCC TTA GGG TTC AGG GGG G-3' |

TABLE S2

Antibodies used.

| Antibody name | Company source |
|---|---|
| Monoclonal antibodies | |
| anti-human PD1 | |
| clone MIH4; FITC-conjugated | eBioscience |
| clone EH12.1; PE-conjugated | BD Bioscience |
| clone EH12.2H7 | BioLegend |
| Mouse anti-human PD-L1 | BioLegend |
| Mouse anti-human PD-L2 | BioLegend |
| FITC-anti-rabbit IgG | BioLegend |
| FITC-anti-mouse IgG | BioLegend |
| FITC-anti-goat IgG | Dakewe Biotech |
| For cell sorting from human PBMCs | |
| PE-anti-CD3 | eBioscience |
| FITC-anti-CD4 | eBioscience |
| APC/Cy7-anti-CD8 | eBioscience |
| PE/Cy7-anti-CD11c | eBioscience |
| PerCP-anti-CD14 | eBioscience |
| PerCP-anti-CD19 | eBioscience |
| APC-anti-CD56 | eBioscience |
| FITC-anti-CD68 | eBioscience |
| Polyclonal antibodies | |
| Goat anti-human PD1 | R&D Systems |
| Other antibodies | |
| Mouse IgG1k, iso control PE | eBioscience |
| AlexaFluor 488 | |
| donkey anti-goat IgG (H + L) | Invitrogen |
| AlexaFluor 647 | |
| goat anti-mouse IgG (H + L) | Invitrogen |

Cell Isolation and Gene Cloning.

Peripheral blood mononuclear cells (PBMCs) were freshly isolated from buffy-coats of anonymous healthy human blood donors using Ficoll-Hypaque (GE Healthcare). Human full-length PD1, PD-L1 and PD-L2 genes were amplified from PBMCs with respective primer pairs: PD1 forward/PD1 reverse, PD-L1 forward/PD-L1 reverse, and PD-L2 forward/PD-L2 reverse.

PCR Analysis of PR1 and Δ42PD1.

Cellular genomic DNA was extracted from human PBMCs using the QIAamp DNA Blood Kit (Qiagen). PD1 amplification from genomic DNA amplification used primer pair PD1D forward/PD1D reverse. Another primer pair (nPD1 forward/nPD1 reverse) flanks the deletion region to detect both PD1 and Δ42PD1 cDNA samples by PCR. All PCR products were electrophoresed in 2% agarose gel.

Quantitative Real-Time (qRT)PCR of Δ42PD1 Transcript Expression.

cDNA templates were generated using Superscript VILO Master Mix (Invitrogen) from total RNA extracted using RNAiso (Takara Bio Inc), followed by real-time PCR reactions performed with SYBR Premix Ex Taq II (Takara Bio Inc) with specific primer pairs (listed in Table S1) in the ViiA 7 instrument (Applied Biosystems) and analyzed with ViiA7 RUO software (Applied Biosystems) normalized to GAPDH (for human) or beta-actin (for murine) and untreated negative control.

DNA Plasmids and Fusion Proteins.

The extracellular domains of PD-L1 and PD-L2 were amplified from cDNA of human PBMC using primer pairs EL1 forward/EL1 reverse and EL2 forward/EL2 reverse, respectively. The extracellular domains (i.e. soluble forms) of PD1 and Δ42PD1 were amplified from the PD1 and Δ42PD1 genes using primer pair ED1 forward/ED1 reverse. The amplified ectodomains of PD1 and Δ42PD1, and PD-L1 and PD-L2 were inserted into the expression vector pVAX fused with the CH2-CH3 domain of rabbit IgG (Fc) in one open reading frame to generate $sPD1_{fc}$, $sΔ42PD1_{fc}$, $PD-L1_{fc}$ and $PD-L2_{fc}$, respectively.

The 14APD1 mutant was generated by an overlapping PCR-based technique to introduce a run of fourteen alanines into the deletion region using the primer pair 14aPD1 forward/14aPD1 reverse. Fusion DNA vaccine plasmids with HIV-1 Gag p24 insert alone or linked to human or murine sΔ42PD1 contain the CMV promoter and transcription led by the tPA signal sequence, which improves the adaptive immunogenicity of encoded antigen by DNA vaccines likely due to increased protein expression.

PD1 signal sequence is still intact in the construct, thus cleavage for protein translation does affect the overall fusion protein composition.

To increase the flexibility of the fusion protein, a linker GGGGSGGGG (SEQ ID NO:4) (nt sequence: GGTGGTG-GTTCAGGAGGAGGA) (SEQ ID NO:5) was applied between the sPD1 and HIV-1 p24 gene. Recombinant fusion proteins were produced by transient transfection of 293T cells using polyethylenimine (PEI) for 72 h and purified with protein-G agarose (Invitrogen), and quantified using a Micro BCA protein kit (Thermo Scientific). Endotoxin contamination was not detected in all protein preparations as tested by the E-TOXATE kit (sensitivity 0.03 EU/ml; Sigma-Aldrich).

Recombinant proteins were detected by Western blotting with specific antibodies and analyzed with Odyssey Infrared Imaging System (L1-COR Biosciences).

Molecular Modeling.

The model of human Δ42PD1 complex was built from the original PD1 crystal structure (PDB: 3B1K) using the INSIGHTII (Molecular Simulations, Inc., San Diego, Calif.), with the Δ42 deletion and beta-strands being highlighted.

Quantification of Cytokines.

$1×10^6$ PBMCs were treated with purified proteins of $sPD1_{fc}$, $sΔ42PD1_{fc}$ or rabbit Fc (20 μg/ml) or $1×10^6$ mouse splenocytes treated with $msΔ42PD1-p24_{fc}$, $msPD1-p24_{fc}$ or $p24_{fc}$ (20 μg/ml) or LPS (100 ng/ml). The concentration of 20 μg/ml is close to 6.7 μg/ml of sPD1 and 25 μg/ml of polyclonal anti-PD1 antibody to achieve their required in vivo effects.

Supernatants were then harvested for analysis of cytokine release using the Human or Mouse Th1/Th2 FlowCytomix multiplex kit (Bender MedSystems). Data were generated using FACSCalibur instrument (BD Biosciences) and analyzed by FlowCytomixPro software (Bender MedSystems).

Binding Characteristics of sPD1 Fusion Proteins.

293T cells transiently expressing human or murine PD-L1 and PD-L2 were incubated with 20 μg/ml of purified $sPD1_{fc}$, $sΔ42PD1_{fc}$, rabbit Fc, $msPD1-p24_{fc}$, $msΔ42PD1-p24_{fc}$ or $p24_{fc}$ proteins, and detected with anti-rabbit Fc conjugated antibody by flow cytometry.

Vaccination of Mice.

Figure 12:
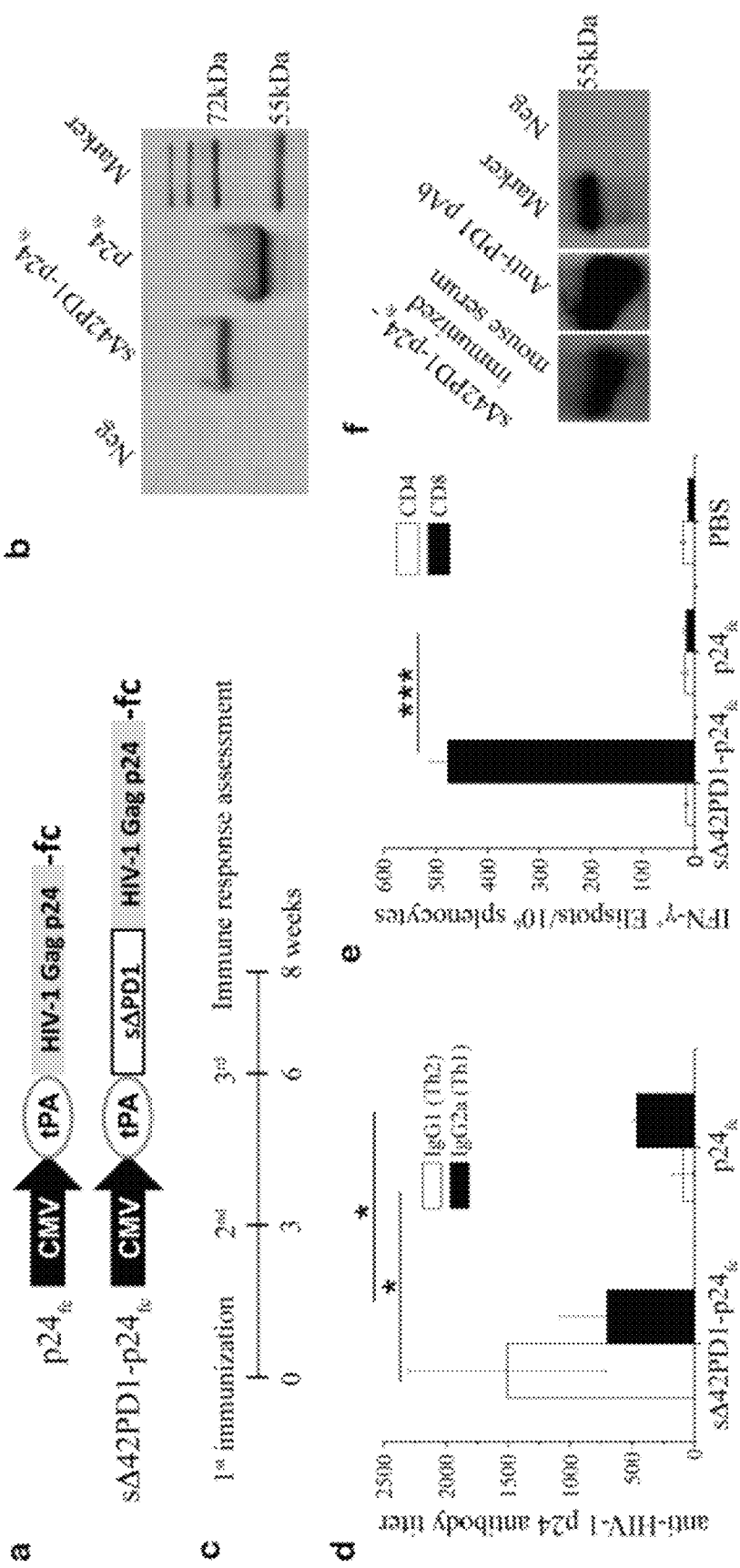
FIGS. 12A through 12F show that vaccination using human sΔ42PD1-p24$_{fc}$ fusion DNA elicited greater immune response.

All animal experiments received approval from the Committee on the Use of Live Animals in Teaching and Research, Laboratory Animal Unit, The University of Hong Kong. Female Balb/c mice at 5-8 weeks old were used for DNA immunization (or placebo PBS) by intramuscular (i.m.) injection with electroporation (EP) given every three weeks at a dose of 20 or 100 μg in 100 μl volume PBS per mouse for three times (FIG. 12C). Injection of 100 μl PBS alone served as the placebo group. Two weeks after the final immunization, mice were sacrificed, and sera and splenocytes were collected for immune response analysis. Each group contained 3-5 individual mice with independent immunization studies performed at least three times.

Cytokine Detection in Immunized Mice Sera

TABLE S3

Cytokine detection in immunized mice sera.

| Immunized mouse | IL-2 | IFN-□ | TNF-□ | IL-4 | IL-5 | IL-6 | IL-10 | IL17 | IL-1□ | GM-CSF |
| --- | --- | --- | --- | --- | --- | --- | --- | --- | --- | --- |
| $p24_{fc}$ | | | | | | | | | | |
| mouse 1 | 0 | 0 | 0 | 0 | 0 | 0 | 0 | 0 | 0 | 0 |
| mouse 2 | 0 | 0 | 0 | 0 | 20.56 | 0 | 0 | 0 | 0 | 0 |
| mouse 3 | 175.52 | 0 | 0 | 0 | 0 | 0 | 0 | 0 | 0 | 0 |
| $msPD1-p24_{fc}$ | | | | | | | | | | |
| mouse 1 | 0 | 0 | 0 | 0 | 24.18 | 0 | 0 | 0 | 0 | 0 |
| mouse 2 | 0 | 0 | 0 | 0 | 33.33 | 0 | 0 | 0 | 0 | 0 |
| mouse 3 | 0 | 0 | 0 | 0 | 0 | 0 | 0 | 0 | 0 | 0 |
| ms□42PD1-p24$_{fc}$ | | | | | | | | | | |
| mouse 1 | 0 | 0 | 0 | 0 | 37.06 | 0 | 0 | 0 | 0 | 0 |
| mouse 2 | 0 | 0 | 0 | 0 | 20.92 | 0 | 275 | 0 | 0 | 0 |
| mouse 3 | 0 | 0 | 0 | 0 | 0 | 0 | 0 | 0 | 0 | 0 |
| PBS | | | | | | | | | | |
| mouse 1 | 0 | 0 | 0 | 0 | 21.74 | 0 | 0 | 0 | 0 | 0 |
| mouse 2 | 0 | 0 | 0 | 0 | 21.74 | 0 | 0 | 0 | 0 | 0 |
| mouse 3 | 0 | 0 | 0 | 0 | 0 | 0 | 0 | 0 | 0 | 0 |

Numbers = concentration in pg/ml.

Antibody Responses.

Specific antibody responses were assessed by ELISA. Briefly, high affinity protein-binding ELISA plates (BD Biosciences) were coated with HIV-1 p24 protein (Abcam), and serially diluted mice sera were added, and antibodies were quantified by goat-radish peroxidase (HRP)-labeled anti-mouse IgG1 or IgG2a antibody (Sigma). Data acquired using VICTOR 1420 Multilabel Counter (PerkinElmer)>2 optical density over control was used for analysis.

Evaluation of HIV-1 Gag p24-Specific T Cell Responses.

ELISPOT (Millipore) was used to assess IFN-γ-producing T cells. Briefly, peptide gagAI (AMQMLKDTI (SEQ ID NO:6); specific for $CD8^+$ T cells) and peptide gag26 (TSN-PPIPVGDIYKRWIILGL (SEQ ID NO:7); specific for $CD4^+$ T cells) were used to stimulate cells for 20 h and added to IFN-γ ELISPOT plates, with PMA (500 ng/ml) and calcium ionocycin (1 µg/ml) as positive control, or media only as negative control.

Peptide pool consisting of 59-members of Gag p24 libraries (each peptide contains 15aa with 10aa overlap) were divided into 3 pools of 19-20 peptides that span from amino acids 1-87 (pool 1), 77-167 (pool 2) and 157-231 (pool 3) and used to assess epitopic breadth of T cell response.

Elispots were identified by an immunospot reader and image analyzer (Thermo Scientific). MHC class I $H2-K^d$-AMQMLKDTI (SEQ ID NO:6) (Beckman Coulter) tetramer was used to identify p24-specific $CD8^+$ T cell population. Flow cytometric data was acquired and analyzed on a BD Aria III flow cytometer (BD Biosciences).

T Cell Proliferation.

Splenocytes were isolated from immunized mice 30 weeks post-immunization, labeled with CFSE (5 µM; Invitrogen), and stimulated with p24 peptide pool (2 µg/ml; donated by NIH, catalog: 8117), anti-CD28 antibody (2 µg/ml; eBioscience), in the presence of bone marrow-derived (BM-)DCs at a ratio of 1 DC:10 splenocytes for 5 days. Positive control included anti-CD3 (2 µg/ml) and anti-CD28 antibodies (2 µg/ml). Surface staining occurred for CD3/CD4/CD8 T cell markers, and flow cytometry with FACSCalibur (BD Bioscience) was used to analyse CFSE proliferation signals on T cells.

Cytotoxicity Assay.

Splenocytes isolated from mice two weeks after the last vaccination served as effector cells. Effector cells were stimulated with p24 peptide pool (2 µg/ml) and anti-CD28 antibody (2 µg/ml; eBioscience) for 16 h before used. AB1 cell line (Cell Bank Australia) transduced to express HIV-1 Gag served as target cells. A luciferase reporter was also introduced to the AB1-HIV-1-Gag cells. Assay was performed according to manufacturer's instructions using the LIVE/DEAD® Cell-Mediated Cytotoxicity Kit (Invitrogen).

Briefly, target cells were pre-stained with DiOC and co-cultured with effector cells at varying ratios for 2 h before all cells were stained with propidium iodide (PI), and analyzed by flow cytometry. Percentage of dead cells was calculated by subtracting the percentage of $PI^+$ target only cells for each test sample.

Tumor Challenge

Mice were subcutaneously challenged with $5×10^5$ AB1-HIV-1-Gag cells. Briefly, a transfer vector pBABE-HIVgag/Luc was inserted with a CMV promoter and co-transfected with pCL packaging vector into 293T cells to produce virus particles. Retrovirus-containing supernatants were used to infect AB1 mesothelioma cells with puromycin selection and single clones were expanded. Following tumor challenge, in vivo images were taken twice a week to detect the intensity of luciferase on the flank of mice by Xenogen IVIS 100 in vivo imaging system.

Virus Challenge and Plaque Assay.

Mice three weeks post-vaccination were intranasally challenged using modified vaccinia virus that expresses HIV-1 gag and pol genes from attenuated strain TianTan (VTTgag-pol) (for 20 µg dose mice group) or virulent strain Western Reserve (WRgagpol) (for 100 µg dose mice group) at $4×10^7$ and $2×10^6$ PFUs, respectively.

Mice were sacrificed eight days post-challenge to determine virus titers in the lung homogenates, prepared by physical disruption, and cultured on Vero cell monolayer to monitor cytopathic effect over time. Body weight of WRgagpol infected mice were monitored daily for eight days prior to sacrifice.

Statistical Analysis.

All statistical analyses were performed using the paired two-tailed Student's t test. P values less than 0.05 were considered statistically significant. Data were presented as mean values±the standard error of the mean (SEM) of at least three independent experiments (and ≥3 mice per group per experiment) unless indicated.

Generation of Mouse Derived Monoclonal Antibodies Against Human Δ42PD1

Cell Culture.

SP2/0-Ag14 myeloma cells (ATCC, Ca. No. CRL-1581), 293T cells, and Human PD1 or Δ42PD1 stably expressing 293T cell lines (293T-PD1, 293T-Δ42PD1) were maintained in Dulbecco's modified Eagle's medium (DMEM) (Cat. No. 11995, Life Technologies) supplemented with 10% fetal bovine serum (FBS) plus 1/100 pen/strep (Cat. No. 15140, Life Technologies). DG-75 B cell line and Jurkat T cell line were maintained in RPMI 1640 supplemented with 10% heat-inactivated FBS, 2 mM L-glutamine and 1/100 pen/strep (1640 complete medium). All above-mentioned cells were maintained in a 37° C. humidified 5% CO2 incubator. Suspension-adapted HEK293 cells (FreeStyle™ 293-F) (Cat No. R79007, Life Technologies) were cultured in the serum-free FreeStyle™ 293-F Expression Medium (Cat. No. 12338-018, Life Technologies) in 37° C. incubator with a humidified atmosphere of 8% CO2 on an orbital shaker platform rotating at 135 rpm.

Expression and Purification of Recombinant Protein.

Recombinant proteins sΔ42PD1Fc, sPD1His and sΔ42PD1His were expressed using FreeStyle™ 293 Expression System. Briefly, fusion expressing plasmid pVAX-sΔ42PD1-Fc, pVAX-sΔ42PD1-His were used to transfect 293-F. Dilute 200 µg plasmid and 200 µg Polyethylenimine (PEI) in 8 ml Opti-MEM and mix gently, followed by incubating for 15 min at room temperature. Then the mixture was added into 200 ml 293-F cells (106 cells/ml). After 6 days culture, the fusion protein containing supernatant was collected and then purified using Recombinant Protein G (rProtein G) Agarose (Cat No. 15920-010, Life Technologies) (for sΔ42PD1Fc) and Dynabeads® His-Tag Isolation & Pulldown (Cat. No. 10103D, Life Technologies) (for sΔ42PD1His and sPD1His) respectively, following the manufactures' instructions. Plasmids used for protein preparation were previously constructed[25]. Concentrations and purity of proteins were determined by BCA Protein Assay Kit (Cat. No. 23227, Thermo Scientific) and Coomassie Brilliant Blue-stained SDS-PAGE respectively.

Immunization and Cell Fusion.

All animal experiments received approval from the Committee on the Use of Live Animals in Teaching and Research, Laboratory Animal Unit, The University of Hong Kong, Hong Kong SAR, China. For immunization, 100 µg s442pd1$_{fc}$ plasmid in 50 µl PBS was injected intramuscularly (i.m.) in the quadriceps of female BABL/c mouse (8-10 weeks of age) on week 0 and J. Immediately following injection, electroporation (EP) was performed at the injection site using a 2-needle array with a 0.5 cm gap. Electroporation parameters were: 120 V/cm distance between the electrodes; 50-ms pulse length; 6 pulses, given by a TERESA (Shanghai Teresa Healthcare) generator. After DNA plus EP priming, 20 μg sΔ42PD1Fc proteins emulsified in Freund's complete adjuvant was immunized subcutaneously on week 6, followed by 20 μg immunogen in Freund's incomplete adjuvant subcutaneously on week 9. Mice serum were collected seven days after the forth immunization for ELISA and Flow cytometry. Hybridoma producing monoclonal antibodies (mAbs) against human Δ42PD1 were generated as described by Kohler and Milstein. At day 7 following the last boosting, 1.5×108 spleen cells of the immunized mice were collected and fused with SP 2/0 myeloma cells at a ratio of 10:1 using Polyethylene glycol solution (Cat. No. P7181, Sigma). Hybridoma cells were selected in HAT medium (DMEM supplemented with 20% FBS and 2% HAT) for 10 days and then switched to HT medium (DMEM supplemented with 20% FBS and 1% HT).

Indirect ELISA.

For hybridoma screening, two weeks after fusion, supernatants were tested for specific antibody production by indirect ELISA. Briefly, 100 μl sΔ42PD1His (0.2 μg/ml) was coated in 96-well plates overnight at 4° C. The wells were then washed three times with phosphate buffer solution containing 0.1% Tween-20 (PBS-T), and blocked with 200 μl of PBS containing 4% nonfat milk at 37° C. for 1 h. After washing, supernatants (100 μl/well) were added to the plates and incubated for 1 h at 37° C. After three times washing, 100 μl per well of Goat anti-Mouse IgG H&L (HRP) secondary antibody (Cat. No. ab97040, Abcam) diluted 1:50,000 was added to plates. Then plates were incubated at 37° C. for 1 h. After extensive washes, the enzymatic reaction was developed with 3,3',5,5'-tetramethylbenzidine (TMP) liquid substrate (Cat. No. T4444, Sigma) and stopped by adding 0.2 M H2SO4. The optical density was measured at 450 nm (O.D.450 nm) with a VICTOR3 1420Multilabel Counter (Perkin-Elmer).

Flow Cytometry and Antibodies.

For indirect staining, cells were initially incubated with mouse serum, hybridoma supernatant or purified monoclonal antibodies followed by staining with Alexa Fluor® 647 Goat anti-Mouse IgG (H+L) (Cat. No. A-21235, Life Technologies) after washing with FACS buffer (PBS with 2% FBS and 0.1% NaN3). For direct staining, cells were incubated with fluorescence-labeled mAbs or isotype-matched negative control Abs; or for intracellular staining, cells were fixed and permeabilized using Fixation/Permeabilization Solution Kit (Cat. No. 554714, BD Biosciences) according to the manufacturer's instructions. All the stained tubes were incubated for 15 min at room temperature. Cells were resuspended in 0.4 ml PBS and then subjected to FACSCalibur or FACSAria III Flow Cytometer (BD Biosciences), and data were analyzed with FlowJo software.

Labeled anti-human antibodies used in current research include Pacific Blue-CD3 (clone UCHT1, 558117, BD Pharmingen), FITC-CD11c (clone 3.9, 301603, Biolegend), PE-Cy7-CD14 (clone 61D3, 25-0149-42, eBiosciences), PerCP-CD19 (clone 340421, BD Bioscience), Alexa Fluor 488-CD56 (clone HCD56, 318312, Biolegend), PerCP-Cy5.5-HLA-DR (clone L243, 307630, Biolegend), PE-PD1 (clone EH12.1, 560795, BD Pharmingen), Alexa Fluor 647-Δ42PD1 (clone CH101, clone CH34), Alexa Fluor 647-IgG1 (clone MG121, Invitrogen), Alexa Fluor 647-IgG2b (clone MPC-11, 400330, Biolegend), PE-IgG1 (clone MOPC-21, 400112, Biolegend).

Isolation of PBMCs

Peripheral blood mononuclear cells (PBMCs) were isolated by density gradient centrifugation using Ficoll-paque premium (Cat. No. 17-5442-02, GE Healthcare) from fresh healthy blood donors. Briefly, whole blood was diluted 1:4 with sterile PBS and centrifuged at 400×g for 30 min without brake. The isolated PBMCs were washed twice with PBS at 200×g for 5 min. After washing, the cells were counted and resuspended in pre-warmed 1640 complete medium at a concentration of 2×106 cells/ml.

Surface Plasmon Resonance

Binding avidity analyses were performed with a Biacore ×100 optical biosensor (GE Healthcare). Immobilization of recombinant sΔ42PD1FC to CM5 sensor chip was performed following the standard amine coupling procedure. Concretely, carboxyl groups on the sensor chip surface was activated by injection of N-Hydroxysuccinimide (NHS) and 1-Ethyl-3-(3-dimethylaminopropyl) carbodiimide hydrochloride (EDC) in Amine Coupling Kit (Cat No. BR-1000-50, GE Healthcare). Then recombinant sΔ42PD1FC at a concentration of 30 μg/ml in 10 mM sodium acetate buffer (pH 5.0) was allowed to flow over the chip surface at a rate of 5 μl/min for 7 min, and the final response bound turned out to be 7379 RU. After unreacted protein was washed out, excess active ester groups on the sensor surface were capped by injection of 1 M ethanolamine (pH 8.5) at a flow rate of 5 μL1/min for 7 min. As background to correct instrument and buffer artifacts, a reference was generated under the same conditions without immobilization the recombinant protein. Binding experiments were performed at 25° C. in HBS-EP buffer (Cat No. BR-1006-69, GE Healthcare). Binding kinetics were analyzed by passing various concentrations of anti-human Δ42PD1 mAbs CH34 and CH101 over the chip surface for 3 min. Dissociation of bound analytes was monitored while the surface was washed with buffer for 4 min at a flow rate of 30 μL1/min. Remaining analytes were removed in the surface regeneration step with injection of 10 mM glycine-HCl (pH 2.0) for 2×30 sec at a flow rate of 30 μl/min. The kinetic parameters were determined after subtraction of the blank cell from each response value, by collectively fitting the overlaid sensograms locally using Biacore ×100 Evaluation software (version 2.0.1) to the 1:1 Langmuir binding model.

Cell Surface Δ42PD1 Signaling Assay

To determine antagonist activity of Δ42PD1 specific monoclonal antibodies, $1×10^5$ cells were centrifuged at 200×g for 5 min and resuspended with 100 μL1 PBS containing 1 μg purified Δ42PD1 specific monoclonal antibodies or isotype matched control antibodies, cells were incubated at room temperature for 10 min, then PBMCs were added with a ratio of 1:50 followed by centrifugation at 200×g for 5 min and resuspension with 100 μL1 DMEM complete media. Then cells were incubated at room temperature for 15 min, followed by intracellular staining of p-Akt and flow cytometrical analysis.

Double-Antibody Sandwich-ELISA

Microtiter plates (Cat. No. 3690, Corning) were coated with antibody CH34 (10 μg/ml) at 37° C. for 2 h followed by incubating with PBS containing 4% skim milk to block nonspecific binding. Plasma or serum specimens were diluted at 1/2 and added to wells in duplicate, along with recombinant 42PD1FC proteins as standards. The plates were then incubated for 2 h at 37° C. After washing, biotin labeled antibody CH101 (5 μg/ml) (labeled using Biotin Protein Labeling Kit, Cat. No. D-20655, Life Technologies) were added and incubated for an additional 2 h at 37° C. Following the addition of horseradish peroxidase (HRP) conjugated Streptavidin (Cat. No. SΔ10001, Life Technologies) (1:2000), color reactions were developed using 3,3',5,5'-tetramethylbenzidine (TMB) liquid substrate (Cat. No. T4444, Sigma) and subsequently stopped with 0.2 M H2SO4. The optical density was measured at 450 nm (O.D.450 nm) with a VICTOR3 1420 Multilabel Counter (Perkin-Elmer).

EXAMPLES

Following are examples that illustrate procedures and embodiments for practicing the invention. The examples should not be construed as limiting.

Example 1—Novel PD1 Isoform

To investigate the polymorphism of PD1 gene, mRNA transcripts from PBMCs from 25 human healthy donors are examined. In one representative donor with seven clones, T-PCR and sequence analysis showed that six clones harbored an identical isoform of PD1, which consists of a 42-base pairs deletion from the start of exon 2 that is equivalent to a 14 amino acid in-frame deletion (DSPDRPWNPPTFFP) (SEQ ID NO:3) (FIGS. 1A and 1B). The PD1 isoform was as designated as Δ42PD1.

To verify that this deletion is not due to intrinsic genomic defect from multiple donors, PCR was performed using primers that flank the deleted region. As a control, genomic DNA only detected wildtype PD1 (FIG. 1C, lanes 1-7, lower gel), while both wildtype PD1 and Δ42PD1 transcripts were readily detected from cDNA generated from five out of seven donor PBMCs (FIG. 1C, lanes 1-7, upper gel), which are confirmed by sequence analysis. Hence, this transcript isoform is likely due to alternative splicing, and not mutation on the chromosomal level. Alternative splicing of pre-mRNA is usually found in mammalian cells under two conditions: mutation of the junction site between introns and exons, or alternative selection of splicing sites.

For the latter, an AG dinucleotide splicing donor is often required, and indeed, there exists an alternative AG splicing donor at the 3' terminus of the deletion region of exon 2 that probably leads to the formation of the Δ42PD1 mRNA (FIG. 1B). In total, 24 out of 25 donors harbored the Δ42PD1 isoform.

To determine the expression profile of Δ42PD1 among immune cells found in PBMCs, quantitative real-time RT-PCR with the use of specific primers was performed to measure the mRNA expression of Δ42PD1 in different cell types.

For this purpose, cell sub-populations were sorted from PBMCs from five independent healthy donors according to various cell markers: NK cells (CD3$^-$CD56$^+$), T cells (CD3$^+$), CD3$^+$CD4$^+$ T and CD3$^+$CD8$^+$ T cells, B cells (CD3$^-$CD19$^+$), NKT cells (CD3$^+$CD56$^+$), monocytes (CD3$^-$CD11c$^-$CD14$^+$), macrophages (CD3$^-$CD11c$^-$CD68$^+$), and dendritic cells (DCs; CD3$^-$CD11c$^+$). As shown in FIG. 1D, the relative expression of Δ42PD1 was found highest among monocytes, macrophages, NK and NKT cells, and to a lesser extent on B cells, T cells (CD4 or CD8) and DCs. Δ42PD1 is distinct from PD1 and does not interact with PD-L1/L2.

To gain a better understanding of the possible function of Δ42PD1, DNA plasmid vectors were generated to express soluble forms of PD1 or Δ42PD1 protein tagged to rabbit Fc, denoted as sPD1$_{Fc}$ and sΔ42PD1$_{Fc}$, respectively. Soluble forms of PD1 or Δ42PD1 protein only encode the extracellular regions and the former has been used to characterize the function of PD1 previously.

Figure 10:
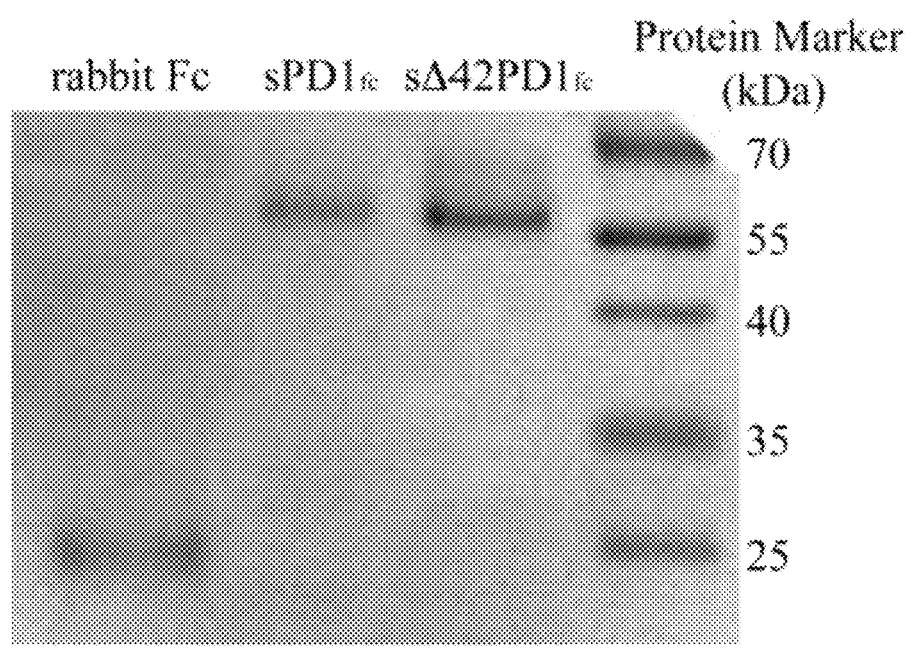
FIG. 10 shows purity of recombinant proteins. Supernatants were collected from 72 h post-transfected 293T cells of plasmids encoding rabbit Fc, sPD1$_{fc}$ or sΔ42PD1$_{fc}$, and purified using Protein G agarose. Purified proteins were electrophoresed on SDS-PAGE gel and stained with Coomassie Blue to show a single band corresponding to the encoded protein size.

In addition, to account for tertiary structural disruptions with the deleted 14 amino acids, alanines are substituted back to generate s14APD1$_{Fc}$. Purified proteins of sPD1$_{Fc}$, sΔ42PD1$_{Fc}$ and s14APD1$_{Fc}$ were generated by transient transfection of 293T cells with subsequent purification from culture supernatants. The purity of these proteins was checked by Coomassie blue-stained SDS-PAGE gel electrophoresis (FIG. 10).

Figure 2:
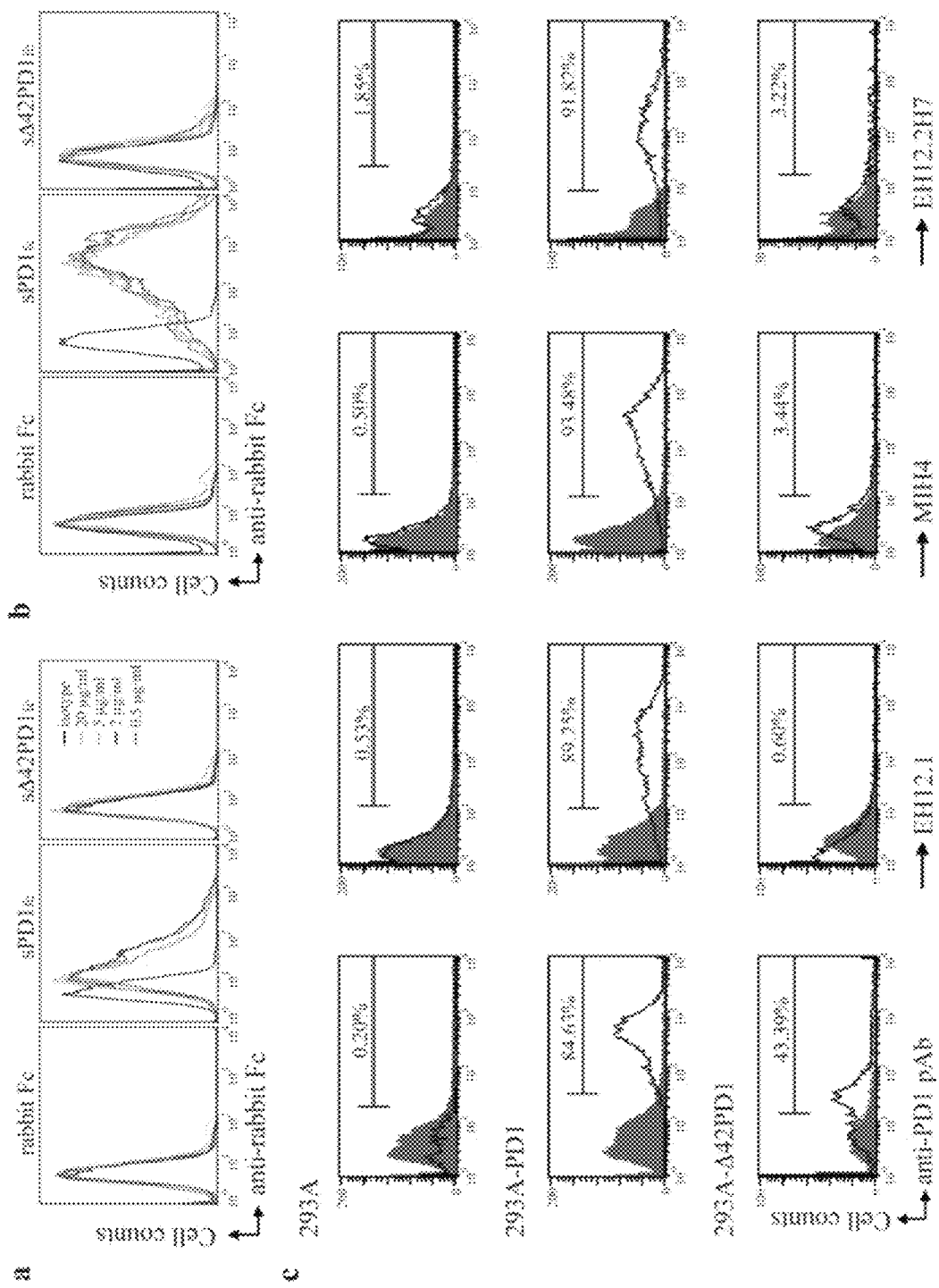
FIGS. 2A through 2C show characterization of the function of Δ42PD1 isoform.

To determine if these proteins could bind to PD1 ligands, they were used to treat 293T cells transiently transfected with human PD-L1 or PD-L2 at different concentrations, and signals from binding were detected by anti-rabbit Fc antibody using flow cytometry (FIGS. 2A and 2B). As expected, sPD1$_{Fc}$ was bound to both PD-L1 and PD-L2, but neither to sΔ42PD1$_{Fc}$ nor to s14APD1$_{Fc}$.

The results show that the protein encoded by the Δ42PD1 isoform is unlikely to interact with PD1 ligands and the 14 alanines were insufficient to restore the binding.

Figure 2C:
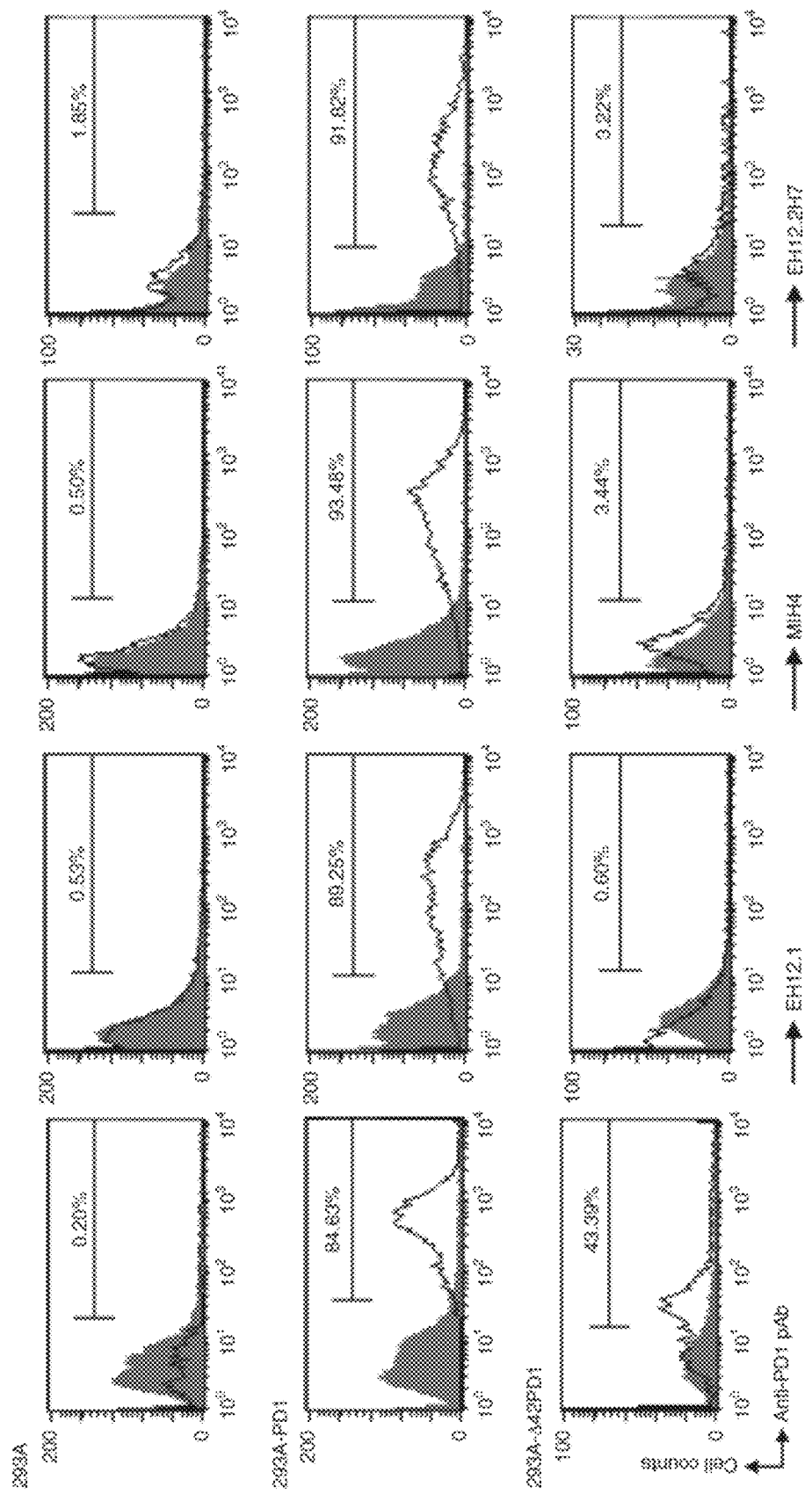

To demonstrate that Δ42PD1 and PD1 are distinct molecules, the full-length membrane-bound form of Δ42PD1 and PD1 are expressed by stable transfection of 293A cell line (293A-PD1 and 293A-Δ42PD1) and commercial antibodies were used for detection by flow cytometry. PD1-specific monoclonal antibodies (clones EH12.1, MIH4, and EH12.2H7) detected PD1 but were unable to detect Δ42PD1 (FIG. 2C). As these commercial antibodies bind to the PD1/PD-L interacting moieties, these results further reinforce that Δ42PD1 differs from PD1 structurally at the PD-L binding interface. Commercial polyclonal anti-PD1 antibody could detect both PD1 and Δ42PD1 (FIG. 2C), suggesting that Δ42PD1 could still be recognized, likely through a region conserved between PD1 and the Δ42PD1 isoform outside the PD-L binding interface.

These results indicate that the conformation of this Δ42PD1 isoform differs from PD1 primarily at the domain of PD-L1/L2 interaction.

Figure 7:
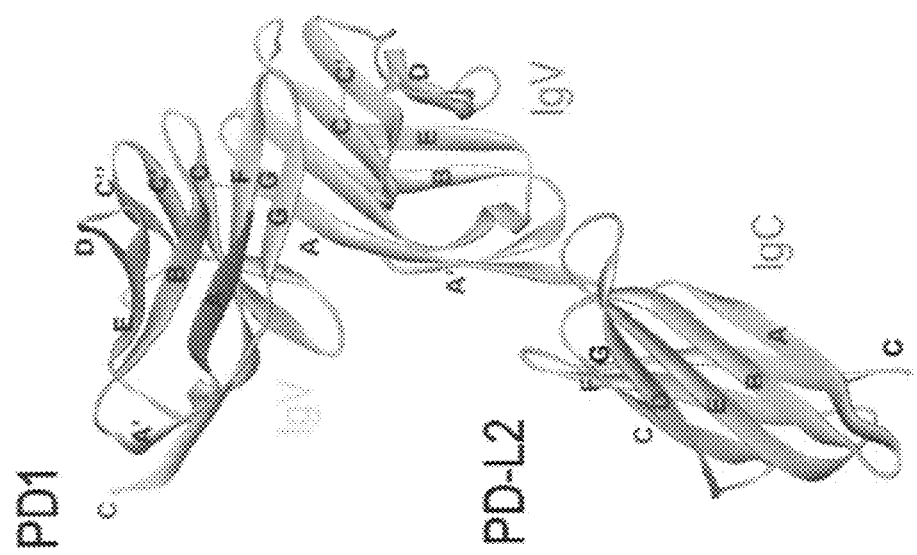
FIG. 7 shows schematic representation of Δ42 deletion on human PD1 in complex with PD-L2. Protein structure modeling of human PD1 based on the published crystal structure, but including 10 more amino acids upstream of beta-strand A to include the range of the Δ42 deletion (red). Other beta-strands are labeled for PD1 and PD-L2.

This Example also examines the structure of Δ42PD1 in silico. As the 14-amino acid deletion partially exists in the published PD1 crystal structure, the inventors re-modeled human PD1 and included the initial 14-amino acids in the structure in the beta-strand A of human PD1 (FIG. 7; highlighted red). Based on the model, the deletion of the N-terminal beta-strand A, which extensively interacts with the core structure, could result in a conformation that is distinct from the correct folding of wildtype PD1, and thus renders Δ42PD1 unable to bind to PD-L1/L2.

Example 2—Δ42PD1 Induces the Production of Pro-Inflammatory Cytokines in Human PBMCS This Example investigates the function of Δ42PD1 using the purified sΔ42PD1$_{Fc}$ proteins to treat human PBMCs and measured the production of cytokines.

Briefly, PBMCs were treated with purified sPD1$_{Fc}$, sΔ42PD1$_{Fc}$ or rabbit Fc recombinant proteins for 24 h, and supernatants were collected to determine the cytokine release profile by a multiplex assay. Untreated cells or LPS served as negative and positive controls, respectively.

Figure 3A:
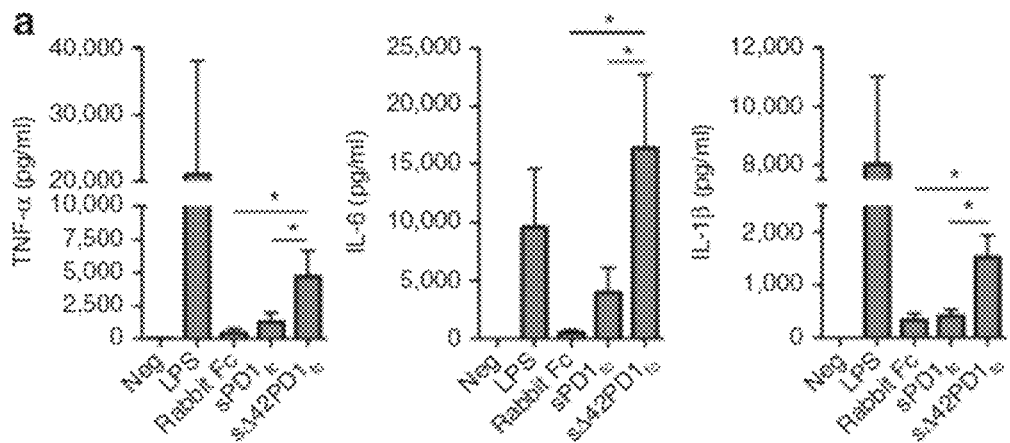
FIGS. 3A through 3D show functional analysis of human sΔ42PD1 in vitro.

As shown in FIG. 3A, PBMCs treated with sΔ42PD1$_{Fc}$ had significantly higher levels of TNF-α, IL-6 and IL-1β cytokine production, when compared to sPD1$_{Fc}$ or rabbit Fc. Other cytokines IFN-γ, IL-2, IL-4, IL-5, IL-8, IL-10, IL-12p70 and TNF-β were not detected following treatment by these recombinant proteins (data not shown).

Figure 3B:
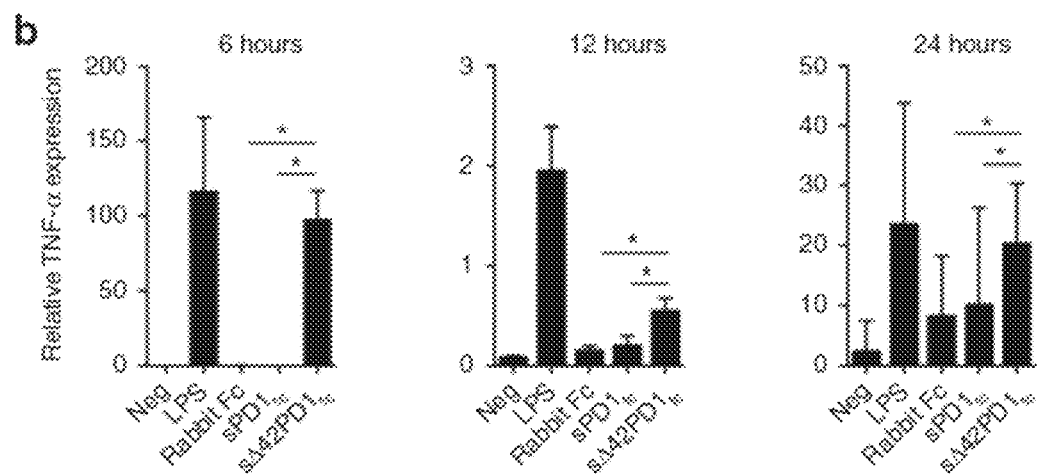
Figure 3C:
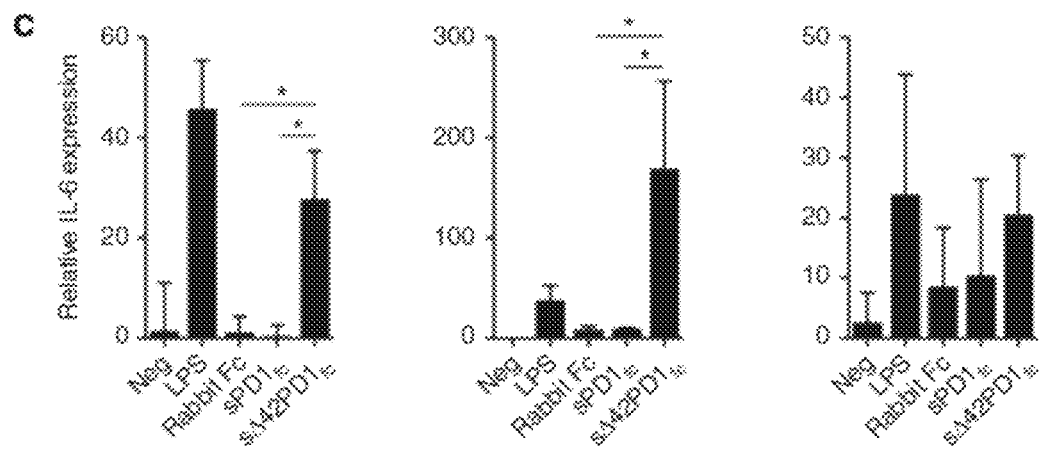
Figure 3D:
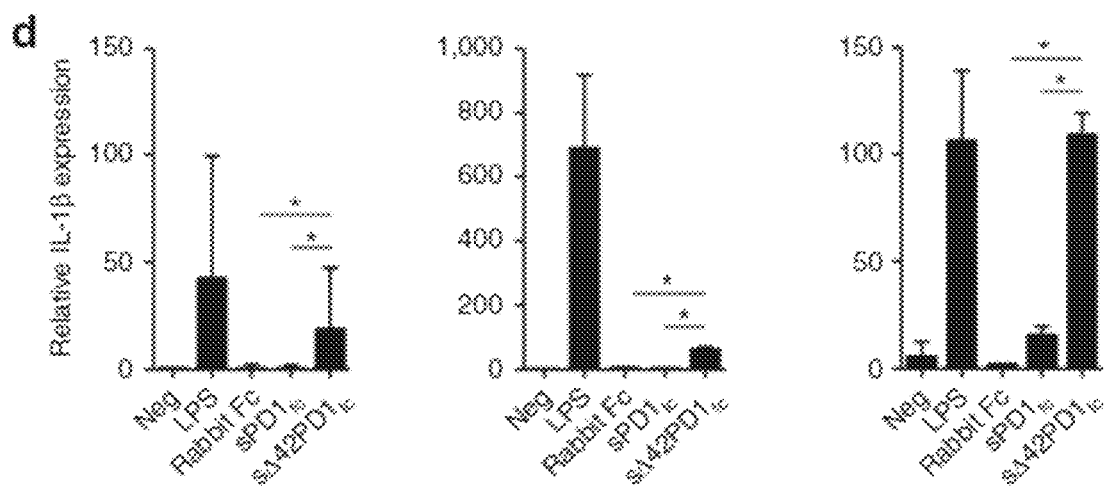

For verification, quantitative real-time PCR was performed at 6 h, 12 h and 24 h post-treatment of PBMCs, and relative mRNA expression of TNFα, IL6, and IL1β was also found significantly increased with sΔ42PD1$_{Fc}$ protein treatment compared with sPD1$_{fc}$ that remained at levels comparable to rabbit Fc (FIGS. 3B through 3D).

Moreover, another version of recombinant protein in which soluble Δ42PD1 was fused with a 6×His tag named sΔ42PD1His was also used to treat PBMCs, and successfully induced production of pro-inflammatory cytokines in a dose dependent manner (FIGS. 28A and 28B).

Figure 11:
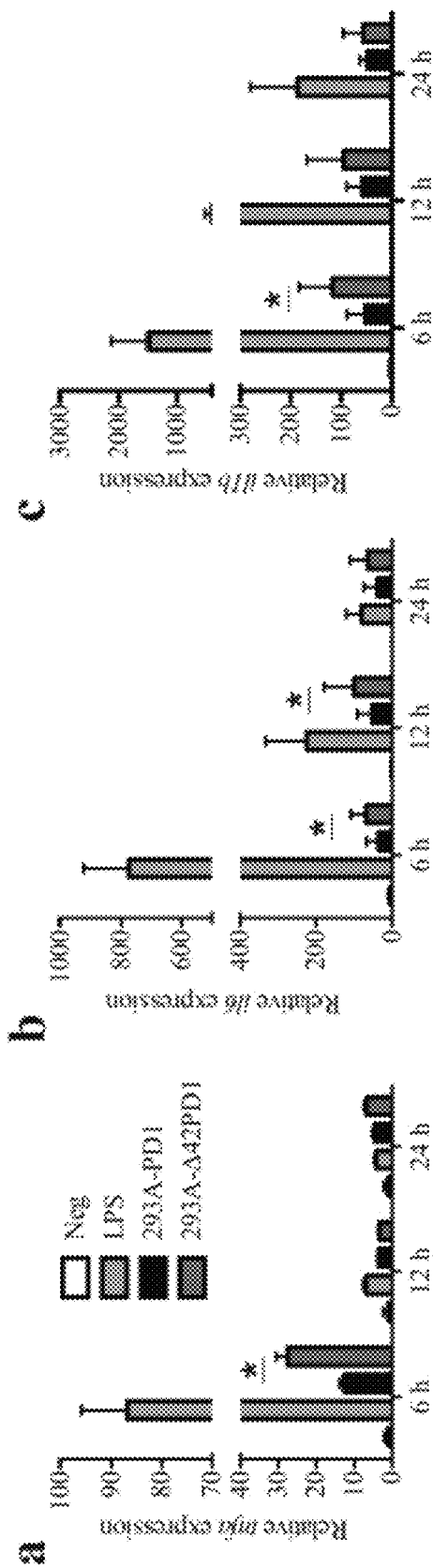
FIGS. 11A through 11C show that membrane-bound Δ42PD1 can induce pro-inflammatory cytokines from PBMCs. Stably transfected 293A cells expressing PD1 or Δ42PD1 were γ-irradiated (50 Cy) then added to freshly isolated PBMCs at 1:1 and real-time PCR was performed on cells harvested at 6 h, 12 h, and 24 h after co-culture to assess the expression of (FIG. 11A) TNFα, (FIG. 11B) IL6 and (FIG. 11C) IL1b normalized to GAPDH and untreated control (Neg). *P<0.05.

In addition, to confirm that not only the soluble form can induce such effects, cytokine induction is also examined using γ-irradiated 293A cells stably expressing surface PD1 or Δ42PD1 and co-cultured with PBMCs, and the same trend as with using the soluble form of proteins at least for the 6 h time point after treatment was observed (FIGS. 11A through 11C).

The results show that both soluble and membrane-bound Δ42PD1 could induce the production of pro-inflammatory cytokines.

Subsequently, human and mouse sΔ42PD1 nucleic acid molecules were used as an intramolecular adjuvant to develop a fusion DNA vaccine with HIV-1 Gag p24 antigen (sΔ42PD1-p24) to immunize mice, and the fusion DNA vaccine elicited a significantly enhanced level of anti-p24 IgG1/IgG2a antibody titers, and important p24-specific CD8+ T cell responses that lasted for more than 7.5 months. Furthermore, p24-specific CD8+ T cells possess functionally improved proliferative and cytotoxic capacities resulting in the protection of immunized mice against pathogenic viral challenge.

The results show that Δ42PD1 has an immune regulatory function distinct from PD1.

Example 3—Δ42PD1 Fused to Antigen Promotes Specific Adaptive Immunity In Vivo

As TNF-α, IL-6 and IL-1β have cooperative and key roles in the generation of adaptive immunity, this Examples investigates whether Δ42PD1 can perform this function in vivo.

Briefly, a fusion DNA vaccine construct comprised of HIV-1 Gag p24 is generated for use as the target immunogen with human sΔ42PD1 tagged to rabbit Fc (sΔ42PD1-p24$_{fc}$; FIG. 12A); DNA encoding p24$_{fc}$ is used as control. The rabbit Fc used only contains the CH2-CH3 domain and thus does not bind to rabbit Fcγ receptor. The tPA-leader was fused with the leader sequence of PD1 to increase protein release, while the signal peptide cleavage of Δ42PD1 remains the same as wildtype PD1. Expression of their encoded protein was confirmed by Western blotting (FIG. 12B).

The DNA vaccine constructs were delivered at a dose of 20 μg/shot to Balb/c mice intramuscularly (i.m.) with electroporation (EP) according to our previously used immunization regimen (FIG. 12C).

As shown in FIG. 12D, antibody responses detected in mice sera by ELISA for both IgG2a (Th1; 1.5-fold) and IgG1 (Th2; 7-fold) raised against p24 were significantly higher ($P<0.05$) in mice immunized with sΔ42PD1-p24$_{fc}$ than p24$_{fc}$. For T cell responses, IFN-γ-producing cells were measured using ELISPOT assay against Gag peptides specific for CD4+ (gag26) and CD8+ (gagAI) T cells. Almost 10-fold greater number of IFN-γ+ Elispots for gagAI-specific CD8+ T cells were detected in splenocytes of sΔ42PD1-p24$_{fc}$-immunized mice compared to p24$_{fc}$-immunized group ($P<0.001$) or placebo (PBS). However, gag26-specific CD4+ Elispots remained low and there were no differences between the two immunized groups or placebo (FIG. 12E).

Immunization with human sΔ42PD1 fused to p24$_{fc}$ elicited a substantial level of CD8+ T cell response and modest antibody responses against p24, indicating a functional role of human sΔ42PD1 in DNA vaccination in mice.

To determine whether human sΔ42PD1 could be immunogenic in mice due to sequence diversity, the inventors examined whether immune recognition and response have been directed against human sΔ42PD1. Indeed, mouse serum from sΔ42PD1-p24$_{fc}$-immunized mice recognized Δ42PD1-GST purified protein by Western blotting (FIG. 12F), indicating that anti-human Δ42PD1 immunity may have interfered with the generation of anti-p24 immune response.

Example 4—Murine SΔ42PD1 Fusion DNA Vaccine Elicits an Enhanced Level of Antigen-Specific CD8+ T Cell Immunity in Mice The murine version of fusion DNA construct was generated by substituting human sΔ42PD1 with murine (m)sΔ42PD1 with deletions at the same nucleotide positions to generate msΔ42PD1-p24$_{fc}$. While the native Δ42PD1 isoform was not detected in splenocytes of Balb/c or C57BL6/N mice by RT-PCR and sequencing (data not shown), the equivalent (m)sΔ42PD1 isoform was used to study the efficacy of our DNA fusion vaccine strategy in mice.

Figure 13:
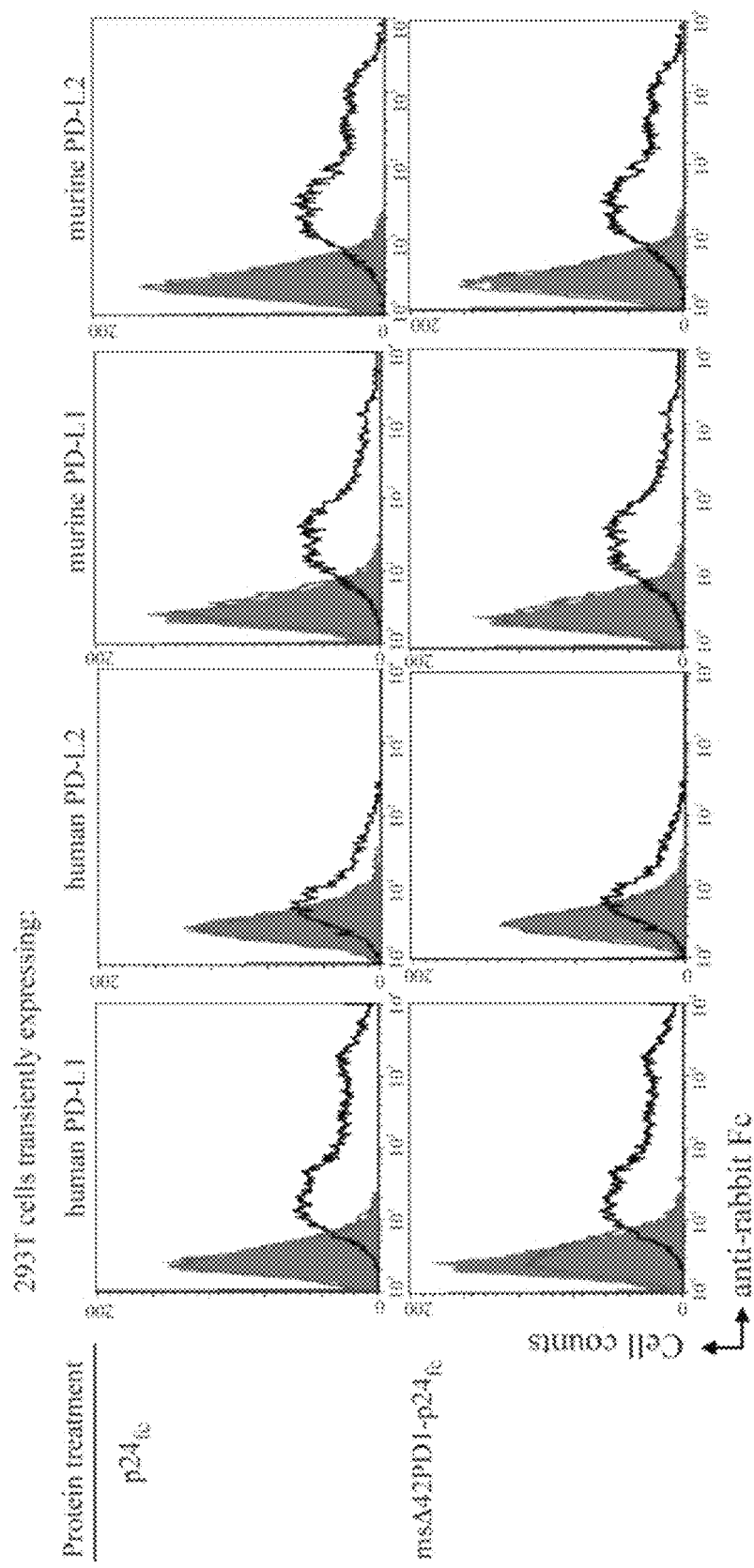
FIG. 13 shows that murine sΔ42PD1 does not interact with PD-L1/L2. Binding of murine (m)sΔ42PD1-p24$_{fc}$ recombinant protein were examined by treating transiently transfected 293T cells expressing human or murine PD-L1 or PD-L2. p24$_{fc}$ was used as a control. Positive staining (solid black lines) was achieved by conjugated monoclonal antibodies. Negative staining (shaded) represents isotype control. Red lines show anti-rabbit Fc detection antibody signal if binding of proteins occurred. Data acquired and analyzed by FACSCalibur flow cytometer and CellQuest software (BD Biosciences).

To verify the function of murine counterparts, recombinant msΔ42PD1-p24$_{fc}$ proteins were generated and tested for binding to PD-L1/L2 expressed on transiently transfected 293T cells (FIG. 13). msΔ42PD1-p24$_{fc}$ or p24$_{fc}$ did not bind to either human or murine PD1 ligands.

Figure 14:
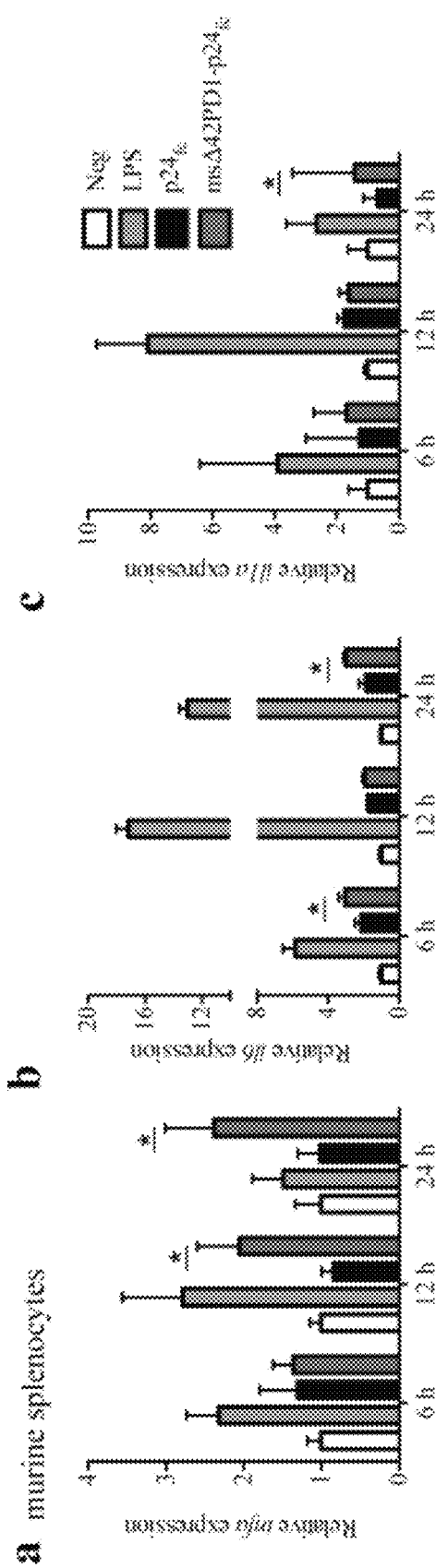
FIGS. 14A through 14C show that msΔ42PD1-p24$_{fc}$ recombinant protein can induce pro-inflammatory cytokines from murine splenocytes. qRT-PCR analysis of (FIG. 14A) TNFa, (FIG. 14B) IL6, and (FIG. 14C) IL1a expression in freshly isolated murine splenocytes following treatment of recombinant purified proteins (20 μg/ml) or LPS (0.1 μg/ml)

To investigate whether the recombinant msΔ42PD1-p24$_{fc}$ protein could induce pro-inflammatory cytokines, splenocytes from Balb/c mice were treated with purified proteins msΔ42PD1-p24$_{fc}$ or p24$_{fc}$. The results show that an increased level (~2-fold) of mRNA expression of tnfa from 12 h and 24 h post-treatment was significantly induced by msΔ42PD1-p24$_{fc}$ protein compared to p24$_{fc}$ ($P<0.05$; FIG. 14A). For IL-6 and IL-α, a modest but statistically significant elevated level of gene expression was detected at 6 h (~1.3-fold; $P<0.05$) and 24 h (~1.6-fold; $P<0.05$) (FIG. 14C).

However, the release of these cytokines 24 h post-treatment did not reach any significant differences compared to control (data not shown). Given the heterogeneity of splenocytes, bone marrow-derived dendritic cells (BM-DCs) were isolated and cultured to perform the same experiment. As shown in FIG. 4A, higher level of pro-inflammatory cytokines TNF-α (~3-fold), IL-6 (~1.5-fold) and IL-1a (~5-fold) were produced by msΔ42PD1-p24$_{fc}$-treated BM-DCs compared to p24$_{fc}$. Same as human sΔ42PD1$_{fc}$, msΔ42PD1-p24$_{fc}$ can also stimulate the expression of pro-inflammatory cytokines and the p24 antigen was not a contributing factor for this induction.

In vivo vaccination experiments were performed to determine if a higher level of antigen-specific immunity could be achieved compared to the human sΔ42PD1 counterpart using the same immunization regimen (FIG. 12C), but with two different doses (20 μg and 100 μg DNA/shot). Antibody responses show significantly higher level of IgG1 (Th2) and IgG2a (Th1) in sera of mice vaccinated with 20 μg of msΔ42PD1-p24$_{fc}$ compared to p24$_{fc}$ (3- and 4-fold, respectively; $P<0.05$; FIG. 4B), which was further amplified at the 100 μg dose. Unlike human sΔ42PD1-p24$_{fc}$, no immune response was raised against the msΔ42PD1 portion of the fusion molecule msΔ42PD1-p24$_{fc}$, as immunized mouse serum did not detect msΔ42PD1 protein by Western blotting (FIG. 15).

Figure 4C:
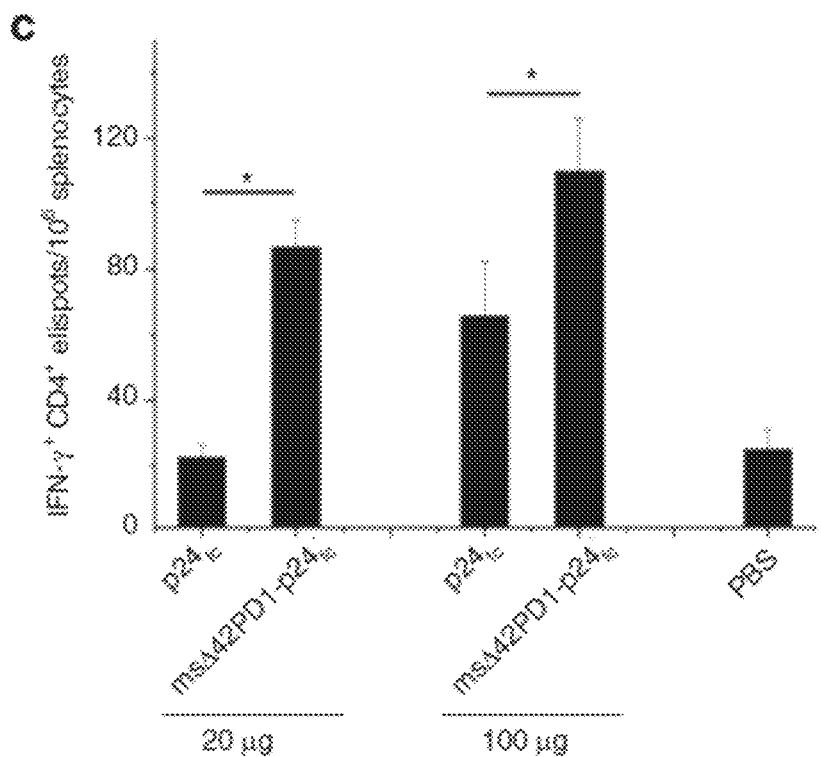
Figure 4D:
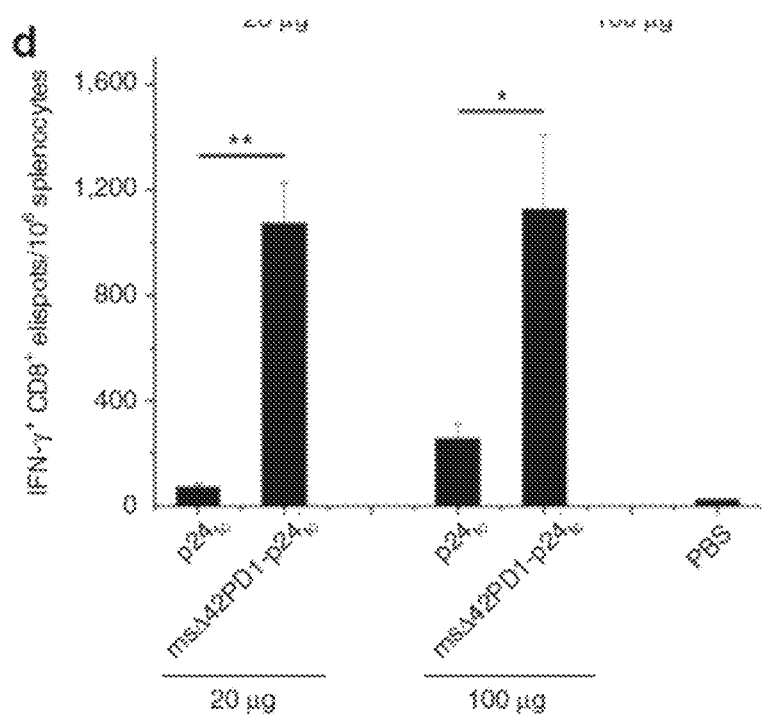
Figure 4E:
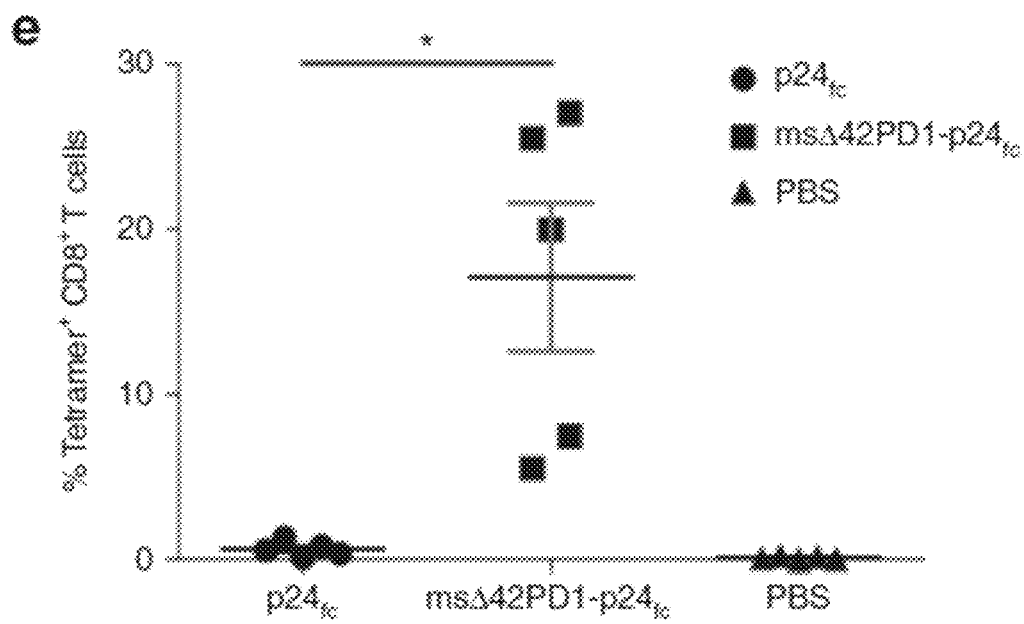

Meanwhile, IFN-γ ELISPOT assay detected a significantly increased level of p24-specific CD4$^+$ T cell responses (~100 Elispots/10$^6$ splenocytes; ~3.5-fold) and CD8$^+$ (~1000 Elispots/10$^6$ splenocytes; ~15-fold) from mice vaccinated with 20 μg dose msΔ42PD1-p24$_{fc}$ compared to p24$_{fc}$ or placebo (FIGS. 4C and 4D). However, no significant improvement was found in mice vaccinated at 100 μg dosage, which suggests that a low dose of msΔ42PD1-p24$_{fc}$ was sufficient to achieve this level of IFN-γ$^+$ T cell response.

Figure 4F:
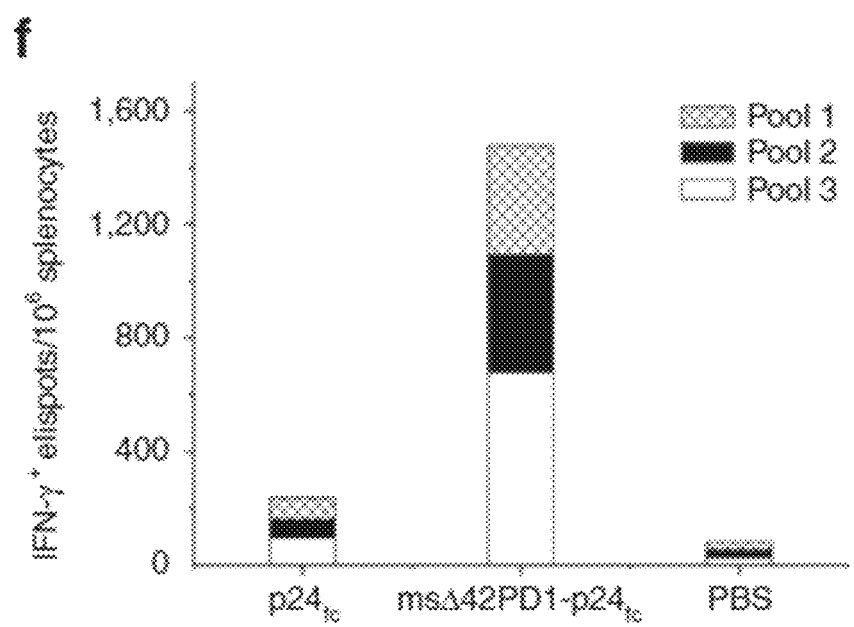

The antigen specificity of CD8$^+$ T cells from mice vaccinated (20 μg dose) with msΔ42PD1-p24$_{fc}$ was examined, and the results show a greater frequency of p24-specific tetramer$^+$ CD8$^+$ T cells at an average of 17% compared to those in p24$_{fc}$ group (>11-fold; P<0.05; FIG. 4E). Additionally, epitopic breadth was enhanced in splenocytes detected using three non-overlapping p24 peptide pools (FIG. 4F).

Example 5—Long-Term Memory CD8$^+$ T Cells Immune Responses is Sustained in MsΔ42PD1-P24$_{Fc}$ Immunized Mice To determine if long-term memory responses can be achieved with msΔ42PD1-p24$_{fc}$, p24-specific cell-mediated immunity was examined 30 weeks (7.5 months) post-vaccination. Anti-p24 antibody titers were retained at 100 μg groups, with IgG1 and IgG2a responses being higher for msΔ42PD1-p24$_{fc}$ compared to p24$_{fc}$; however, at 20 μg dose, antibody responses of both groups remained relatively low (FIG. 5A). Although memory CD4$^+$ IFN-γ$^+$ Elispots was not apparent unless a higher dose of 100 μg DNA vaccine was used (~2-fold; P<0.05; FIG. 5B), CD8$^+$ T cell immunity is long-lived, as a significant level of CD8$^+$ IFN-γ$^+$ Elispots could still be detected 30 weeks after msΔ42PD1-p24$_{fc}$ DNA vaccination in two doses (FIG. 5B).

Figure 5C:
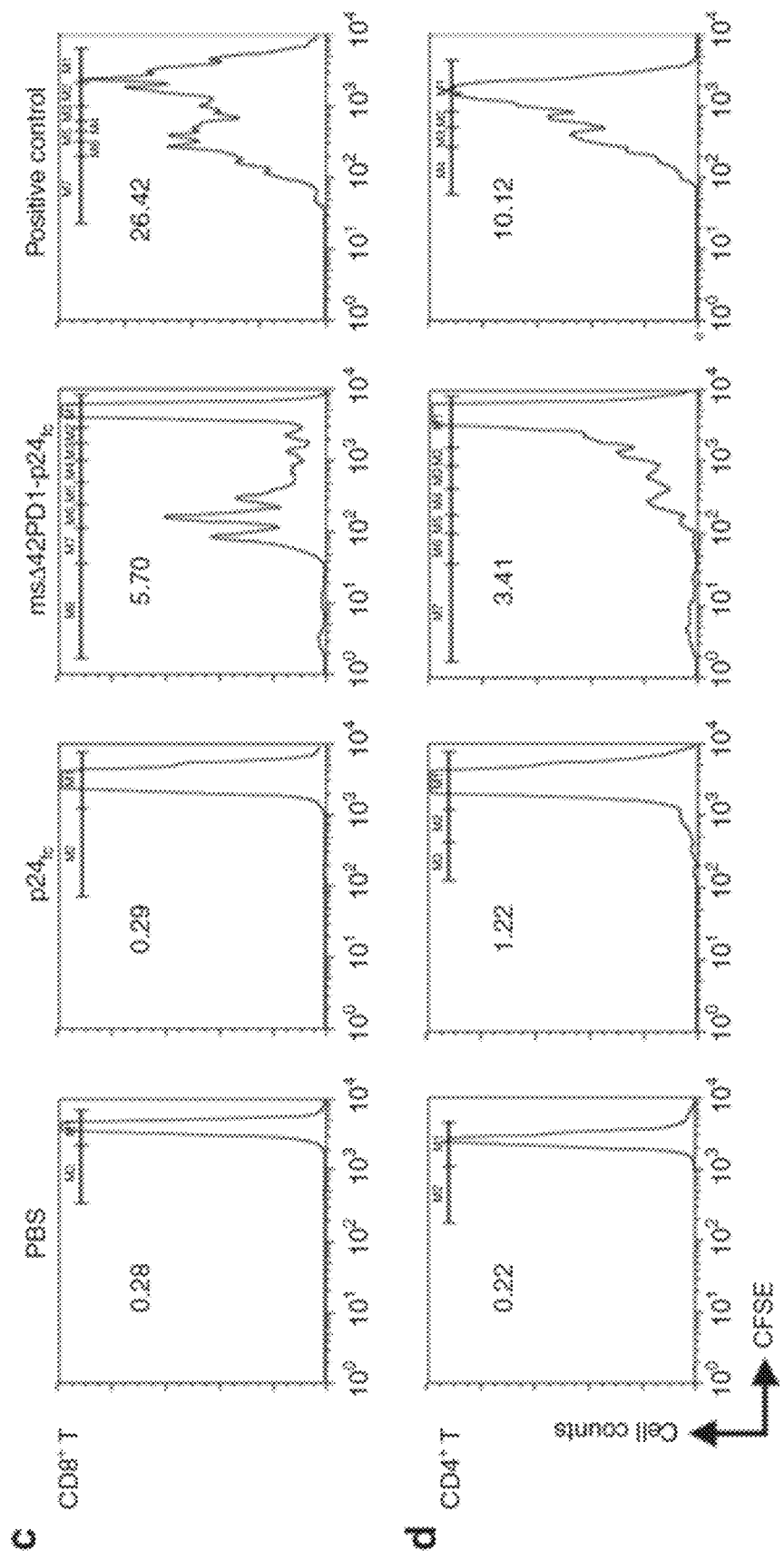

Also, proliferative memory T cells were evaluated by CFSE assay for both CD4$^+$ and CD8$^+$ T cells in splenocytes isolated from 30 weeks post-vaccinated mice. The data showed that CD4$^+$ T cells from p24$_{fc}$- or msΔ42PD1-p24$_{fc}$-vaccinated mice (at 100 μg dose) were minimally proliferative upon stimulation with BM-DCs plus p24 peptide pool (FIG. 5C). However, ~16% of CD8$^+$ T cells of the msΔ42PD1-p24$_{fc}$ group proliferated following stimulation, while p24$_{fc}$ group remained at levels similar to the placebo group (FIG. 5D). Overall, the use of msΔ42PD1 as an intramolecular adjuvant in the DNA vaccine vastly improved the elucidation of the levels of antigen-specific long-lived B and T cell immunity, especially CD8$^+$ T cell immune responses compared to antigen alone.

Example 6—The Efficacy of MSΔ42PD1-P24FC DNA Vaccine in Mice

To assess the efficacy of our fusion DNA vaccine, this Example determines whether these CD8$^+$ T cells are cytolytic and provide protection. CTL assay was performed using a modified mesothelioma cell line (AB1) to express HIV-1 Gag with luciferase as target cells (AB1-HIV-1-Gag). Splenocytes isolated from vaccinated mice (two weeks post-vaccination) were co-cultured at various ratios with AB1-HIV-1-Gag target cells and the frequency of dead target cells was measured.

Compared to p24$_{fc}$ or placebo groups, splenocytes isolated from msΔ42PD1-p24$_{fc}$ immunized mice were able to kill efficiently even at a ratio of one effector T cell to two target cells (FIG. 6A).

To evaluate whether msΔ42PD1-p24$_{fc}$ protects vaccinated mice from tumor challenge, mice were immunized with 100 μg msΔ42PD1-p24$_{fc}$ and p24$_{fc}$. i.m./EP n (FIG. 12C). Three weeks after the last boost, mice were challenged subcutaneously (s.c.) using 5×10$^5$ AB1-HIV-1-Gag tumor cells, and in vivo imaging was performed twice a week up to 3 weeks.

As shown in FIGS. 6B and 6C, the results showed that the tumor growth in msΔ42PD1-p24$_{fc}$-vaccinated mice was inhibited up to 17 days compared to p24$_{fc}$ and PBS control, showing that msΔ42PD1-p24$_{fc}$ vaccination conferred protective immunity against tumor growth systematically.

Furthermore, the protection of vaccinated mice against virus infection was assessed. Briefly, msΔ42PD1-p24$_{fc}$-, p24$_{fc}$- and PBS vaccinated mice were challenged (at three weeks post-vaccination) by either vaccinia virus strain Tian-Tan (WRgagpol) (for 20 μg dose vaccinated mice) or virulent strain Western Reserve (WRgagpol) (for 100 μg dose vaccinated mice).

Significantly less virus titer was found in lung homogenates of msΔ42PD1-p24$_{fc}$ group compared to p24$_{fc}$ or placebo groups (FIGS. 6D and 6E), and significantly reduced body weight loss (FIG. 6F). The results show the immunogenic advantage of msΔ42PD1-p24$_{fc}$ in eliciting p24-specific protective immunity.

Figure 8:
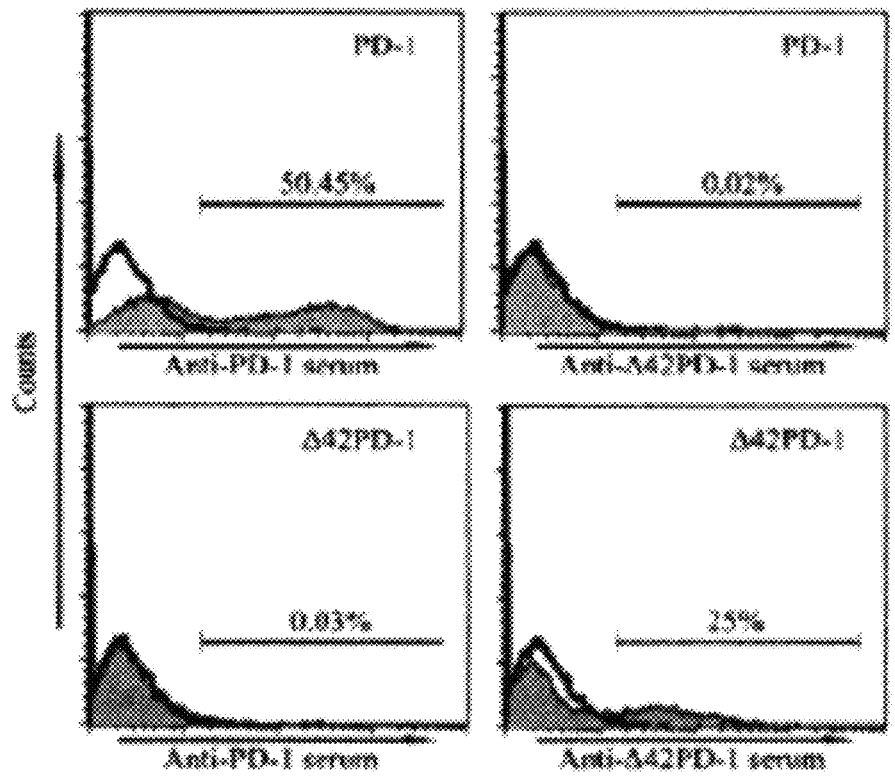
FIG. 8 shows lack of cross-reactivity of murine immune sera against human PD1 and Δ42PD1. 293T cells transfected with plasmids encoding PD1 (top) and Δ42PD1 (bottom) were stained by anti-PD1 and anti-Δ42PD1 immune sera, respectively, by FACS analysis.
Figure 9:
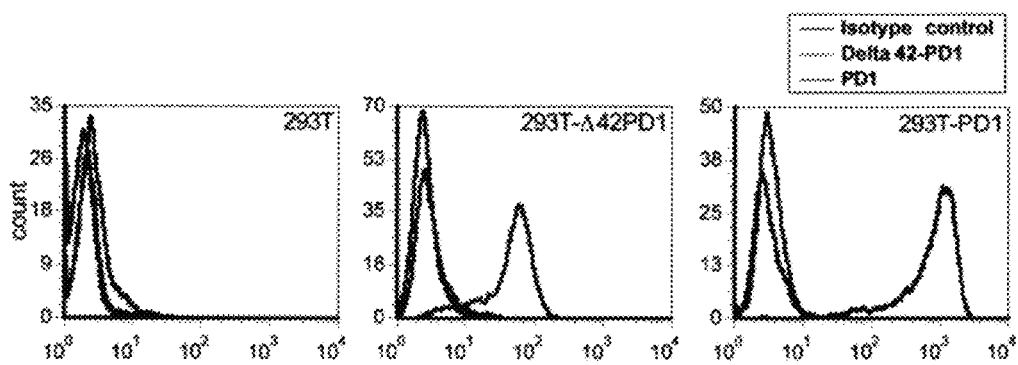
FIG. 9 shows the specificity of a specific monoclonal antibody (clone CH34) targeting human Δ42PD1. 293T cells transfected with plasmids encoding human PD1 (right) and Δ42PD1 (middle) were stained by anti-PD1 and anti-Δ42PD1 monoclonal antibody CH34 (red) or anti-PD1 monoclonal antibody (blue) or isotype control (black) respectively, by FACS analysis.

Example 7—Mouse Immunization and Cell Fusion to Generate Anti-Human Δ42PD1 mAbs When human sΔ42PD1-p24 was used to immunize mice, a strong antibody response was induced against the Δ42PD1 protein. This response does not significantly cross-react with human PD1 (FIG. 8), which is similar to that PD1 specific monoclonal antibody does not cross-react with Δ42PD1 (FIG. 2C). It is demonstrated that it is feasible to generate a monoclonal antibody specific to Δ42PD1 in animals. The key point is that anti-Δ42PD1 specific antibody can only be elicited using Δ42PD1 or soluble Δ42PD1 as immunogen, which is one of the key inventions of this patent application.

Figure 19:
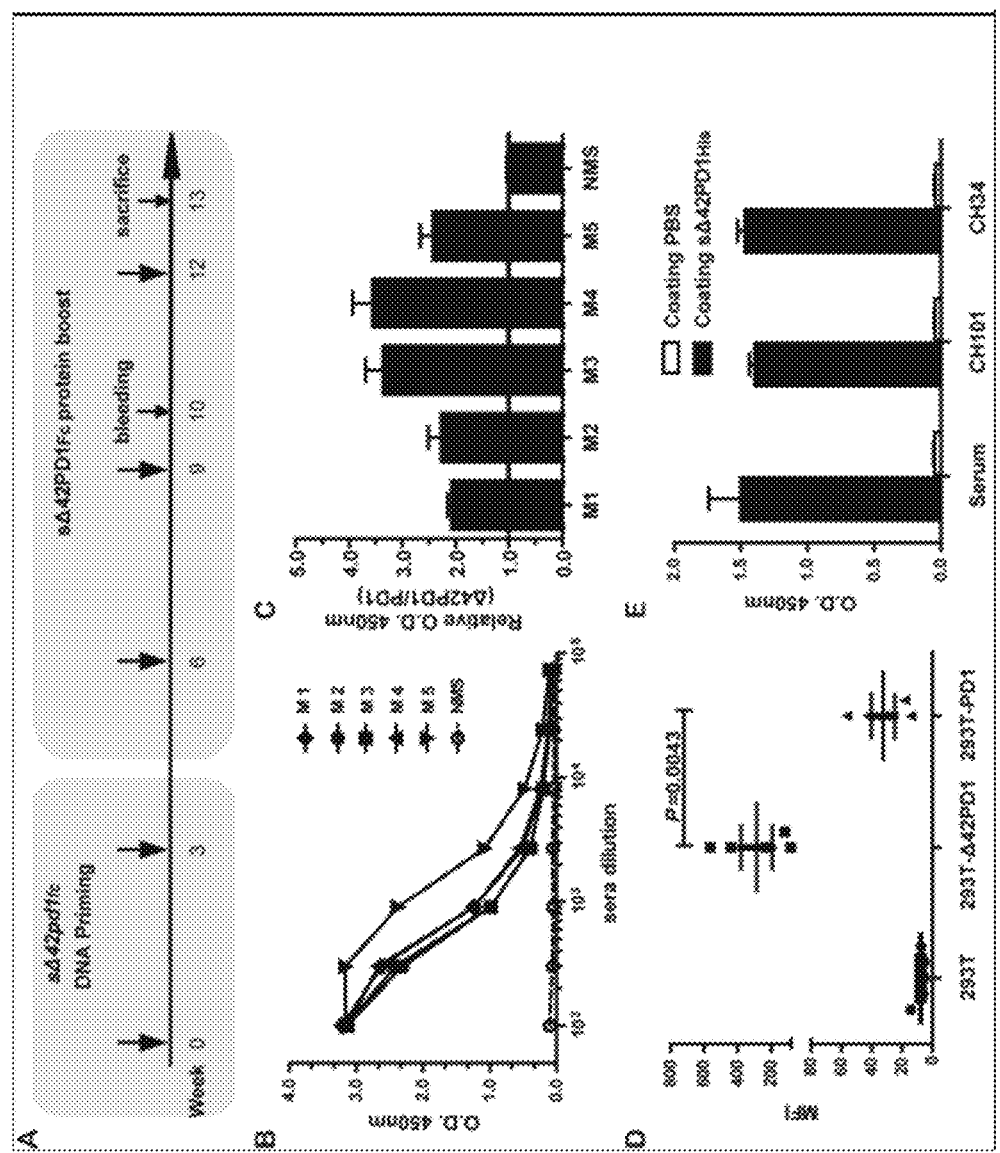

To elicit human Δ42PD1 specific antibody response, a DNA prime/protein boost immunization regimen was utilized. Briefly, mice were immunized with sΔ42pd1fc plasmids, which fused expression the extracellular domain of human Δ42PD1 (soluble Δ42PD1 (sΔ42PD1) and rabbit IgG1 Fc region, at weeks 0 and 3 by intramuscular injection plus electroporation, followed by two additional subcutaneous injections of purified recombinant sΔ42PD1Fc protein in three-week intervals (FIG. 19A). One week after the second protein boost (week 10), serum samples were collected for analysis for the presence of antibodies recognizing soluble Δ42PD1 protein. Serial three-fold dilution starting from 1/100 of sera were assessed in a indirect ELISA using immobilized sΔ42PD1His protein purified from the supernatants of the 293F cells, and IgG anti-sΔ42PD1 titers were measured. Similar levels of antibody titers were observed in serum samples from mice #1-4, and serum antibody titer of mouse #5 was approximately 2-fold higher (FIG. 19B).

Before performing cell fusion assay for hybridoma generation, the recognition bias of serum samples from inoculated mice to human PD1 or Δ42PD1 was assessed. Firstly, the binding activity of serum samples to sΔ42PD1His and sPD1His proteins was determined by ELISA. Both proteins were bound with all five serum samples. However, the optical density at 450 nm (O.D.450 nm) value was at least 2-fold higher for sΔ42PD1His than PD1His (FIG. 19C). Secondly, it was flow cytometrically evaluated the recognizing activity of serum samples to mature Δ42PD1 and PD1 on cell surface using 293T, 293T-Δ42PD1, and 293T-PD1 cell lines. The mean fluorescence intensities (MFI) of serum samples interacting with the three cell lines were used to generate the scatter plot shown in FIG. 19D. As expected, antibodies in serum samples did not engage with 293T cells, however bound with high affinity to Δ42PD1 expressed on 293T cell surface, with relatively lower affinity to cell surface PD1, and this difference is statistically significant (p=0.0043). Together, these data demonstrated that human Δ42PD1 is immunogenically different from PD1 and that antibodies generated in Δ42PD1 immunized mice have a strong bias toward Δ42PD1 recognition compare to PD1 recognition.

Since serum from the #4 mouse possesses the strongest bias toward soluble Δ42PD1 and cell-surface expressed natural Δ42PD1 compared with soluble PD1 and cell surface PD1. Therefore, the #4 mouse was immunized a final time at week 12 and sacrificed at week 13 to harvest spleen cells for fusion with SP2/0-Ag14 myeloma cells. Since high affinity mAbs were desired, hybridoma culture supernatants were screened for Δ42PD1-specific IgG but not IgM or IgA based on their ability to bind to sΔ42PD1His immobilized in microtiter plates in indirect ELISA. Subsequently, two hybridoma cell lines (clone CH34 and CH101) secreting Δ42PD1 highly reactive mAbs were identified (FIG. 19E).

Example 8—Anti-Human Δ42PD1 Mabs do not Cross-React with PD1

To evaluate cross-reactivity of mAbs induced by Δ42PD1 to PD1, binding of anti-Δ42PD1 mAbs to cell surface expressed human Δ42PD1 and human PD1 was flow cytometrically analyzed using 293T, 293T-Δ42PD1 and 293T-PD1 cell lines. Both anti-Δ42PD1 mAbs (clone CH34 and CH101) specifically recognized human Δ42PD1 without cross-reacting to human PD1 (FIG. 20A) (FIG. 8) Secondly, the applicability and specificity of anti-Δ42PD1 mAbs in Western blot was explored. Besides human PD1 and Δ42PD1, mouse Δ42PD1 was also included considering which exhibits approximately 64% amino acid sequence homology with human sΔ42PD1, notwithstanding that mouse Δ42PD1 isoform have not been discovered yet. 293T cells were transiently transfected with human Δ42pd1, human pd1 and mouse sΔ42pd1$_{fc}$, respectively. Two days post-transfection, cells were lysed and whole cell lysates were prepared for Western blot. As shown in FIG. 20B, the two anti-Δ42PD1 mAbs (clone CH34 and CH101) recognized denatured human PD1 and Δ42PD1 but not mouse Δ42PD1. Both anti-Δ42PD1 mAbs could flow cytometrically distinguish human Δ42PD1 from PD1, auguring a crucial role in future functional research on human Δ42PD1. Therefore, isotypes and avidity were identified of the anti-Δ42PD1 mAbs to facilitate future utilization using rapid ELISA mouse mAb isotyping kit (37503, Pierce Biotechnology) and surface plasmon resonance, respectively. As shown in FIG. 20C and FIG. 23, isotype of clone CH34 is IgG2b/Kappa and clone CH101 turn out to be IgG1/Kappa. Collectively, these data demonstrated that both anti-human Δ42PD1 mAbs specifically engage with cell surface human Δ42PD1 but not human PD1 in Flow cytometry, interestingly recognize both human Δ42PD1 and PD1 but not mouse Δ42PD1 in Western blot.

The antibodies CH34 and CH101 can be purchased by contacting University of Hong Kong.

Example 9—Raised Plasma SΔ42PD1 in HIV Infection

Chronic immune activation is a characteristic feature of progressive HIV disease. Indeed, polyclonal B-cell activation was one of the first described immunological abnormalities in HIV-infected individuals. Subsequently, increased T-cell turnover, increased frequencies of T cells with an activated phenotype, and increased serum levels of proinflammatory cytokines and chemokines were observed. Notably, the degree of immune activation is a better predictor of disease progression than plasma viral load. However, the underlying causes of immune activation have remained elusive.

sΔ42PD1 could induce production of proinflammatory cytokines in vivo, which could lead to immune activation. To explore whether sΔ42PD1 plays a role in HIV progress, we determined sΔ42PD1 level in HIV+ (n=11) and HIV− (n=21) plasma using DAS-ELISA. As shown in FIG. 22, sΔ42PD1 level in HIV+ plasma is significantly higher than HIV− plasma.

This result indicated that sΔ42PD1 plays a role in HIV infection and progression. Besides HIV infection, some other viral infection and autoimmune diseases also featured as immune activation. So it is very important to determine the plasma level of sΔ42PD1 in these patients.

Example 10—Augmentation of Membrane-Bound Δ42PD1 Signaling by Specific MAB

Engagement of PD1 by its ligands triggers transduction of inhibitory signal which could inhibit PI3K-Akt signal pathway. PBMCs express ligands of PD1 and also unknown ligand(s) of Δ42PD1, which is confirmed by a proinflammatory cytokines release response to Δ42PD1 treatment. So we attempted to trigger PD1 and Δ42PD1 signaling by mixing human PBMCs and human PD1 or Δ42PD1 expressing 293T cells with different ratio to determine whether Δ42PD1 which possesses exactly the same intracellular region with PD1 could also transduce inhibitory signal while bound by its unknown ligand(s). As expected, treatment with PBMCs significantly decreased the phosphorylation of Akt in 293T-PD1 cells but not in 293T cells, compared with untreated cells. Similarly, the level of phosphorylated Akt in 293T-Δ42PD1 cells was significantly lower upon PBMCs stimulation (FIG. 24). These results strongly suggest a negatively immune regulatory function of membrane-bound Δ42PD1, although no direct evidence of the inhibitory effect has been obtained yet. To determine whether monoclonal antibody CH34 and CH101 have agonist or antagonist activities, 293T-Δ42PD1 cells were treated with Δ42PD1 specific mAbs or isotype matched controls. Levels of phosphorylated Akt in 293T-Δ42PD1 cells were detected subsequently or followed by mixing with PBMCs. As shown in FIG. 25, no blocking effect of Δ42PD1 specific mAbs on attenuation of Akt phosphorylation in 293T-Δ42PD1 cells triggered by PBMC were observed, indicating non antagonist activities of CH34 and CH101 on Δ42PD1 signaling.

Unexpectedly, anti-Δ42PD1 mAb clone CH101 synergistically decrease p-AKT intensity induced by unknown Δ42PD1 ligand(s) expressed on PBMCs. These results suggested that membrane-bound Δ42PD1 could functionally transduce inhibitory signal through cytoplasmicregion, and play a role in immune system.

Given that both Δ42PD1 and its unknown ligand(s) expressed among PBMCs, mAb CH101 probably behaves as a Δ42PD1 agonist in vivo and potentially contribute to autoimmune disease treatment.

Example 11—Blockage of Δ42PD1 Binding to its Receptor by Specific mAb

To determine if Δ42PD1 specific monoclonal antibody could block the engagement of Δ42PD1 with its unknown receptor(s), we mixed sΔ42PD1fc recombinant proteins with various doses of CH34, CH101 and isotype matched mouse derived control monoclonal antibodies, and then used the mixture to incubate THP-1 cells, followed by staining with fluorescent labeled antibody to detect the binding of sΔ42PD1fc recombinant proteins to THP-1 cells. mAb CH101 blocked the binding of Δ42PD1 to its unknown receptor on THP-1 with a dose dependent pattern. On the contrary, mAb CH34 did not block the binding of Δ42PD1 to its receptor (FIG. 26).

sΔ42PD1 could induce production of proinflammatory cytokines in vivo, which play a key role in autoimmune disorders. The blockage of the binding of sΔ42PD1 to its receptor by specific monoclonal antibody is one potential way to treatment these autoimmune disease.

Example 12—Double-Monoclonal Antibody Sandwich Indirect ELISA for sΔ42PD1 Detection PD1 has a soluble form which interferes with physiological functions of PD1: PD-Ls axis and leads to autoimmune disease. It is highly possible that soluble form of Δ42PD1 also exists and plays a role in a particular ailment. Therefore we wanted to develop a double-monoclonal antibody sandwich indirect enzyme-linked immunosorbent assay (DAS-ELISA) based on Δ42PD1 specific mAbs (clone CH34 and CH101) for the assessment of sΔ42PD1 concentrations in human body fluid.

The top concern for the development of sΔ42PD1-detecting DAS-ELISA system is whether sPD1 could also be detected, considering the fact that both CH34 and CH101 recognize human PD1 by Western blot. So we tested the DAS-ELISA system using commercially available recombinant human $sPD1_{Fc}$ and home-made recombinant $sΔ42PD1_{Fc}$. As shown in FIG. 27, antibody CH34 and CH101 based DAS-ELISA system could detect ultra-trace level of human sΔ42PD1 but not sPD1.

Example 13—Binding of mAb to Δ42PD1 Fragments

For mapping the epitope of Δ42PD1 specific mAbs, 6 fragments (Δ42PD1 F1-F6) of Δ42PD1 (FIG. 28A) were displayed on the surface yeast cells (Y-F1 to Y-F6). The binding of CH34 and CH101 to the Δ42PD1 fragments were analyzed by flow cytometry. As shown in FIG. 28B, mAb could bind the Δ42PD1 F2 but not other fragments. However, CH34 failed to bind any of the 6 fragments of Δ42PD1.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Ishida Y, Agata Y, Shibahara K, Honjo T. Induced expression of PD1, a novel member of the immunoglobulin gene superfamily, upon programmed cell death. Embo J 1992; 11(11): 3887-95.

Freeman G J, Long A J, Iwai Y, Bourque K, Chernova T, Nishimura H et al. Engagement of the PD1 immunoinhibitory receptor by a novel B7 family member leads to negative regulation of lymphocyte activation. J Exp Med 2000; 192(7): 1027-34.

Latchman Y, Wood C R, Chernova T, Chaudhary D, Borde M, Chernova I et al. PD-L2 is a second ligand for PD1 and inhibits T cell activation. Nat Immunol 2001; 2(3): 261-8.

Greenwald R J, Freeman G J, Sharpe A H. The B7 family revisited. Annu Rev Immunol 2005; 23: 515-48.

Okazaki T, Honjo T. The PD1-PD-L pathway in immunological tolerance. Trends Immunol 2006; 27(4): 195-201.

Yao S, Wang S, Zhu Y, Luo L, Zhu G, Flies S et al. PD1 on dendritic cells impedes innate immunity against bacterial infection. Blood 2009; 113(23): 5811-8.

Prokunina L, Castillejo-Lopez C, Oberg F, Gunnarsson I, Berg L, Magnusson V et al. A regulatory polymorphism in PDCD1 is associated with susceptibility to systemic lupus erythematosus in humans. Nat Genet. 2002; 32(4): 666-9.

Lin S C, Yen J H, Tsai J J, Tsai W C, Ou T T, Liu H W et al. Association of a programmed death 1 gene polymorphism with the development of rheumatoid arthritis, but not systemic lupus erythematosus. Arthritis Rheum 2004; 50(3): 770-5.

Jurado J O, Alvarez I B, Pasquinelli V, Martinez G J, Quiroga M F, Abbate E et al. Programmed death (PD)-1:PD-ligand 1/PD-ligand 2 pathway inhibits T cell effector functions during human tuberculosis. J Immunol 2008; 181(1): 116-25.

Day C L, Kaufmann D E, Kiepiela P, Brown J A, Moodley E S, Reddy S et al. PD1 expression on HIV-specific T cells is associated with T-cell exhaustion and disease progression. Nature 2006; 443(7109): 350-4.

Urbani S, Amadei B, Tola D, Massari M, Schivazappa S, Missale G et al. PD1 expression in acute hepatitis C virus (HCV) infection is associated with HCV-specific $CD8^+$ exhaustion. J Virol 2006; 80(22): 11398-403.

Nielsen C, Ohm-Laursen L, Barington T, Husby S, Lillevang S T. Alternative splice variants of the human PD1 gene. Cell Immunol 2005; 235(2): 109-16.

Wan B, Nie H, Liu A, Feng G, He D, Xu R et al. Aberrant regulation of synovial T cell activation by soluble costimulatory molecules in rheumatoid arthritis. J Immunol 2006; 177(12): 8844-50.

Liu S M, Sutherland A P, Zhang Z, Rainbow D B, Quintana F J, Paterson A M et al. Overexpression of the Ctla-4 isoform lacking exons 2 and 3 causes autoimmunity. J Immunol 2012; 188(1): 155-62.

Magistrelli G, Jeannin P, Elson G, Gauchat J F, Nguyen T N, Bonnefoy J Y et al., Identification of three alternatively spliced variants of human CD28 mRNA. Biochem Biophys Res Commun 1999; 259(1): 34-7.

Hanawa H, Ma Y, Mikolajczak S A, Charles M L, Yoshida T, Yoshida R et al. A novel costimulatory signaling in human T lymphocytes by a splice variant of CD28. Blood 2002; 99(6): 2138-45.

Matlin A J, Clark F, Smith C W. Understanding alternative splicing: towards a cellular code. Nat Rev Mol Cell Biol 2005; 6(5): 386-98.

Thanaraj T A, Clark F. Human GC-AG alternative intron isoforms with weak donor sites show enhanced consensus at acceptor exon positions. *Nucleic Acids Res* 2001; 29(12):2581-93.

Lazar-Molnar E, Yan Q, Cao E, Ramagopal U, Nathenson S G, Almo S C. Crystal structure of the complex between programmed death-1 (PD1) and its ligand PD-L2. *Proc Natl Acad Sci USA* 2008; 105(30): 10483-8.

Joffre O, Nolte M A, Sporri R, Reis e Sousa C. Inflammatory signals in dendritic cell activation and the induction of adaptive immunity. *Immunol Rev* 2009; 227(1): 234-47.

Aihara H, Miyazaki J. Gene transfer into muscle by electroporation in vivo. *NatBiotechnol* 1998; 16(9): 867-70.

Davis M R, Manning L S, Whitaker D, Garlepp M J, Robinson B W. Establishment of a murine model of malignant mesothelioma. *Int J Cancer* 1992; 52(6): 881-6.

Giorelli M, Livrea P, Defazio G, Ricchiuti F, Pagano E, Trojano M. IFN-beta1a modulates the expression of CTLA-4 and CD28 splice variants in human mononuclear cells: induction of soluble isoforms. *J Interferon Cytokine Res* 2001; 21(10): 809-12.

Hebbar M, Jeannin P, Magistrelli G, Hatron P Y, Hachulla E, Devulder B et al. Detection of circulating soluble CD28 in patients with systemic lupus erythematosus, primary Sjogren's syndrome and systemic sclerosis. *Clin Exp Immunol* 2004; 136(2): 388-92.

Wong C K, Lit L C, Tam L S, Li E K, Lam C W. Aberrant production of soluble costimulatory molecules CTLA-4, CD28, CD80 and CD86 in patients with systemic lupus erythematosus. *Rheumatology (Oxford)* 2005; 44(8): 989-94.

Wang H, Wang K, Zhong X, Dai Y, Wu A, Li Y et al. Plasma sCD28, sCTLA-4 levels in neuromyelitis optica and multiple sclerosis during relapse. *J Neuroimmunol* 2012; 243(1-2): 52-5.

Koup R A, Douek D C. Vaccine design for CD8$^+$ T lymphocyte responses. *Cold Spring Harb Perspect Med* 2011; 1(1): a007252.

Chen Z, Huang Y, Zhao X, Ba L, Zhang W, Ho D D. Design, construction, and characterization of a multigenic modified vaccinia Ankara candidate vaccine against human immunodeficiency virus type 1 subtype C/B'. *J Acquir Immune Defic Syndr* 2008; 47(4): 412-21.

Huang Y, Chen Z, Zhang W, Gurner D, Song Y, Gardiner D F et al. Design, construction, and characterization of a dual-promoter multigenic DNA vaccine directed against an HIV-1 subtype C/B' recombinant. *J Acquir Immune Defic Syndr* 2008; 47(4): 403-11.

Li Z, Zhang M, Zhou C, Zhao X, Iijima N, Frankel F R. Novel vaccination protocol with two live mucosal vectors elicits strong cell-mediated immunity in the vagina and protects against vaginal virus challenge. *J Immunol* 2008; 180(4): 2504-13.

Dai B, Yang L, Yang H, Hu B, Baltimore D, Wang P. HIV-1 Gag-specific immunity induced by a lentivector-based vaccine directed to dendritic cells. *Proc Natl Acad Sci U S A* 2009; 106(48): 20382-7.

Roake J A, Rao A S, Morris P J, Larsen C P, Hankins D F, Austyn J M. Dendritic cell loss from nonlymphoid tissues after systemic administration of lipopolysaccharide, tumor necrosis factor, and interleukin 1. *The Journal of experimental medicine* 1995; 181(6):2237-47.

33. Trevejo J M, Marino M W, Philpott N, Josien R, Richards E C, Elkon K B et al. TNF-alpha-dependent maturation of local dendritic cells is critical for activating the adaptive immune response to virus infection. *Proc Natl Acad Sci USA* 2001; 98(21): 12162-7.

de Jong E C, Vieira P L, Kalinski P, Schuitemaker J H, Tanaka Y, Wierenga E A et al. Microbial compounds selectively induce Th1 cell-promoting or Th2 cell-promoting dendritic cells in vitro with diverse th cell-polarizing signals. *J Immunol* 2002; 168(4):1704-9.

Klagge I M, Abt M, Fries B, Schneider-Schaulies S. Impact of measles virus dendritic-cell infection on Th-cell polarization in vitro. *J Gen Virol* 2004; 85(Pt 11): 3239-47.

Kuhweide R, Van Damme J, Ceuppens J L. Tumor necrosis factor-alpha and interleukin 6 synergistically induce T cell growth. *Eur J Immunol* 1990; 20(5): 1019-25.

Detournay O, Mazouz N, Goldman M, Toungouz M. IL-6 produced by type I IFN DC controls IFN-gamma production by regulating the suppressive effect of CD4+ CD25+ regulatory T cells. *Hum Immunol* 2005; 66(5): 460-8.

Kim J J, Ayyavoo V, Bagarazzi M L, Chattergoon M, Boyer J D, Wang B et al. Development of a multicomponent candidate vaccine for HIV-1. *Vaccine* 1997; 15(8):879-83.

Agadjanyan M G, Kim J J, Trivedi N, Wilson D M, Monzavi-Karbassi B, Morrison L D et al. CD86 (B7-2) can function to drive MHC-restricted antigen-specific CTL responses in vivo. *J Immunol* 1999; 162(6): 3417-27.

Shedlock D J, Weiner D B. DNA vaccination: antigen presentation and the induction of immunity. *J Leukoc Biol* 2000; 68(6): 793-806.

Hirao L A, Wu L, Khan A S, Hokey D A, Yan J, Dai A et al. Combined effects of IL-12 and electroporation enhances the potency of DNA vaccination in macaques. *Vaccine* 2008; 26(25): 3112-20.

Ontiveros F, Wilson E B, Livingstone A M. Type I interferon supports primary CD8+ T-cell responses to peptide-pulsed dendritic cells in the absence of CD4+ T-cell help. *Immunology* 2011; 132(4): 549-58.

Oh S, Perera L P, Terabe M, Ni L, Waldmann T A, Berzofsky J A. IL-15 as a mediator of CD4+ help for CD8+ T cell longevity and avoidance of TRAIL-mediated apoptosis. *Proc Natl Acad Sci USA* 2008; 105(13): 5201-6.

von Rossum A, Krall R, Escalante N K, Choy J C. Inflammatory cytokines determine the susceptibility of human CD8$^+$ T cells to Fas-mediated activation-induced cell death through modulation of FasL and c-FLIP(S) expression. *J Biol Chem* 2011; 286(24): 21137-44.

Wuthrich M, Filutowicz H I, Warner T, Deepe G S, Jr., Klein B S. Vaccine immunity to pathogenic fungi overcomes the requirement for CD4$^+$ help in exogenous antigen presentation to CD8+ T cells: implications for vaccine development in immune-deficient hosts. *The Journal of experimental medicine* 2003; 197(11): 1405-16.

Onlamoon N, Rogers K, Mayne A E, Pattanapanyasat K, Mori K, Villinger F et al. Soluble PD1 rescues the proliferative response of simian immunodeficiency virus-specific CD4$^+$ and CD8$^+$ T cells during chronic infection. *Immunology* 2008; 124(2): 277-93.

Akira, S., and Takeda, K. (2004). Toll-like receptor signalling. Nat. Rev. Immunol. 4, 499-511. Andersson, U., and Tracey, K. J. (2011). HMGB1 is a therapeutic target for sterile inflammation and infection. Annu. Rev. Immunol. 29, 139-162.

Apetoh, L., Ghiringhelli, F., Tesniere, A., Obeid, M., Ortiz, C., Criollo, A., Mignot, G., Maiuri, M. C., Ullrich, E., Saulnier, P., et al. (2007). Toll-like receptor 4-dependent contribution of the immune system to anticancer chemotherapy and radiotherapy. Nat. Med. 13, 1050-1059.

Bacon, C. M., Petricoin, E. F., Ortaldo, J. R., Rees, R. C., Larner, A. C., Johnston, J. A., and O'Shea, J. J. (1995).

Interleukin 12 induces tyrosine phosphorylation and activation of STAT4 in human lymphocytes. Proc Natl Acad Sci USA 92, 7307-7311.

Bieback, K., Breer, C., Nanan, R., Meulen, ter, V., and Schneider-Schaulies, S. (2003). Expansion of human gamma/delta T cells in vitro is differentially regulated by the measles virus glycoproteins. J. Gen. Virol. 84, 1179-1188.

Brandes, M. (2005). Professional Antigen-Presentation Function by Human gd T Cells. Science 309, 264-268.

Brandes, M., Willimann, K., Bioley, G., Levy, N., Eberl, M., Luo, M., Tampe, R., Levy, F., Romero, P., and Moser, B. (2009). Cross-presenting human gammadelta T cells induce robust CD8+ alphabeta T cell responses. Proc Natl Acad Sci USA 106, 2307-2312.

Brenchley, J. M., and Douek, D. C. (2008). The mucosal barrier and immune activation in HIV pathogenesis. Curr Opin HIV AIDS 3, 356-361.

Cairns, B., Maile, R., Barnes, C. M., Frelinger, J. A., and Meyer, A. A. (2006). Increased Toll-Like Receptor 4 Expression on T Cells May Be a Mechanism for Enhanced T cell Response Late After Burn Injury. The Journal of Trauma: Injury, Infection, and Critical Care 61, 293-299.

Caramalho, I., Lopes-Carvalho, T., Ostler, D., Zelenay, S., Haury, M., and Demengeot, J. (2003). Regulatory T cells selectively express toll-like receptors and are activated by lipopolysaccharide. J. Exp. Med. 197, 403-411.

Cheung, A. K. L., Abendroth, A., Cunningham, A. L., and Slobedman, B. (2006). Viral gene expression during the establishment of human cytomegalovirus latent infection in myeloid progenitor cells. Blood 108, 3691-3699.

Eberl, M., Hintz, M., Reichenberg, A., Kollas, A.-K., Wiesner, J., and Jomaa, H. (2003). Microbial isoprenoid biosynthesis and human gammadelta T cell activation. FEBS Lett. 544, 4-10.

Evans, P. S., Enders, P. J., Yin, C., Ruckwardt, T. J., Malkovsky, M., and Pauza, C. D. (2001). In vitro stimulation with a non-peptidic alkylphosphate expands cells expressing Vgamma2-Jgamma1.2/Vdelta2 T-cell receptors. Immunology 104, 19-27.

Gober, H.-J., Kistowska, M., Angman, L., Jenö, P., Mori, L., and De Libero, G. (2003). Human T cell receptor gammadelta cells recognize endogenous mevalonate metabolites in tumor cells. J. Exp. Med. 197, 163-168.

Kabelitz, D. (2007). Expression and function of Toll-like receptors in T lymphocytes. Curr. Opin. Immunol. 19, 39-45.

Kang, Y., Wu, Z., Lau, T. C. K., Lu, X., Liu, L., Cheung, A. K. L., Tan, Z., Ng, J., Liang, J., Wang, H., et al. (2012). CCR5 antagonist TD-0680 uses a novel mechanism for enhanced potency against HIV-1 entry, cell-mediated infection, and a resistant variant. J. Biol. Chem. 287, 16499-16509.

Kapsenberg, M. L. (2003). Dendritic-cell control of pathogen-driven T-cell polarization. Nat. Rev. Immunol. 3, 984-993.

Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature 441, 101-105.

Kim, S., Kim, S. Y., Pribis, J. P., Lotze, M., Mollen, K. P., Shapiro, R., Loughran, P., Scott, M. J., and Billiar, T. R. (2013). Signaling of high mobility group box 1 (HMGB1) through toll-like receptor 4 in macrophages requires CD14. Mol. Med. 19, 88-98.

Li, W., Kubo, S., Okuda, A., Yamamoto, H., Ueda, H., Tanaka, T., Nakamura, H., Yamanishi, H., Terada, N., and Okamura, H. (2010). Effect of IL-18 on expansion of gammadelta T cells stimulated by zoledronate and IL-2. J. Immunother. 33, 287-296.

Liddell, J. E. (1991). A Practical Guide to Monoclonal Antibodies (John Wiley & Sons).

Lu, X., Liu, L., Zhang, X., Lau, T. C. K., Tsui, S. K. W., Kang, Y., Zheng, P., Zheng, B., Liu, G., and Chen, Z. (2012). F18, a novel small-molecule nonnucleoside reverse transcriptase inhibitor, inhibits HIV-1 replication using distinct binding motifs as demonstrated by resistance selection and docking analysis. Antimicrob. Agents Chemother. 56, 341-351.

Meuter, S., Eberl, M., and Moser, B. (2010). Prolonged antigen survival and cytosolic export in cross-presenting human gammadelta T cells. Proc Natl Acad Sci USA 107, 8730-8735.

Mogensen, T. H., and Paludan, S. R. (2001). Molecular pathways in virus-induced cytokine production. Microbiol. Mol. Biol. Rev. 65, 131-150.

Moser, B., and Eberl, M. (2007). gammadelta T cells: novel initiators of adaptive immunity. Immunol. Rev. 215, 89-102.

Muul, L. M., Heine, G., Silvin, C., James, S. P., Candotti, F., Radbruch, A., and Worm, M. (2011). Measurement of proliferative responses of cultured lymphocytes. Curr Protoc Immunol Chapter 7, Unit7.10.

Nishimura, H., Hiromatsu, K., Kobayashi, N., Grabstein, K. H., Paxton, R., Sugamura, K., Bluestone, J. A., and Yoshikai, Y. (1996). IL-15 is a novel growth factor for murine gamma delta T cells induced by *Salmonella* infection. J. Immunol. 156, 663-669.

Pichyangkul, S., Saengkrai, P., Yongvanitchit, K., Stewart, A., and Heppner, D. G. (1997). Activation of gammadelta T cells in malaria: interaction of cytokines and a schizont-associated *Plasmodium falciparum* antigen. J. Infect. Dis. 176, 233-241.

Poles, M. A., Barsoum, S., Yu, W., Yu, J., Sun, P., Daly, J., He, T., Mehandru, S., Talal, A., Markowitz, M., et al. (2003). Human Immunodeficiency Virus Type 1 Induces Persistent Changes in Mucosal and Blood T Cells despite Suppressive Therapy. J. Virol. 77, 10456-10467.

Rauser, G., Einsele, H., Sinzger, C., Wernet, D., Kuntz, G., Assenmacher, M., Campbell, J. D. M., and Topp, M. S. (2004). Rapid generation of combined CMV-specific CD4+ and CD8+ T-cell lines for adoptive transfer into recipients of allogeneic stem cell transplants. Blood 103, 3565-3572.

Reynolds, J. M., Martinez, G. J., Chung, Y., and Dong, C. (2012). Toll-like receptor 4 signaling in T cells promotes autoimmune inflammation. Proc Natl Acad Sci USA 109, 13064-13069.

Rossol, M., Heine, H., Meusch, U., Quandt, D., Klein, C., Sweet, M. J., and Hauschildt, S. (2011). LPS-induced cytokine production in human monocytes and macrophages. Crit. Rev. Immunol. 31, 379-446.

Schneider, C. A., Rasband, W. S., and Eliceiri, K. W. (2012). NIH Image to ImageJ: 25 years of image analysis. Nat. Methods 9, 671-675.

Scotet, E., Nedellec, S., Devilder, M.-C., Allain, S., and Bonneville, M. (2008). Bridging innate and adaptive immunity through gammadelta T-dendritic cell crosstalk. Front. Biosci. 13, 6872-6885.

Shimazu, R., Akashi, S., Ogata, H., Nagai, Y., Fukudome, K., Miyake, K., and Kimoto, M. (1999). MD-2, a molecule that confers lipopolysaccharide responsiveness on Toll-like receptor 4. J. Exp. Med. 189, 1777-1782.

Skeen, M. J., and Ziegler, H. K. (1995). Activation of gamma delta T cells for production of IFN-gamma is mediated by bacteria via macrophage-derived cytokines IL-1 and IL-12. J. Immunol. 154, 5832-5841.

Tanaka, Y., Sano, S., Nieves, E., De Libero, G., Rosa, D., Modlin, R. L., Brenner, M. B., Bloom, B. R., and Morita, C. T. (1994). Nonpeptide ligands for human gamma delta T cells. Proc Natl Acad Sci USA 91, 8175-8179.

Ueta, C., Kawasumi, H., Fujiwara, H., Miyagawa, T., Kida, H., Ohmoto, Y., Kishimoto, S., and Tsuyuguchi, I. (1996). Interleukin-12 activates human gamma delta T cells: synergistic effect of tumor necrosis factor-alpha. Eur. J. Immunol. 26, 3066-3073.

Vermijlen, D., Ellis, P., Langford, C., Klein, A., Engel, R., Willimann, K., Jomaa, H., Hayday, A. C., and Eberl, M. (2007). Distinct cytokine-driven responses of activated blood gammadelta T cells: insights into unconventional T cell pleiotropy. J. Immunol. 178, 4304-4314.

Yang, H., Hreggvidsdottir, H. S., Palmblad, K., Wang, H., Ochani, M., Li, J., Lu, B., Chavan, S., Rosas-Ballina, M., Al-Abed, Y., et al. (2010). A critical cysteine is required for HMGB1 binding to Toll-like receptor 4 and activation of macrophage cytokine release. Proc Natl Acad Sci USA 107, 11942-11947.

Yang, Z., Chen, M., Fialkow, L. B., Ellett, J. D., Wu, R., and Nadler, J. L. (2003). Inhibition of STAT4 activation by lisofylline is associated with the protection of autoimmune diabetes. Ann. N.Y. Acad. Sci. 1005, 409-411.

Ye, D., Li, F. Y. L., Lam, K. S. L., Li, H., Jia, W., Wang, Y., Man, K., Lo, C. M., Li, X., and Xu, A. (2012). Toll-like receptor-4 mediates obesity-induced non-alcoholic steatohepatitis through activation of X-box binding protein-1 in mice. Gut 61, 1058-1067.

Zhou, J., Cheung, A. K. L., Tan, Z., Wang, H., Yu, W., Du, Y., Kang, Y., Lu, X., Liu, L., Yuen, K.-Y., et al. (2013a). PD1-based DNA vaccine amplifies HIV-1 GAG-specific CD8+ T cells in mice. J. Clin. Invest. 123, 2629-2642.

Zhou, J., Cheung, A. K., Liu, H., Tan, Z., Tang, X., Kang, Y., Du, Y., Wang, H., Liu, L., and Chen, Z. (2013b). Potentiating functional antigen-specific CD8$^+$ T cell immunity by a novel PD1 isoform-based fusion DNA vaccine. Mol. Ther. 21, 1445-1455.

Zou, W., and Chen, L. (2008). Inhibitory B7-family molecules in the tumour microenvironment. Nat. Rev. Immunol. 8, 467-477.

---

We claim:

1. An antibody that binds specifically to the PD1 protein isoform having the sequence of SEQ ID NO:22, wherein the antibody specifically binds to the PD1 protein isoform as the PD1 isoform exists in a folded native conformation and wherein the antibody does not specifically bind to the wild-type PD1 protein as the wild-type PD1 protein appears on the surface of a human cell that expresses the wild-type PD1 protein, wherein the antibody is CH34.

2. The antibody of claim 1, wherein the human cell that expresses the wild-type PD1 protein is a T-lymphocyte.

3. An antibody that binds specifically to the PD1 protein isoform having the sequence of SEQ ID NO:22, wherein the antibody specifically binds to the PD1 protein isoform as the PD1 isoform exists in a folded native conformation and wherein the antibody does not specifically bind to the wild-type PD1 protein as the wild-type PD1 protein appears on the surface of a human cell that expresses the wild-type PD1 protein, wherein the antibody is CH101.

4. The antibody of claim 3, wherein the human cell that expresses the wild-type PD1 protein is a T-lymphocyte.

* * * * *

UNITED STATES PATENT AND TRADEMARK OFFICE
CERTIFICATE OF CORRECTION

PATENT NO.       : 10,047,137 B2
APPLICATION NO.  : 14/246811
DATED            : August 14, 2018
INVENTOR(S)      : Zhiwei Chen et al.

It is certified that error appears in the above-identified patent and that said Letters Patent is hereby corrected as shown below:

In the Specification

<u>Column 5,</u>
Line 35, "IFN-γ"" should read --IFN-γ$^+$--.

<u>Column 6,</u>
Line 28, "IL6" should read --IL$6$--.

<u>Column 11,</u>
Line 49, "Elispots/10" should read --Elispots/$10^6$--.

<u>Column 28,</u>
Line 40 (Table S3), "IFN-□ TNF-□ ... IL-1□" should read --IFN-g TNF-a ... IL-1a--.
Line 50 (Table S3), "ms□" should read --msD--.

<u>Column 30,</u>
Line 61, "s442pd1$_{fc}$" should read --s$\Delta$42pd1fc--.
Line 63, "and J." should read --and 3.--.

<u>Column 32,</u>
Line 23, "5 μLl/min" should read --5 μl/min--.
Line 32, "30 μLl/min." should read --30 μl/min.--.
Line 43, "100 μLl" should read --100 μl--.
Line 48, "100 μLl" should read --100 μl--.
Line 64, "SΔ10001," should read --SA10001,--.

<u>Column 38,</u>
Line 14, "(WRgagpol)" should read --(VTT*gagpol*)--.

Signed and Sealed this
Thirtieth Day of April, 2019

Andrei Iancu
*Director of the United States Patent and Trademark Office*

Column 40,
Line 56, "cytoplasmicregion," should read --cytoplasmic region,--.